(12) United States Patent
Zimring

(10) Patent No.: US 10,253,109 B2
(45) Date of Patent: Apr. 9, 2019

(54) ANTIBODIES THAT RECOGNIZE RED BLOOD CELL ANTIGENS

(71) Applicant: Bloodworks, Seattle, WA (US)

(72) Inventor: James Charles Zimring, Seattle, WA (US)

(73) Assignee: Bloodworks, Seattle, WA (US)

( * ) Notice: Subject to any disclaimer, the term of this patent is extended or adjusted under 35 U.S.C. 154(b) by 15 days.

(21) Appl. No.: 15/327,629

(22) PCT Filed: Jul. 21, 2015

(86) PCT No.: PCT/US2015/041416
§ 371 (c)(1),
(2) Date: Jan. 19, 2017

(87) PCT Pub. No.: WO2016/014595
PCT Pub. Date: Jan. 28, 2016

(65) Prior Publication Data
US 2017/0210821 A1    Jul. 27, 2017

Related U.S. Application Data

(60) Provisional application No. 62/027,207, filed on Jul. 21, 2014, provisional application No. 62/120,248, filed on Feb. 24, 2015.

(51) Int. Cl.
*C07K 16/34* (2006.01)
*C07K 16/28* (2006.01)
*A61K 39/00* (2006.01)

(52) U.S. Cl.
CPC .......... *C07K 16/34* (2013.01); *C07K 16/2896* (2013.01); *A61K 2039/505* (2013.01); *C07K 2317/24* (2013.01); *C07K 2317/33* (2013.01); *C07K 2317/41* (2013.01); *C07K 2317/52* (2013.01); *C07K 2317/56* (2013.01); *C07K 2317/565* (2013.01); *C07K 2317/71* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 6,255,455 | B1 * | 7/2001 | Siegel | C07K 16/005 435/5 |
| 2006/0039913 | A1 * | 2/2006 | Das | C07K 16/24 424/146.1 |
| 2012/0288493 | A1 | 11/2012 | Bansal | |
| 2012/0328624 | A1 | 12/2012 | Yoshida et al. | |
| 2013/0288387 | A1 | 10/2013 | Blancher et al. | |
| 2015/0037819 | A1 | 2/2015 | Blancher et al. | |

FOREIGN PATENT DOCUMENTS

| | | | | |
|---|---|---|---|---|
| WO | WO2004/101813 | A1 | 11/2004 | |
| WO | WO-2005000901 | A2 * | 1/2005 | ......... C07K 16/2887 |
| WO | WO-2009023816 | A1 * | 2/2009 | ............. C07K 16/00 |
| WO | WO 2010/036460 | A2 | 4/2010 | |
| WO | WO-2010079510 | A2 * | 7/2010 | ............. C07K 16/34 |

OTHER PUBLICATIONS

Janeway et al., Immunobilogy, 3rd edition, Garland Publishing Inc., 1997, pp. 3:1-3:11.*
Rudikoff et al., Proc Natl Acad Sci U S A. Mar. 1982;79(6):1979-83.*
Jaber et al., Blood. May 1, 1989;73(6):1597-602.*
PCT International Search Report and Written Opinion, International Application No. PCT/US2015/041416 dated Jan. 29, 2016, 8 pp.
Bosco et al., "An Autoanti-Kpb Immunoglobulin M that Simulates Antigen Suppression," Transfusion, Apr. 1, 2009, Vo. 49, pp. 750-756.
Zimring et al., "Transfusion-induced Autoantibodies and Differential Immunogenicity of Blood Group Antigens: a Novel Hypothesis," Transfusion, Dec. 1, 2007, vol. 47, pp. 2189-2196.
Boyland, et al., "Delayed hemolytic transfusion reaction caused by anti-Fyb in a splenectomized patient," Transfusion, vol. 22, No. 5, 1982, p. 402.
Campbell, et al., "Molecular cloning of the B-CAM cell surface glycoprotein of epithelial cancers: a novel member of the immunoglobulin superfamily," Cancer Res., vol. 54, No. 22, 1994, pp. 5761-5765.
Chaudhuri, et al., "Detection of Duffy antigen in the plasma membranes and caveolae of vascular endothelial and epithelial cells of nonerythroid organs," Blood, vol. 89, No. 2, 1997, pp. 701-712.
Daniels, et al., "Causes of fetal anemia in hemolytic disease due to anti-K," Transfusion, vol. 43, No. 1, 2003, pp. 115-116.
Daniels, et al., "International Society of Blood Transfusion Committee on Terminology for Red Cell Surface Antigens: Cape Town report," Vox Sanguinis, vol. 92, 2007, pp. 250-253.
Daniels, G. (2002). Kell and Kx blood group systems. In Human Blood Groups (2nd edn). pp. 295-323. Blackwell Science, Oxford.
Daniels, G. (2002). Lutheran blood group system. In Human Blood Groups (2nd edn). pp. 275-294. Blackwell Science, Oxford.
El Nemer, et al., "Organization of the human Lu gene and molecular basis of the Lu(a)/Lu(b) blood group polymorphism," Blood, vol. 89, No. 12, 1997, pp. 4608-4616.
Goodrick, et al., "Haemolytic disease of the fetus and newborn due to anti-Fy(a) and the potential clinical value of Duffy genotyping in pregnancies at risk," Transfusion Medicine, vol. 7, No. 4, 1997, pp. 301-304.

(Continued)

*Primary Examiner* — Michael Szperka
(74) *Attorney, Agent, or Firm* — Bloodworks; C. Rachal Winger; Thu Nguyen

(57) ABSTRACT

Compositions and methods of using antibodies that are able to recognize single amino acid polymorphisms in a protein are provided. Compositions are disclosed which may be used for blood typing or to block hemolytic transfusion reactions and/or hemolytic disease of the fetus and newborn.

15 Claims, 22 Drawing Sheets

Specification includes a Sequence Listing.

(56) References Cited

OTHER PUBLICATIONS

Hendrickson, et al., "Recipient inflammation affects the frequency and magnitude of immunization to transfused red blood cells," Transfusion, vol. 46 No. 9, 2006, pp. 1526-1536.

Inderbitzen, et al., "An example of HDN probably due to anti-Lua," Transfusion, vol. 22, No. 6, 1982, p. 542.

Iwamoto, et al., "Genomic organization of the glycoprotein D gene: Duffy blood group Fya/Fyb alloantigen system is associated with a polymorphism at the 44-amino acid residue," Blood, vol. 18, No. 3, 1995, pp. 622-626.

Iwamoto, et al., "Identification of a novel exon and spliced form of Duffy mRNA that is the predominant transcript in both erythroid and postcapillary venule endothelium," Blood, vol. 81, No. 1, 1996, pp. 378-385.

Lee, "Molecular basis of Kell blood group phenotypes," Vox Sanguinis, vol. 73, No. 1, 1997, pp. 1-11.

Mallinson, et al., "Mutations in the erythrocyte chemokine receptor (Duffy) gene: the molecular basis of the Fya/Fyb antigens and identification of a deletion in the Duffy gene of an apparently healthy individual with the Fy(a-b-) phenotype," Br. J. Haematol., vol. 90, No. 4, 1995, pp. 823-882.

Parsons, et al., "The Lutheran blood group glycoprotein, another member of the immunoglobulin superfamily, is widely expressed in human tissues and is developmentally regulated in human liver," PNAS, vol. 92, No. 12, 1995, pp. 5496-5500.

Reid, M. & Lomas-Francis, C. (2004). Lutheran blood group system. In the Blood Group Antigens FactsBook (2nd edn). pp. 193-224. Academic Press, London.

Ridgwell, et al., "Production of soluble recombinant proteins with Kell, Duffy and Lutheran blood group antigen activity, and their use in screening human sera for Kell, Duffy and Lutheran antibodies," Transfus. Med., vol. 17, No. 5, 2007, pp. 384-394.

Sosler, et al., "The prevalence of immunization to Duffy antigens in a population of known racial distribution," Transfusion, vol. 29, No. 6, 1989, pp. 505-507.

Tournamille, et al., "Molecular basis and PCR-DNA typing of the Fya/fyb blood group polymorphism," Human Genetics, vol. 95, No. 4, 1995, pp. 407-410.

Vaughan, et al., "Inhibition of erythroid progenitor cells by anti-Kell antibodies in fetal alloimmune anemia," New England Journal of Medicine, vol. 338, No. 12, 1998, pp. 798-803.

Vescio, et al., "Hemolytic disease of the newborn caused by anti-Fyb," Transfusion, vol. 27, No. 4, 1987, p. 366.

\* cited by examiner

Heavy chain sequence of Puma1 and Puma2

Sequence G

EVQLQQSGPELVKPGASVKMSCKASGYTFTDYYMKWVKQSHGKSLEWIGDLNPNNGDTFYNQKFKGKATLTVDKSSS
TAVYIQLNSLTSEDSAVYYCAREAGSFGSSCNYWGQGTTLTVS (SEQ ID NO: 1)

Or:

```
142  aagtcctctccacagactgacacactgactccaaccatggga
     M  S  S  P  Q  T  L  N  T  L  T  P  T  M  G
187  tggagctgatctttctctccttgtcaggaactggaggtgtc
     W  S  W  I  F  L  F  L  S  G  T  G  G  V
232  ctctctgaggtccaactgcaacagtctggacctgagctggtgaag
     L  S  E  V  Q  L  Q  Q  S  G  P  E  L  V  K
277  cctggggcttcagtgaag  tcctgcaagcttctggatacacc
     P  G  A  S  V  K   S  C  K  A  S  G  Y  T
322  ttcactgactactac  aagtggtgaacaagccatggaag
     F  T  D  Y  Y   K  W  M  V  K  Q  S  H  G  K
367  agccttgagtggattggagatcttaatcctaacaatggtgatact
     S  L  E  W  I  G  D  L  N  P  N  N  G  D  T
412  ttctacaaccagaagttcaaggcaaggccacattgactgtagat
     F  Y  N  Q  K  F  K  G  K  A  T  L  T  V  D
457  aagtcctccacagcacagtctacatccagctcaactcaagctct
     K  S  S  S  T  A  V  Y  I  Q  L  N  S  L  T  S
502  gaggactctgcagtctattactgtgcaagagaggcgggaagttcc
     E  D  S  A  V  Y  Y  C  A  R  E  A  G  S  S
547  ttcggtagtagctgtaattatgggccaaggcaccactcttcaca
     F  G  S  S  C  N  Y  W  G  Q  G  T  T  L  T
592  gtctcctcagccaaaacgggcccatctgtctatccactggcc
     V  S  S  A  K  T  T  A  P  S  V  Y  P  L  A
637  aatcgaattcccgcggccgcactgggcggccggagcagcgacgt
     N  R  I  P  A  A  A  M  A  A  G  S  M  R  R
682  cgggcccaattcgccctatag 702 (SEQ ID NO: 2)
     R  A  Q  F  A  L  *   (SEQ ID NO: 3)
``` ccatctgtctatccactgcc (SEQ ID NO: 4) matches reverse
complement DNA sequence of 3' primer for heavy chain

FIG. 1

Light chain sequence of Puma1 and Puma2

Sequence B
SVVMTQTPKFLLVSAGDRVTITCKASQTVSKDVAWYQQKPGQSPKLLIYYASNRYIGVPDRFTGSGYGTDFTFTISTVQ
AEDLAVYFCQQDYSSPYTFGGGTKLEIK (SEQ ID NO: 5)

Or:

```
778 atgaagtcacagaccaggtcttcgtattctactgtctgtgtg
    M  K  S  Q  T  Q  V  F  V  F  L  L  L  C  V
733 tctggagttcatgggagttgttgtcaccagactcccaagttc
    S  G  V  H  G  S  V  V  V  M  T  Q  T  P  K  F
688 ctgctgtgtctagctggagacagggtcaccataacctgcaaggcc
    L  L  V  S  A  G  D  R  V  T  I  T  C  K  A
643 agtcagactgtgagtaagatgtagctggtaccaacagaagcca
    S  Q  T  V  S  K  D  V  A  W  Y  Q  Q  K  P
598 gggcagtctcctaaactgctgatatactatgcatccaatcgctac
    G  Q  S  P  K  L  L  I  Y  Y  A  S  N  R  Y
553 actggagtccctgatcgcttcactggcagtggatatgggaccgat
    T  G  V  P  D  R  F  T  G  S  G  Y  G  T  D
508 ttcactttcaccatcagcactgtgcaggctgaagacctggcagtt
    F  T  F  T  I  S  T  V  Q  A  E  D  L  A  V
463 tatttctgtcagcaggattatagctccccgtacacgttcggagggg
    Y  F  C  Q  Q  D  Y  S  S  P  Y  T  F  G  G
418 gggaccaagctggaaataaaacggcctgatgctgcaccaactgta
    G  T  K  L  E  I  K  R  A  D  A  A  P  T  V
373 tccatcttcccaccatccagtgagcagttaacatctggaggtgcc
    S  I  F  P  P  S  S  E  Q  L  T  S  G  G  A
328 tcagtcgtgtgcttcttgaacaacttctaccccagagacatcaat
    S  V  V  C  F  L  N  N  F  Y  P  R  D  I  N
283 gtcaagtggaagattgatggcagtgaacgacaaaatggtgtcctg
    V  K  W  K  I  D  G  S  E  R  Q  N  G  V  L
238 aacagttgactgatcaggacagcaaagacagcacctacagcatg
    N  S  W  T  D  Q  D  S  K  D  S  T  Y  S  M
193 agcagcaccctcacattgaccaaggacgagtatgaacgacataac
    S  S  T  L  T  L  T  K  D  E  Y  E  R  H  N
148 agctataccctgagcctcacaagacatcacctcacccatc
    S  Y  T  C  E  A  T  H  K  T  S  T  S  P  I
103 gtcaagagcttcaacaggaatagtaatcactag 68  (SEQ ID NO: 6)
    V  K  S  F  N  R  N  X  C  N  H  *  (SEQ ID NO: 7)
```

FIG. 2

Heavy chain sequence of Puma3

Sequence F

QVQLKESGPGLLAPSQSLSITCTVSGFSLTSYGVYWVRQPPGKGLEWLGIIWGDGSTNYQSVLRSRLSITKDDSKSQVFL
KLNSLQTDDTATYYCAK*AGDYDVAYW*GQGTLVTVSA (SEQ ID NO: 8)

```
Or:  518 atggctgtcctggcactgctcctgctgacattcccaagg
          M  A  V  L  A  L  L  L  C  L  V  T  F  P  P  R
     473 tgtgtcctgtcccaggtgcagctgaaggagtcaggacctggccta
          C  V  L  S  Q  V  Q  L  K  E  S  G  P  G
     428 ctggcgccctcacagagcctgtccatcacatgcactgtctcaggt
          L  A  P  S  Q  S  L  S  I  T  C  T  V  S  G
     383 ttctcgttaaccagctatggtgtatactggttcgccagctcca
          F  S  L  T  S  Y  G  V  Y  W  V  R  Q  P  P
     338 ggaaagggtctggagtggctggaatcatatggggttgacgggagc
          G  K  G  L  E  W  L  G  I  I  W  G  D  G  S
     293 acaaatatcaatcagttctcagatcgagactgagcatcaccaag
          T  N  Y  Q  S  V  L  R  S  R  L  S  I  T  K
     248 gatgactccaagagccaagttttcttaaaactgaacagtctacaa
          D  D  S  K  S  Q  V  F  L  K  L  N  S  L  Q
     203 actgatgacacagccacgtactactgtgccaaacgaggggattac
          T  D  D  T  A  T  Y  Y  C  A  K  R  G  D  Y
     158 gacgttgcttactgggccaaggactggggtcactgtctctgca
          D  V  A  Y  W  G  Q  G  T  L  V  T  V  S  A
     113 gccaaaacgacacccccatctgtctatccttnagncaatcactag 69 (SEQ ID NO: 9)
          A  K  T  T  P  P  S  V  Y  P  X  X  N  H  * (SEQ ID NO: 10)
``` ccatctgtctat (SEQ ID NO: 11): reverse complement
DNA sequence of 3' primer for heavy

FIG. 3

Light chain sequence of Puma3

Sequence C

DIVLTQSPASLAVSLGQRAIISCKASQTVSFVGTSLMHWYQQRPGQQPKLLIYRTSNLEAGVPTRFSGSGSRTDFTLNIH
PVEEDDAATYYCQQSREFPWTFGGGTRLEIK (SEQ ID NO: 12)

```
Or:  59 atggnqactcantcnctgctgctnnngtgctactgctctgggtt
            M  X  T  X  S  L  L  X  V  L  L  L  W  V
    104 ccaggctccactggtgcattgtgctgacccaatctccagcttct
            P  G  S  T  G  D  I  V  L  T  Q  S  P  A  S
    149 ttggctgtgtctctcaggacaggagcatcatctgtcaaggcc
            L  A  V  S  L  G  Q  R  A  T  I  S  C  X  A
    194 agccaaactgtcagttcgtcggqattagtttacactggtat
            S  Q  T  V  S  F  V  G  T  S  L  M  H  W  Y
    239 caacagagaccaggacagcaaccaaactcctaatctatcgtaca
            Q  Q  R  P  G  Q  Q  P  K  L  L  I  Y  R  T
    284 tccaaccagaagcaggqttccaacagqttatggagcagtggg
            S  N  L  E  A  G  V  P  T  R  F  S  G  S  G
    329 tctaggacagactcacctcaatactccattctgaggaagat
            S  R  T  D  F  T  L  N  I  H  P  V  E  E  D
    374 gatgctgcaacctattactgtcagcaaagtaggaatttccqtq
            D  A  A  T  Y  Y  C  Q  Q  S  R  F  P  W
    419 acgttcggtcgqggagqcaccaaggctgqaaatcaaacggctgatgct
            T  F  G  G  G  T  R  L  E  I  K  R  A  D  A
    464 gcaccaactgtatccatcttcccaccatccagtgagcagttaaca
            A  P  T  V  S  I  F  P  P  S  S  E  Q  L  T
    509 tctggaggtgctcagtcgtgtgcttctgaacaacttctacccc
            S  G  G  A  S  V  V  C  F  L  N  N  F  Y  P
    554 agagacatcaatgtcaagtggaagattgatggcagtgaacgacaa
            R  D  I  N  V  K  W  K  I  D  G  S  E  R  Q
    599 aatggtgtcctgaacagttggactgatcaggacagcaaagacagc
            N  G  V  L  N  S  W  T  D  Q  D  S  K  D  S
    644 acctacagcatgagcagcaccctcacattgaccaaggacgagtat
            T  Y  S  M  S  S  T  L  T  L  T  K  D  E  Y
    689 gaacgacataacagctatacctgtgaggccactcacaagacatca
            E  R  H  N  S  Y  T  C  E  A  T  X  K  T  S
    734 acttcacccatcgtcaagagcttcaacaggaatgtgtaatcac
            T  S  P  I  V  K  S  F  N  R  N  E  C  N  H
    779 tag 781 (SEQ ID NO: 13)
    * (SEQ ID NO: 14)
```

FIG. 4

Heavy chain sequence of Puma 4

Sequence I

EVKLEESGGGLVQPGGSMKLSCVASGFTFSNYWMNWVRQPPEKGLEWVAEIRLNSNNYATHYAESVKGKFTISRDDS
KSSVYLQMNDLRAEDTGIYYCTR*WDEAW*FDSWGQGTLVTVSA (SEQ ID NO: 15)

```
Or: 122 atgggagacgcacaaccctgactcacaagtctttctcttcagt
            M  G  R  R  T  L  D  S  Q  V  F  L  F  S
    167 gacaaacacagaaatagaacattcaccatactttgggactgaac
            D  K  H  N  R  T  F  T  M  Y  L  G  L  N
    212 tgtgtattcatagttttctcttaaaaggtgtccagagtgaagtg
            C  V  F  I  V  F  L  K  G  V  Q  S  E  V
    257 aagcttgaggagtctgggaggcttggtgcaacctgggatcc
            K  L  E  E  S  G  G  G  L  V  Q  P  G  S
    302 tctctcctgtgttgctctggattcactttcagtaactac
            S  L  S  C  V  A  S  G  F  T  F  S  N  Y
    347 tgg   aactggtccgcaccaacctccagagacaaggggcttgaatgg
            W  M  N  W  V  R  Q  P  P  E  R  G  L  E  W
    392 gttgctgaattagattgaactctaataattatgcaacacattat
            V  A  E  I  R  L  N  S  N  N  Y  A  T  H  Y
    437 gcggaagtctgtgaaaggaaattcaccatctcaagagatgattcc
            A  E  S  V  K  G  K  F  T  I  S  R  D  D  S
    482 aaaagtagtgtctatactgcaa   aacgactaagagctgaagac
            K  S  S  V  Y  L  Q       N  D  L  R  A  E  D
    527 actggaattatactgaccagaaactggggcttttgctgttt
            T  G  I  Y  Y  C  T  R  N  W  D  F  A  W  F
    572 gattcctggggccaaggactctggtcactgtctctgcagccaaa
            D  S  W  G  Q  G  T  L  V  T  V  S  A  K
    617 acaacagcccatctgtctatccactggccaatcgaattcccgcg
            T  T  A  P  S  V  Y  P  L  A  N  R  I  P  A
    662 gccgccaagcggccgggagcatgcgacgtccggcccaattcgcc
            A  A  M  A  A  G  S  M  R  R  A  Q  F  A
    707 ctataag 712 (SEQ ID NO: 16)
            L  * (SEQ ID NO: 17)
``` ccatctgtctatccactggcc (SEQ ID NO: 4) here matches reverse complement DNA sequence of 3' primer for heavy chain

FIG. 5

Light chain sequence of Puma4

Sequence D

DIVMTQSHKFMSTSVGDRVSITCKASQDVSTYVAWYQQKPGQSPKLLIYWASTRHTGVPDRFTGSGSGTDYTLTISSV
QAEDLALYYCQQHYTTPFTFGSGTKLEIK (SEQ ID NO: 18)

```
Or: 811 atggggggaaatgcatcgcaccagcatggcatcaagatggagtca
            M  G  E  M  H  R  T  S  M  G  I  K  M  E  S
    766 cagattcaggcattgtgttcgtgttctctgttgtctggtgtt
            Q  I  Q  A  F  V  F  V  F  L  W  L  S  G  V
    721 gacggagacattgtgaaccagtctcacaaattcatgtccaca
            D  G  D  I  V  M  T  Q  S  H  K  F  M  S  T
    676 tcagtggtggagacaggggtcagtcatcacctgcaaggcaagat
            S  V  G  D  R  V  S  I  T  C  K  A  S  Q  D
    631 gtgagtactgttgtggcctggtatcaacaaaaccaggccaatct
            V  S  T  Y  V  A  W  Y  Q  Q  K  P  G  Q  S
    586 cctaaactactgatttactgggcatccaccgcacactgagtc
            P  K  L  L  I  Y  W  A  S  T  R  H  T  G  V
    541 cctgatcgcttcacaggcagtggatctggacaagattacactttc
            P  D  R  F  T  G  S  G  S  G  T  D  Y  T  F
    496 accatcagcagtgtgcaggctgaagacctggcactttattactgt
            T  I  S  S  V  Q  A  E  D  L  A  L  Y  Y  C
    451 cagcaacattataccactccattcacgttcggctcggggacaaag
            Q  Q  H  Y  T  T  P  F  T  F  G  S  G  T  K
    406 ttggaaataaaacgggctgatgctgccccaactgtatccatcttc
            L  E  I  K  R  A  D  A  A  P  T  V  S  I  F
    361 ccaccatccagtgagcagttaacatctgagggtgcctcagtcgtg
            P  P  S  S  E  Q  L  T  S  G  G  A  S  V  V
    316 tgcttcttgaacaacttctaccccagagacatcaatgtcaagtgg
            C  F  L  N  N  F  Y  P  R  D  I  N  V  K  W
    271 aagattgatggcagtgaacgacaaaatggtgtcctgaacagttgg
            K  I  D  G  S  E  R  Q  N  G  V  L  N  S  W
    226 actgatcaggacagcaaagacagcacctacagcatgagcagcacc
            T  D  Q  D  S  K  D  S  T  Y  S  M  S  S  T
    181 ctcactattgaccaaggacaagcagtatgaacgacataacagtatacc
            L  T  L  T  K  D  E  Y  E  R  H  N  S  Y  T
    136 tgtgaggccactcagcaagacatcaacttcacccatcgtcaagagc
            C  E  A  T  H  K  T  S  T  S  P  I  V  K  S
     91 ttcaacaggaatgagtgtaatcactag 65 (SEQ ID NO: 19)
            F  N  R  N  E  C  N  H  *    (SEQ ID NO: 20)
```

FIG. 6

Human PUMA1 IgG constructs:

>PUMA1-hG1
MSSPQTLNTLTPTMGWSWIFLFLLSGTGGVLSEVQLQQSGPELVKPGASVKMSCKASGYTFTDYYMKWVKQSHG
KSLEWIGDLNPNNGDTFYNQKFKGKATLTVDKSSSTAYIQLNSLTSEDSAVYYCAREAGSSFGSSCNYWGQGTTLT
VSASTKGPSVFPLAPSSKSTSGGTAALGCLVKDYFPEPVTVSWNSGALTSGVHTFPAVLQSSGLYSLSSVVTVPSSSL
GTQTYICNVNHKPSNTKVDKKVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKAKGQPRE
PQVYTLPPSREEMTKNQVSLTCLVKGFYPSDIAVEWESNGQPENNYKTTPPVLDSDGSFFLYSKLTVDKSRWQQG
NVFSCSVMHEALHNHYTQKSLSLSPGK (SEQ ID NO: 21)

>PUMA1-hG2
MSSPQTLNTLTPTMGWSWIFLFLLSGTGGVLSEVQLQQSGPELVKPGASVKMSCKASGYTFTDYYMKWVKQSHG
KSLEWIGDLNPNNGDTFYNQKFKGKATLTVDKSSSTAYIQLNSLTSEDSAVYYCAREAGSSFGSSCNYWGQGTTLT
VSASTKGPSVFPLAPCSRSTSESTAALGCLVKDYFPEPVTVSWNSGALTSGVHTFPAVLQSSGLYSLSSVVTVPSSNF
GTQTYTCNVDHKPSNTKVDKTVERKCCVECPPCPAPPVAGPSVFLFPPKPKDTLMISRTPEVTCVVVDVSHEDPEV
QFNWYVDGVEVHNAKTKPREEQFNSTFRVVSVLTVVHQDWLNGKEYKCKVSNKGLPAPIEKTISKTKGQPREPQV
YTLPPSREEMTKNQVSLTCLVKGFYPSDIAVEWESNGQPENNYKTTPPMLDSDGSFFLYSKLTVDKSRWQQGNVF
SCSVMHEALHNHYTQKSLSLSPGK (SEQ ID NO: 22)

>PUMA1-hG3
MSSPQTLNTLTPTMGWSWIFLFLLSGTGGVLSEVQLQQSGPELVKPGASVKMSCKASGYTFTDYYMKWVKQSHG
KSLEWIGDLNPNNGDTFYNQKFKGKATLTVDKSSSTAYIQLNSLTSEDSAVYYCAREAGSSFGSSCNYWGQGTTLT
VSASTKGPSVFPLAPCSRSTSGGTAALGCLVKDYFPEPVTVSWNSGALTSGVHTFPAVLQSSGLYSLSSVVTVPSSSL
GTQTYTCNVNHKPSNTKVDKRVELKTPLGDTTHTCPRCPEPKSCDTPPPCPRCPEPKSCDTPPPCPRCPEPKSCDTP
PPCPRCPAPELLGGPSVFLFPPKPKDTLMISRTPEVTCVVVDVSHEDPEVQFKWYVDGVEVHNAKTKPREEQYNST
FRVVSVLTVLHQDWLNGKEYKCKVSNKALPAPIEKTISKTKGQPREPQVYTLPPSREEMTKNQVSLTCLVKGFYPSDI
AVEWESSGQPENNYNTTPPMLDSDGSFFLYSKLTVDKSRWQQGNIFSCSVMHEALHNRFTQKSLSLSPGK (SEQ ID NO: 23)

>PUMA1-hG4
MSSPQTLNTLTPTMGWSWIFLFLLSGTGGVLSEVQLQQSGPELVKPGASVKMSCKASGYTFTDYYMKWVKQSHG
KSLEWIGDLNPNNGDTFYNQKFKGKATLTVDKSSSTAYIQLNSLTSEDSAVYYCAREAGSSFGSSCNYWGQGTTLT
VSASTKGPSVFPLAPCSRSTSESTAALGCLVKDYFPEPVTVSWNSGALTSGVHTFPAVLQSSGLYSLSSVVTVPSSSLG
TKTYTCNVDHKPSNTKVDKRVESKYGPPCPSCPAPEFLGGPSVFLFPPKPKDTLMISRTPEVTCVVVDVSQEDPEVQ
FNWYVDGVEVHNAKTKPREEQFNSTYRVVSVLTVLHQDWLNGKEYKCKVSNKGLPSSIEKTISKAKGQPREPQVY
TLPPSQEEMTKNQVSLTCLVKGFYPSDIAVEWESNGQPENNYKTTPPVLDSDGSFFLYSRLTVDKSRWQEGNVFSC
SVMHEALHNHYTQKSLSLSPGK (SEQ ID NO: 24)

FIG. 16 A

```
CLUSTAL 2.1 multiple sequence alignment

PUMA1-hG1      MSSPQTLNTLTPTMGWSWIFLFLLSGTGGVLSEVQLQQSGPELVKPGASVKMSCKASGYT 60
PUMA1-hG2      MSSPQTLNTLTPTMGWSWIFLFLLSGTGGVLSEVQLQQSGPELVKPGASVKMSCKASGYT 60
PUMA1-hG3      MSSPQTLNTLTPTMGWSWIFLFLLSGTGGVLSEVQLQQSGPELVKPGASVKMSCKASGYT 60
PUMA1-hG4      MSSPQTLNTLTPTMGWSWIFLFLLSGTGGVLSEVQLQQSGPELVKPGASVKMSCKASGYT 60
               ************************************************************

PUMA1-hG1      FTDYYMKWVKQSHGKSLEWIGDLNPNNGDTFYNQKFKGKATLTVDKSSSTAYIQLNSLTS 120
PUMA1-hG2      FTDYYMKWVKQSHGKSLEWIGDLNPNNGDTFYNQKFKGKATLTVDKSSSTAYIQLNSLTS 120
PUMA1-hG3      FTDYYMKWVKQSHGKSLEWIGDLNPNNGDTFYNQKFKGKATLTVDKSSSTAYIQLNSLTS 120
PUMA1-hG4      FTDYYMKWVKQSHGKSLEWIGDLNPNNGDTFYNQKFKGKATLTVDKSSSTAYIQLNSLTS 120
               ************************************************************

PUMA1-hG1      EDSAVYYCAREAGSSFGSSCNYWGQGTTLTVSASTKGPSVFPLAPSSKSTSGGTAALGCL 180
PUMA1-hG2      EDSAVYYCAREAGSSFGSSCNYWGQGTTLTVSASTKGPSVFPLAPCSRSTSESTAALGCL 180
PUMA1-hG3      EDSAVYYCAREAGSSFGSSCNYWGQGTTLTVSASTKGPSVFPLAPCSRSTSGGTAALGCL 180
PUMA1-hG4      EDSAVYYCAREAGSSFGSSCNYWGQGTTLTVSASTKGPSVFPLAPCSRSTSESTAALGCL 180
               ********************************************* *** *******

PUMA1-hG1      VKDYFPEPVTVSWNSGALTSGVHTFPAVLQSSGLYSLSSVVTVPSSSLGTQTYICNVNHK 240
PUMA1-hG2      VKDYFPEPVTVSWNSGALTSGVHTFPAVLQSSGLYSLSSVVTVPSSNFGTQTYTCNVDHK 240
PUMA1-hG3      VKDYFPEPVTVSWNSGALTSGVHTFPAVLQSSGLYSLSSVVTVPSSSLGTQTYTCNVNHK 240
PUMA1-hG4      VKDYFPEPVTVSWNSGALTSGVHTFPAVLQSSGLYSLSSVVTVPSSSLGTKTYTCNVDHK 240
               ********************************************** ** ** *** **

PUMA1-hG1      PSNTKVDKKVEPK---SCDKTHT--------------------------------- 260
PUMA1-hG2      PSNTKVDKTVE-------RKCCVE-------------------------------- 257
PUMA1-hG3      PSNTKVDKRVELKTPLGDTTHTCPRCPEPKSCDTPPPCPRCPEPKSCDTPPPCPRCPEPK 300
PUMA1-hG4      PSNTKVDKRVE------SKYGPP-------------------------------- 257
               ******** **

PUMA1-hG1      --------CPPCPAPELLGGPSVFLFPPKPKDTLMISRTPEVTCVVVDVSHEDPEVKFNWY 313
PUMA1-hG2      --------CPPCPAPPV-AGPSVFLFPPKPKDTLMISRTPEVTCVVVDVSHEDPEVQFNWY 309
PUMA1-hG3      SCDTPPPCPRCPAPELLGGPSVFLFPPKPKDTLMISRTPEVTCVVVDVSHEDPEVQFKWY 360
PUMA1-hG4      --------CPSCPAPEFLGGPSVFLFPPKPKDTLMISRTPEVTCVVVDVSQEDPEVQFNWY 310
                       ** ****  ******************************* ***** * **

PUMA1-hG1      VDGVEVHNAKTKPREEQYNSTYRVVSVLTVLHQDWLNGKEYKCKVSNKALPAPIEKTISK 373
PUMA1-hG2      VDGVEVHNAKTKPREEQFNSTFRVVSVLTVVHQDWLNGKEYKCKVSNKGLPAPIEKTISK 369
PUMA1-hG3      VDGVEVHNAKTKPREEQYNSTFRVVSVLTVLHQDWLNGKEYKCKVSNKALPAPIEKTISK 420
PUMA1-hG4      VDGVEVHNAKTKPREEQFNSTYRVVSVLTVLHQDWLNGKEYKCKVSNKGLPSSIEKTISK 370
               ***************** *** ********:********************* ** *******

PUMA1-hG1      AKGQPREPQVYTLPPSREEMTKNQVSLTCLVKGFYPSDIAVEWESNGQPENNYKTTPPVL 433
PUMA1-hG2      TKGQPREPQVYTLPPSREEMTKNQVSLTCLVKGFYPSDIAVEWESNGQPENNYKTTPPML 429
PUMA1-hG3      TKGQPREPQVYTLPPSREEMTKNQVSLTCLVKGFYPSDIAVEWESSGQPENNYNTTPPML 480
PUMA1-hG4      AKGQPREPQVYTLPPSQEEMTKNQVSLTCLVKGFYPSDIAVEWESNGQPENNYKTTPPVL 430
                **************** ************************** ******** **** *

PUMA1-hG1      DSDGSFFLYSKLTVDKSRWQQGNVFSCSVMHEALHNHYTQKSLSLSPGK 482 (SEQ ID NO: 21)
PUMA1-hG2      DSDGSFFLYSKLTVDKSRWQQGNVFSCSVMHEALHNHYTQKSLSLSPGK 478 (SEQ ID NO: 22)
PUMA1-hG3      DSDGSFFLYSKLTVDKSRWQQGNIFSCSVMHEALHNRFTQKSLSLSPGK 529 (SEQ ID NO: 23)
PUMA1-hG4      DSDGSFFLYSRLTVDKSRWQEGNVFSCSVMHEALHNHYTQKSLSLSPGK 479 (SEQ ID NO: 24)
               ********** ********* ** *********** ***********
```

FIG. 16 B

Demonstration of successful humanization of PUMA1 to human IgG1, IgG2, IgG3, or IgG4 forms, with maintenance of binding of KEL+ R

US 10,253,109 B2

ANTIBODIES THAT RECOGNIZE RED BLOOD CELL ANTIGENS

CROSS-REFERENCE TO RELATED APPLICATIONS

This application claims priority to International Application No. PCT/US2015/041416, filed Jul. 21, 2015, which claims the benefit of priority to U.S. Provisional Patent Application No. 62/027,207, filed Jul. 21, 2014, and to U.S. Provisional Patent Application No. 62/120,248, filed Feb. 24, 2015, each of which is incorporated herein by reference in its entirety as if fully set forth herein.

STATEMENT REGARDING SEQUENCE LISTING

The Sequence Listing associated with this application is provided in text format in lieu of a paper copy, and is hereby incorporated by reference into the specification. The name of the text file containing the Sequence Listing is B212-0002US Sequence Listing_ST25.txt. The text file is 61 KB, created on Jun. 3, 2018, and is being submitted electronically via EFS-Web.

FIELD

The invention relates to compositions and methods related to antibodies that recognize red blood cell antigens. In particular, the antibodies of the invention recognize single amino acid polymorphisms in a protein, such as those that occur on cell surface antigens on red blood cells, for example, the human Kell glycoproteins. The antibodies of the present invention can be used for diagnostic or therapeutic uses.

BACKGROUND

Transfusion is a life-saving therapy, given to a large number of patients for a wide variety of medical indications. In the United States of America alone, approximately 5 million patients (i.e. 1 out of every 70 Americans) are transfused with red blood cells (RBCs) each year. In addition to the well-known ABO and RhD blood group antigen systems, there are in excess of 300 known RBC antigens that vary from person to person. Thus, any non-autologous transfusion represents an exposure to a multiplicity of antigenic differences. The immune system of some transfusion recipients will react to the foreign alloantigens and generate alloantibodies. Once a patient has an antibody against an RBC alloantigen, then they are designated "incompatible" with donor RBCs that express that antigen.

Transfusion of incompatible blood is avoided, because the antibodies can destroy the transfused RBCs. The major problem is not just that destroying the RBCs obviates the potential therapeutic effect, but more importantly, the process of RBC destruction by recipient antibodies can be a profound toxic insult to the recipient, leading to myriad pathological outcomes, including: electrolyte disturbance, hemodynamic dysregulation and instability, kidney failure, coagulopathy, and death in extreme cases. In aggregate, these pathologies are referred to as a hemolytic transfusion reaction (HTR). Avoiding HTRs is the primary goal of blood banks around the world, and represents an entire field of immunohematology (e.g. characterizing patient alloantibodies as they evolve with each transfusion, and providing compatible RBCs not recognized by a patient's antibodies).

The majority of transfused patients are typically being treated for an injury or transient illness, from which they subsequently recover, and no longer require transfusion. In such patients, avoiding incompatible transfusion is an issue of blood bank logistics, and sufficient RBCs can be provided to such patients by monitoring the antibody response as it evolves and identifying/acquiring units of RBCs lacking the antigens to which the patients have alloantibodies. However, a subset of patients require chronic transfusion therapy, in some cases for the remainder of their lives. For example, genetic abnormalities in RBC production (mostly hemoglobinopatheis) lead to lifelong needs for RBC transfusion support (e.g. Sickle cell disease (SCD), alpha and beta thallesemia, Diamond Blackfan anemia, Faconi anemia, etc). As an example, patients with SCD often have weekly prophylactic transfusions, exposing them to a panoply of different antigens. Up to 50% of SCD patients become alloimmunized to at least one alloantigen, and once a patient becomes immunized to one alloantigen, they are more likely to become immunized to additional antigens. Rates of alloimmunization can be mitigated by prematching to select matched blood group antigens (e.g. Kell, Kidd, Duffy, and others), however such pre-matching is often not feasible and is very costly. In addition, the matching process can delay the delivery of blood, which may have significant negative consequences if the patient is being treated for a clinical crisis episode.

The more antigens against which a given patient becomes alloimmunized, the more difficult it becomes to find a sufficient number of compatible RBC transfusions to meet the patient's clinical needs. In some cases, compatible RBCs do not become available quickly enough to properly care for the patient, and in extreme cases, alloimmunized patients may die for wont of sufficient compatible RBCs.

A second disease that can result from patient alloimunization against RBC antigens is hemolytic disease of the fetus and newborn (HDFN). In this case, a pregnant mother has alloantibodies against an antigen expressed by a fetus she is carrying in her womb. The antibodies can cross the placenta, and destroy fetal RBCs, resulting in fetal anemia, maldevelopment, and in serve cases, death. In HDFN, the mother herself does not become anemic, as the alloantigen in question is not on her own RBCs, but only on those of the fetus. The frequency of HDFN has decreased with the use of anti-D Ig, however alloimmunization still occurs against RhD. Moreover, there is no prophylaxis currently available for antigens such as Kell, Kidd, Duffy etc. Once a woman is alloimmunized and pregnant with an antigen positive fetus, the primary treatment is intrauterine transfusions with RBC negative blood and symptomatic treatment.

The inability of current technologies to provide sufficient units of compatible RBCs for alloimmunized patients, resulting in morbidity and mortality due to lack of compatible blood, is a primary medical need addressed by the current disclosure. A secondary application of the present disclosure is for the treatment of pregnant women whose fetuses are suffering HDFN.

SUMMARY

Described herein are compositions and methods related to monoclonal antibodies capable of distinguishing single amino acid determinants on an antigen, in particular, antigens found on the surfaces of red blood cells. Such antibodies can be used for diagnostic applications such as RBC typing. In other embodiments, the compositions and methods disclosed herein can be used therapeutically, such as to block hemolytic transfusion reactions.

In a first aspect, disclosed herein is an isolated antibody or fragment thereof that binds to a red blood cell surface antigen and blocks a hemolytic transfusion reaction.

In various embodiments of this aspect, the antibody recognizes the epitope created by a single amino acid polymorphism.

In other embodiments of this aspect, the epitope/antigen is a member of the Kell blood group antigen system, for example, KEL1, KEL2, KEL3, KEL4, KEL5, KEL6, or KEL7. In particular embodiments, the Kell blood group antigen is K, $Kp^b$, or $Js^b$.

In further embodiments of this aspect, the antibody or fragment thereof comprises a heavy chain comprising at least one CDR selected from the group of CDR sequences shown in FIG. 1.

In yet further embodiments of this aspect, the antibody or fragment thereof comprises a light chain comprising at least one CDR selected from the group of CDR sequences shown in FIG. 2.

In other embodiments of this aspect, the antibody or fragment thereof comprises a heavy chain comprising one, two, or three CDR(s) selected from the group of CDR sequences shown in FIG. 1.

In other embodiments of this aspect, the antibody or fragment thereof comprises a light chain comprising one, two, or three CDR(s) selected from the group of CDR sequences shown in FIG. 2.

In other embodiments of this aspect, the antibody or fragment thereof comprises a heavy chain comprising at least a portion of the sequence shown in FIG. 1.

In other embodiments of this aspect, the antibody or fragment thereof comprises a light chain comprising at least a portion of the sequence shown in FIG. 2.

In other embodiments of this aspect, the antibody or fragment thereof is selected from the group consisting of: (a) a whole immunoglobulin molecule; (b) an scFv; (c) a Fab fragment; (d) an F(ab')2; and (e) a disulfide linked Fv.

In various of the above aspects and embodiments, the antibody or fragment comprises a heavy chain immunoglobulin constant domain selected from the group consisting of: (a) a human IgM constant domain; (b) a human IgG1 constant domain; (c) a human IgG2 constant domain; (d) a human IgG3 constant domain; (e) a human IgG4 constant domain; and (f) a human IgA1/2 constant domain.

In various of the above aspects and embodiments, the antibody or fragment thereof comprises a light chain immunoglobulin constant domain selected from the group consisting of: (a) a human Ig kappa constant domain; and (b) a human Ig lambda constant domain.

In various of the above aspects and embodiments, the antibody or fragment thereof is a mouse IgG1, IgG2a, IgG2b, IgG2c, or IgG3.

In various of the above aspects and embodiments, the antibody or fragment thereof comprises mutations in the constant region. Examples of such mutations include, but are not limited to, mutations in the constant region that alter binding to Fc Receptors, alter fixation of complement, or alter the ability to cross the placenta into fetal circulation.

In various of the above aspects and embodiments, the antibody or fragment thereof comprises alterations in glycosyslation of the antibody or fragment thereof. Examples of such alterations in glycosyslation include, but are not limited to, alterations in fucosylation, sialylation, or modification of GlcNAC, glucose, or galactose.

In various of the above aspects and embodiments, the antibody or fragment thereof binds to an antigen with an affinity constant ($K_D$) of less than $1\times10^{-8}$ M.

In various of the above aspects and embodiments, the antibody or fragment thereof binds to an antigen with an affinity constant ($K_D$) of less than $1\times10^{-9}$ M.

In a second aspect, disclosed herein is a method of preventing or reducing a hemolytic transfusion reaction by administering a therapeutically effective amount of the antibody or fragment thereof disclosed above to a subject in need thereof prior to a transfusion with red blood cells. In some embodiments, the antibody or fragment is administered to the subject prior to the transfusion. In other embodiments, the red blood cells for transfusion are treated with the antibody or fragment thereof prior to transfusion into the subject. In some embodiments, the antibody or fragment thereof is administered intravenously (IV), subcutaneously (SC), or intramuscularly (IM). In some embodiments, the antibody or fragment thereof is administered in an amount in the range of 1 to 100 milligrams per kilogram of the subject's body weight.

In a related aspect, disclosed herein is a method of treating, preventing, or reducing a hemolytic transfusion reaction, the method comprising the steps of administering a therapeutically effective amount of an antibody or fragment thereof to a subject in need thereof prior to a transfusion with donor red blood cells, wherein said antibody or fragment thereof binds to a red blood cell antigen on the donor red blood cells to block the binding of a hemolytic antibody and wherein said antibody or fragment thereof does not itself cause destruction of donor red blood cells, thereby treating, preventing, or reducing a hemolytic transfusion reaction. In some embodiments, the antibody or fragment is administered to the subject prior to the transfusion. In other embodiments, the red blood cells for transfusion are treated with the antibody or fragment thereof prior to transfusion into the subject. In various embodiments of this aspect, the antibodies or fragments thereof disclosed above are used. In some embodiments, the antibody or fragment thereof is administered intravenously (IV), subcutaneously (SC), or intramuscularly (IM). In some embodiments, the antibody or fragment thereof is administered in an amount in the range of 1 to 100 milligrams per kilogram of the subject's body weight.

In a third aspect, disclosed herein is an expression vector comprising a nucleic acid encoding the antibody or fragment thereof disclosed above.

In some embodiments of this aspect, the expression vector is in a host cell, which can include a bacterial cell or a eukaryotic cell, such as a mammalian cell.

In a fourth aspect, disclosed herein is an antibody or fragment thereof comprises a heavy chain comprising at least one CDR selected from the group of CDR sequences shown in FIGS. 1, 3, and 5.

In a fifth aspect, disclosed herein is an antibody or fragment thereof comprises a light chain comprising at least one CDR selected from the group of CDR sequences shown in FIGS. 2, 4, and 6.

In a sixth aspect, disclosed herein is an antibody or fragment thereof comprises a heavy chain comprising one, two, or three CDR(s) selected from the group of CDR sequences shown in FIGS. 1, 3, and 5.

In a seventh aspect, disclosed herein is an antibody or fragment thereof comprises a light chain comprising one, two, or three CDR(s) selected from the group of CDR sequences shown in FIGS. 2, 4, and 6.

In an eighth aspect, disclosed herein is an antibody or fragment thereof comprises a heavy chain comprising the sequence shown in FIG. 1, FIG. 3, or FIG. 5.

In a ninth aspect, disclosed herein is an antibody or fragment thereof comprises a light chain comprising the sequence shown in FIG. 2, FIG. 4, or FIG. 6.

In a tenth aspect, disclosed herein is an antibody or fragment thereof comprises a heavy chain comprising the sequence of FIG. 1 and a light chain sequence of FIG. 2.

In a eleventh aspect, disclosed herein is an antibody or fragment thereof comprises a heavy chain comprising the sequence of FIG. 3 and a light chain sequence of FIG. 4.

In a twelfth aspect, disclosed herein is an antibody or fragment thereof comprises a heavy chain comprising the sequence of FIG. 5 and a light chain sequence of FIG. 6.

In some embodiments of these aspects, the antibody or fragment thereof is selected from the group consisting of: (a) a whole immunoglobulin molecule; (b) an scFv; (c) a Fab fragment; (d) an F(ab')2; and (e) a disulfide linked Fv.

In various of the above aspect and embodiments, the antibody or fragment comprises a heavy chain immunoglobulin constant domain selected from the group consisting of: (a) a human IgM constant domain; (b) a human IgG1 constant domain; (c) a human IgG2 constant domain; (d) a human IgG3 constant domain; (e) a human IgG4 constant domain; and (f) a human IgA1/2 constant domain.

In various of the above aspect and embodiments, the antibody or fragment thereof comprises a light chain immunoglobulin constant domain selected from the group consisting of: (a) a human Ig kappa constant domain; and (b) a human Ig lambda constant domain.

In various of the above aspect and embodiments, the antibody or fragment thereof is a mouse IgG1, IgG2a, IgG2b, IgG2c, or IgG3.

In various of the above aspect and embodiments, the antibody or fragment thereof comprises mutations in the constant region. Examples of such mutations include, but are not limited to, mutations in the constant region that alter binding to Fc Receptors, alter fixation of compliment, or alter the ability to cross the placenta into fetal circulation.

In various of the above aspect and embodiments, the antibody or fragment thereof comprises alterations in glycosyslation of the antibody or fragment thereof. Examples of such alterations in glycosyslation include, but are not limited to, alterations in fucosylation, sialylation, or modification of GlcNAC, glucose, or galactose.

In various of the above aspect and embodiments, the antibody or fragment thereof binds to an antigen with an affinity constant ($K_D$) of less than $1 \times 10^{-8}$ M.

In various of the above aspect and embodiments, the antibody or fragment thereof binds to an antigen with an affinity constant ($K_D$) of less than $1 \times 10^{-9}$ M.

In a thirteenth aspect, disclosed herein is a method of generating an antibody or fragment thereof that binds to a red blood cell surface antigen or fragment thereof, the method comprising the steps of: (a) generating mice expressing a human red blood cell surface antigen on its red blood cells; (b) immunizing wild type mice by transfusing red blood cells from the mice expressing the human red blood cell surface antigen on its red blood cells; and (c) using splenocytes from the immunized mice to generate monoclonal antibodies. In some embodiments of this aspect, the epitope/antigen is a member of the Kell blood group antigen system, for example, KEL1, KEL2, KEL3, KEL4, KEL5, KEL6, or KEL7. In particular embodiments, the Kell blood group antigen is KEL1 (K) or KEL4 ($Kp^b$).

In a fourteenth aspect, disclosed herein is an expression vector comprising any one of the nucleic acids shown in FIGS. 1-6.

In some embodiments of this aspect, the expression vector is in a host cell, which can include a bacterial cell or a eukaryotic cell, such as a mammalian cell.

BRIEF DESCRIPTION OF THE DRAWINGS

FIG. 1 shows the heavy chain sequence (SEQ ID NOs: 1, 2, and 3) of monoclonal antibodies Puma 1 and 2 directed to KEL1 (K). The shading indicates where the highly variable region begins. The CDR regions (CDR1: DYYMK, SEQ ID NO: 25; CDR2: DLNPNNGDTFYNQKFKG, SEQ ID NO: 26; and CDR3: CAREAGSSFGSSCNYWG, SEQ ID NO: 27) of the heavy chain are underlined.

FIG. 2 shows the light chain sequence (SEQ ID NOs: 5, 6, and 7) of monoclonal antibodies Puma 1 and 2 directed to KEL1 (K). The shading indicates where the highly variable region begins. The CDR regions (CDR1: KASQTVSKDVA, SEQ ID NO: 28; CDR2: YASNRYT, SEQ ID NO: 29; and CDR3: QQDYSS, SEQ ID NO: 30) of the light chain are underlined.

FIG. 3 shows the heavy chain sequence (SEQ ID NOs: 8, 9, and 10) of monoclonal antibody Puma 3 directed to a common Kell epitope. The shading indicates where the highly variable region begins. The CDR regions (CDR1: SYGVY, SEQ ID NO: 31; CDR2: IIWGDGSTNYQSVLRS, SEQ ID NO: 32; and CDR3: RGDYDVA, SEQ ID NO: 33) of the heavy chain are underlined.

FIG. 4 shows the light chain sequence (SEQ ID NOs: 12, 13, and 14) of monoclonal antibody Puma 3 directed to a common Kell epitope. The shading indicates where the highly variable region begins. The CDR regions (CDR1: KASQTVSEVGTSLMH, SEQ ID NO: 34; CDR2: RTSNLEA, SEQ ID NO: 35; and CDR3: QQS, SEQ ID NO: 36) of the light chain are underlined.

FIG. 5 shows the heavy chain sequence (SEQ ID NOs: 15, 16, and 17) of monoclonal antibody Puma 4 directed to KEL4 ($Kp^b$). The shading indicates where the highly variable region begins. The CDR regions (CDR1: NYWMN, SEQ ID NO: 37; CDR2: EIRLNSNNYATHYAESVKG, SEQ ID NO: 38; and CDR3: NWDFAW, SEQ ID NO: 39) of the heavy chain are underlined.

FIG. 6 shows the light chain sequence (SEQ ID NOs: 18, 19, and 20) of monoclonal antibody Puma 4 directed to KEL4 ($Kp^b$). The CDR regions (CDR1: KASQDVSTVVA, SEQ ID NO: 40; CDR2: WASTRHT, SEQ ID NO: 41; and CDR3: QQHYT, SEQ ID NO: 42) of the light chain are underlined.

FIGS. 16A, 16B show the sequences of humanization of PUMA1 to human IgG1, IgG2, IgG3, and IgG4 (FIG. 16A, SEQ ID NOs: 21-24) and the alignment of these sequences (FIG. 16B).

DETAILED DESCRIPTION

In one embodiment, the present disclosure describes the isolation of antibodies with sufficient fine specificity to recognize conformational changes brought about by single amino acid polymorphisms in a given protein. Such antibodies are difficult to isolate for a number of reasons. First, the antigens are typically transmembrane proteins with conformational requirements of being expressed on the cell surface, precluding isolation of large amounts of cell free antigen for immunization. Second, expression in cell lines typically results in the desired antigen, but also a great number of additional foreign antigens, which can dominate the immune response and limit antibodies of the desired specificity. The present invention provides methods and compostions that circumvent many of these limitations to provide new RBC typing reagents.

Figure 11:
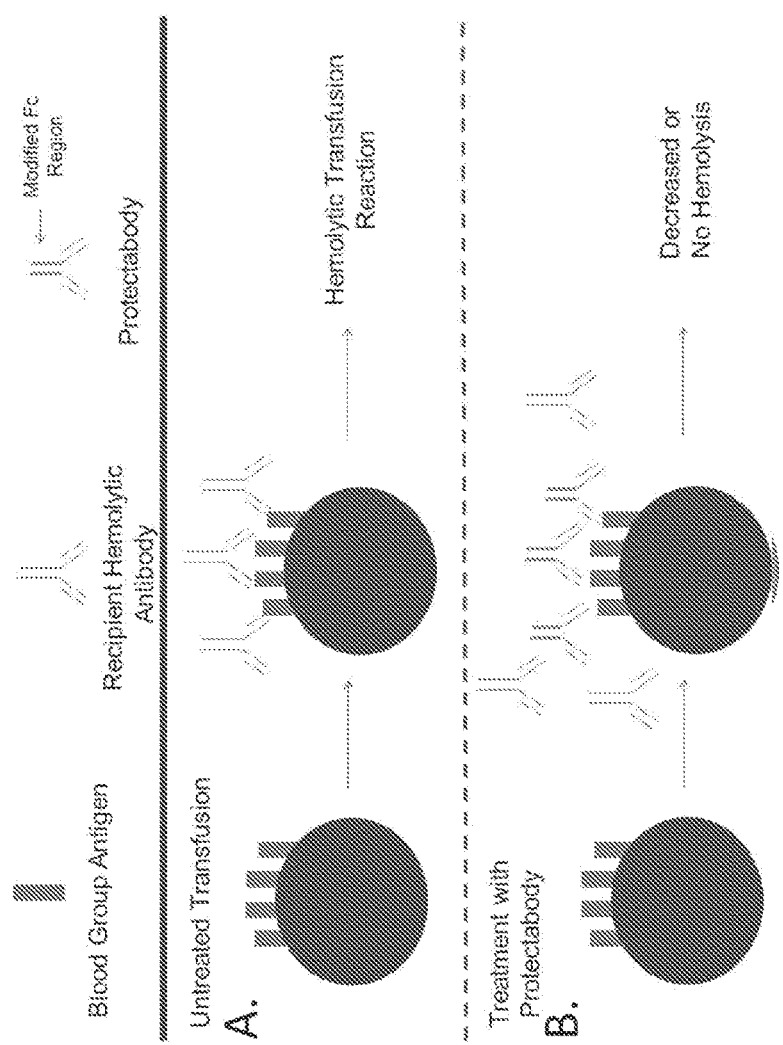
FIGS. 11A-11B shows an overview of protective antibody (protectabody) therapy.
Figure 12:
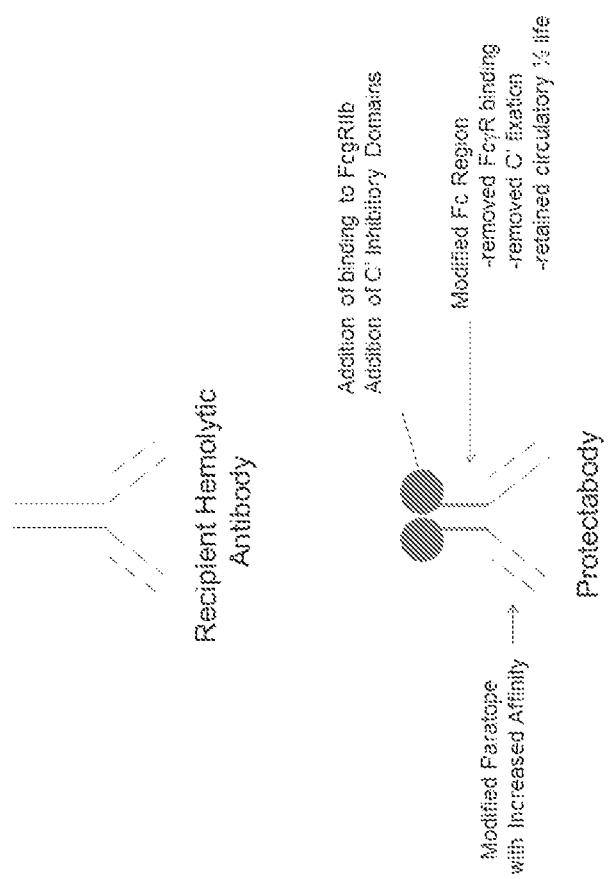
FIG. 12 shows potential modifications and features of protective antibody (protectabody) structure.

One principle behind the therapeutic application of the technology disclosed herein is the engineering of molecules that mask offending antigens on RBCs and thereby block recipient/maternal alloantibodies from binding to and destroying the RBCs. In the normal clinical situation of incompatible RBCs described above, an HTR occurs when recipient antibodies bind to donor RBC antigens, resulting in RBC destruction (FIG. 11A). The general concept is to engineer recombinant antibodies that bind to the antigen(s) in question but are modified such that their Fc region no longer binds to Fc receptors or complement (green bars, FIGS. 11A, 11B), thus rendering it "non-hemolytic" (FIG. 11B). Such an engineered antibody will bind to the same antigen recognized by hemolytic antibodies in the recipient and thus block the antigen with a non-hemolytic entity. In this way, the engineered antibody will prevent hemolysis of the RBCs and allow transfusion despite alloantibodies in the recipient, which would otherwise be hemolytic. The modified protective antibody (called protectabodies hereafter) will retain an Fc region to provide long circulatory half-life; however, modifications may include (but not be limited to), removing Fc Receptor binding of activating receptors, increasing binding to FcgRIIb (an inhibitory Fc receptor), removing complement binding, and adding complement inhibitory domains (FIG. 12).

It is to be understood that this invention is not limited to particular methods, reagents, compounds, compositions or biological systems, which can, of course, vary. It is also to be understood that the terminology used herein is for the purpose of describing particular aspects only, and is not intended to be limiting. As used in this specification and the appended claims, the singular forms "a", "an" and "the" include plural references unless the content clearly dictates otherwise.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein.

As used herein, the term "hemolytic transfusion reaction" refers generally to a complication that can occur after a transfusion of blood in which the red blood cells that were given in the transfusion are destroyed by the patient's immune system (antibodies to the donor RBCs). Symptoms of a hemolytic transfusion reaction may include: back pain, bloody urine, chills, fainting or dizziness, fever, flank pain, and flushing of the skin. In severe cases, hemolytic transfusion reactions can lead to organ failure, coagulation defects, and/or death.

As used herein, a "hemolytic antibody" is an antibody, typically a recipient or maternal alloantibody, that binds to a red blood cell antigen on donor red blood cells from a transfusion and causing destruction or hemolysis of the transfused donor red blood cells.

A "protective antibody" or "protectabody" refers generally to an antibody that will bind to an antigen recognized by a hemolytic antibody in a recipient, but will not cause red blood cell destruction or hemolysis. In this way, the protective antibody blocks the hemolytic antigen with a non-hemolytic entity. Generally, a protective antibody is modified to render it non-hemolytic as described herein. Such modifications may include: removing Fc Receptor binding of activating receptors, increasing binding to FcgRIIb (an inhibitory Fc receptor), removing complement binding, and adding complement inhibitory domains.

"Subject," "mammalian subject," or "patient" are used interchangeably and refer to mammals such as human patients and non-human primates, as well as experimental animals such as rabbits, rats, and mice, cows, horses, goats, and other animals. Animals include all vertebrates, e.g., mammals and non-mammals, such as mice, sheep, dogs, cows, avian species, ducks, geese, pigs, chickens, amphibians, and reptiles.

"Treating" or "treatment" refers generally to either (i) the prevention, e.g., prophylaxis, or (ii) the reduction or elimination of symptoms of a disease of interest, e.g., therapy. Treating a subject with the compositions of the invention can prevent or reduce the risk of the subject suffering from a hemolytic transfusion reaction (HTR). Treatment can be prophylactic (to prevent or delay the onset of the disease, or to prevent the manifestation of clinical or subclinical symptoms thereof) or therapeutic suppression or alleviation of symptoms after the manifestation of the disease.

"Preventing" or "prevention" refers to prophylactic administration with compositions of the invention.

"Therapeutically-effective amount" or "an amount effective to reduce the effects of a disease" or "an effective amount" refers to an amount of an antibody composition that is sufficient to prevent a hemolytic transfusion reaction or to alleviate (e.g., mitigate, decrease, reduce) at least one of the symptoms associated with this condition. It is not necessary that the administration of the composition eliminate the symptoms of a hemolytic transfusion reaction, as long as the benefits of administration of the composition outweigh the detriments. Likewise, the terms "treat" and "treating" in reference to a hemolytic transfusion reaction, as used herein, are not intended to mean that the subject is necessarily cured of the condition or that all clinical signs thereof are eliminated, only that some alleviation or improvement in the condition of the subject is effected by administration of the composition.

Polypeptides

The term "polypeptide" or "peptide" refers to a polymer of amino acids without regard to the length of the polymer; thus, peptides, oligopeptides, and proteins are included within the definition of polypeptide. This term also does not specify or exclude post-expression modifications of polypeptides, for example, polypeptides which include the covalent attachment of glycosyl groups, acetyl groups, phosphate groups, lipid groups and the like are expressly encompassed by the term polypeptide. Also included within the definition are polypeptides which contain one or more analogs of an amino acid (including, for example, non-naturally occurring amino acids, amino acids which only occur naturally in an unrelated biological system, modified amino acids from mammalian systems etc.), polypeptides with substituted linkages, as well as other modifications known in the art, both naturally occurring and non-naturally occurring.

The term "isolated protein," "isolated polypeptide," or "isolated peptide" is a protein, polypeptide or peptide that by virtue of its origin or source of derivation (1) is not associated with naturally associated components that accompany it in its native state, (2) is free of other proteins from the same species, (3) is expressed by a cell from a different species, or (4) does not occur in nature. Thus, a peptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The terms "polypeptide", "protein", "peptide," "antigen," or "antibody" within the meaning of the present invention, includes variants, analogs, orthologs, homologs and derivatives, and fragments thereof that exhibit a biological activity, generally in the context of being able to induce an immune response in a subject, or bind an antigen in the case of an antibody.

The polypeptides of the invention include an amino acid sequence derived from Kell system antigens or fragments thereof, corresponding to the amino acid sequence of a naturally occurring protein or corresponding to variant protein, i.e., the amino acid sequence of the naturally occurring protein in which a small number of amino acids have been substituted, added, or deleted but which retains essentially the same immunological properties. In addition, such derived portion can be further modified by amino acids, especially at the N- and C-terminal ends to allow the polypeptide or fragment to be conformationally constrained and/or to allow coupling to an immunogenic carrier after appropriate chemistry has been carried out. The polypeptides of the present invention encompass functionally active variant polypeptides derived from the amino acid sequence of Kell system antigens in which amino acids have been deleted, inserted, or substituted without essentially detracting from the immunological properties thereof, i.e. such functionally active variant polypeptides retain a substantial peptide biological activity.

In one embodiment, such functionally active variant polypeptides exhibit at least 60%, 65%, 70%, 75%, 80%, 81%, 82%, 83%, 84%, 85%, 86%, 87%, 88%, 89% 90%, 91%, 92%, 93%, 94%, 95%, 96%, 97%, 98%, or 99% identity to an amino acid sequence of the blood group antigens disclosed herein. Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson, Methods Enzymol. 183:63-98 (1990); Pearson, Methods Mol. Biol. 132:185-219 (2000)). An alternative algorithm when comparing a sequence of the invention to a database containing a large number of sequences from different organisms is the computer program BLAST, especially blastp or tblastn, using default parameters. See, e.g., Altschul et al., J. Mol. Biol. 215:403-410 (1990); Altschul et al., Nucleic Acids Res. 25:3389-402 (1997).

Functionally active variants comprise naturally occurring functionally active variants such as allelic variants and species variants and non-naturally occurring functionally active variants that can be produced by, for example, mutagenesis techniques or by direct synthesis.

A functionally active variant can exhibit, for example, at least 60%, 65%, 70%, 75%, 80%, 81%, 82%, 83%, 84%, 85%, 86%, 87%, 88%, 89% 90%, 91%, 92%, 93%, 94%, 95%, 96%, 97%, 98%, or 99% identity to an amino acid sequence of a Kell system or other antigen disclosed herein, and yet retain a biological activity. Where this comparison requires alignment, the sequences are aligned for maximum homology. The site of variation can occur anywhere in the sequence, as long as the biological activity is substantially similar to the Kell system or other antigens disclosed herein, e.g., ability to induce a tolerance reponse. Guidance concerning how to make phenotypically silent amino acid substitutions is provided in Bowie et al., Science, 247: 1306-1310 (1990), which teaches that there are two main strategies for studying the tolerance of an amino acid sequence to change. The first strategy exploits the tolerance of amino acid substitutions by natural selection during the process of evolution. By comparing amino acid sequences in different species, the amino acid positions which have been conserved between species can be identified. These conserved amino acids are likely important for protein function. In contrast, the amino acid positions in which substitutions have been tolerated by natural selection indicate positions which are not critical for protein function. Thus, positions tolerating amino acid substitution can be modified while still maintaining specific immunogenic activity of the modified polypeptide.

The second strategy uses genetic engineering to introduce amino acid changes at specific positions of a cloned gene to identify regions critical for protein function. For example, site-directed mutagenesis or alanine-scanning mutagenesis can be used (Cunningham et al., Science, 244: 1081-1085 (1989)). The resulting variant polypeptides can then be tested for specific biological activity.

According to Bowie et al., these two strategies have revealed that proteins are surprisingly tolerant of amino acid substitutions. The authors further indicate which amino acid changes are likely to be permissive at certain amino acid positions in the protein. For example, the most buried or interior (within the tertiary structure of the protein) amino acid residues require nonpolar side chains, whereas few features of surface or exterior side chains are generally conserved.

Methods of introducing a mutation into amino acids of a protein is well known to those skilled in the art. (See, e.g., Ausubel (ed.), Current Protocols in Molecular Biology, John Wiley and Sons, Inc. (1994); T. Maniatis, E. F. Fritsch and J. Sambrook, Molecular Cloning: A Laboratory Manual, Cold Spring Harbor laboratory, Cold Spring Harbor, N.Y. (1989)).

Mutations can also be introduced using commercially available kits such as "QuikChange Site-Directed Mutagenesis Kit" (Stratagene) or directly by peptide synthesis. The generation of a functionally active variant to an peptide by replacing an amino acid which does not significantly influence the function of said peptide can be accomplished by one skilled in the art.

A type of amino acid substitution that may be made in the polypeptides of the invention is a conservative amino acid substitution. A "conservative amino acid substitution" is one in which an amino acid residue is substituted by another amino acid residue having a side chain R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See e.g. Pearson, Methods Mol. Biol. 243:307-31 (1994).

Examples of groups of amino acids that have side chains with similar chemical properties include 1) aliphatic side chains: glycine, alanine, valine, leucine, and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartic acid and glutamic acid; and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

Alternatively, a conservative replacement is any change having a positive value in the PAM250 log-likelihood matrix disclosed in Gonnet et al., Science 256:1443-45 (1992). A "moderately conservative" replacement is any change having a nonnegative value in the PAM250 log-likelihood matrix.

A functionally active variant can also be isolated using a hybridization technique. Briefly, DNA having a high homology to the whole or part of a nucleic acid sequence encoding the peptide, polypeptide or protein of interest, e.g. Kell system antigens, is used to prepare a functionally active peptide. Therefore, a polypeptide of the invention also includes entities which are functionally equivalent and which are encoded by a nucleic acid molecule which hybridizes with a nucleic acid encoding any one of the Kell system antigens or a complement thereof. One of skill in the art can easily determine nucleic acid sequences that encode peptides of the invention using readily available codon tables. As such, these nucleic acid sequences are not presented herein.

Nucleic acid molecules encoding a functionally active variant can also be isolated by a gene amplification method such as PCR using a portion of a nucleic acid molecule DNA encoding a peptide, polypeptide, protein, antigen, or antibody of interest, e.g. Kell system antigens, as the probe.

For the purpose of the present invention, it should be considered that several polypeptides or antigens of the invention may be used in combination. All types of possible combinations can be envisioned. The same sequence can be used in several copies on the same polypeptide molecule, or wherein peptides of different amino acid sequences are used on the same polypeptide molecule; the different peptides or copies can be directly fused to each other or spaced by appropriate linkers. As used herein the term "multimerized (poly)peptide" refers to both types of combination wherein polypeptides of either different or the same amino acid sequence are present on a single polypeptide molecule. From 2 to about 20 identical and/or different peptides can be thus present on a single multimerized polypeptide molecule.

In one embodiment of the invention, a peptide, polypeptide, protein, or antigen of the invention is derived from a natural source and isolated from a bacterial source. A peptide, polypeptide, protein, or antigen of the invention can thus be isolated from sources using standard protein purification techniques.

Alternatively, peptides, polypeptides and proteins of the invention can be synthesized chemically or produced using recombinant DNA techniques. For example, a peptide, polypeptide, or protein of the invention can be synthesized by solid phase procedures well known in the art. Suitable syntheses may be performed by utilising "T-boc" or "F-moc" procedures. Cyclic peptides can be synthesised by the solid phase procedure employing the well-known "F-moc" procedure and polyamide resin in the fully automated apparatus. Alternatively, those skilled in the art will know the necessary laboratory procedures to perform the process manually. Techniques and procedures for solid phase synthesis are described in 'Solid Phase Peptide Synthesis: A Practical Approach' by E. Atherton and R. C. Sheppard, published by IRL at Oxford University Press (1989) and 'Methods in Molecular Biology, Vol. 35: Peptide Synthesis Protocols (ed. M. W. Pennington and B. M. Dunn), chapter 7, pp 91-171 by D. Andreau et al.

Alternatively, a polynucleotide encoding a peptide, polypeptide or protein of the invention can be introduced into an expression vector that can be expressed in a suitable expression system using techniques well known in the art, followed by isolation or purification of the expressed peptide, polypeptide, or protein of interest. A variety of bacterial, yeast, plant, mammalian, and insect expression systems are available in the art and any such expression system can be used. Optionally, a polynucleotide encoding a peptide, polypeptide or protein of the invention can be translated in a cell-free translation system.

Nucleic acid sequences corresponding to Kell system antigens can also be used to design oligonucleotide probes and used to screen genomic or cDNA libraries for genes encoding other variants or from other species. The basic strategies for preparing oligonucleotide probes and DNA libraries, as well as their screening by nucleic acid hybridization, are well known to those of ordinary skill in the art.

See, e.g., *DNA Cloning*: Vol. I, supra; *Nucleic Acid Hybridization*, supra; *Oligonucleotide Synthesis*, supra; Sambrook et al., supra. Once a clone from the screened library has been identified by positive hybridization, it can be confirmed by restriction enzyme analysis and DNA sequencing that the particular library insert contains a Kell system antigen gene, or a homolog thereof. The genes can then be further isolated using standard techniques and, if desired, PCR approaches or restriction enzymes employed to delete portions of the full-length sequence.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292: 756; Nambair et al. (1984) *Science* 223: 1299; Jay et al. (1984) *J. Biol. Chem.* 259: 6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, Sambrook et al., supra; *DNA Cloning*, supra; B. Perbal, supra. The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence can or can not contain a signal peptide or leader sequence. Leader sequences can be removed by the host in post-translational processing. See, e.g., U.S. Pat. Nos. 4,431,739; 4,425,437; 4,338,397. Examples of vectors include pET32a(+) and pcDNA3002Neo.

Other regulatory sequences can also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements can also be present in the vector, for example, enhancer sequences.

The control sequences and other regulatory sequences can be ligated to the coding sequence prior to insertion into a vector, such as the cloning vectors described above. Alternatively, the coding sequence can be cloned directly into an expression vector which already contains the control sequences and an appropriate restriction site.

In some cases it can be necessary to modify the coding sequence so that it can be attached to the control sequences with the appropriate orientation; i.e., to maintain the proper reading frame. It can also be desirable to produce mutants or analogs of the protein. Mutants or analogs can be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, HEK293F cells, NSO-1 cells, as well as others. Similarly, bacterial hosts such as *E. coli, Bacillus subtilis*, and *Streptococcus* spp., will find use with the present expression constructs. Yeast hosts useful in the present invention include, but are not limited to, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, but are not limited to, *Aedes aegypti, Autographa californica, Bombyx mori, Drosophila melanogaster, Spodoptera frugiperda*, and *Trichoplusia ni*.

Depending on the expression system and host selected, the proteins of the present invention are produced by culturing host cells transformed by an expression vector described above under conditions whereby the protein of interest is expressed. The protein is then isolated from the host cells and purified. The selection of the appropriate growth conditions and recovery methods are within the skill of the art.

Kell system antigen protein sequences can also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3-254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis. Chemical synthesis of peptides can be preferable if a small fragment of the antigen in question is capable of raising an immunological response in the subject of interest.

Polypeptides of the invention can also comprise those that arise as a result of the existence of multiple genes, alternative transcription events, alternative RNA splicing events, and alternative translational and postranslational events. A polypeptide can be expressed in systems, e.g. cultured cells, which result in substantially the same postranslational modifications present as when the peptide is expressed in a native cell, or in systems that result in the alteration or omission of postranslational modifications, e.g. glycosylation or cleavage, present when expressed in a native cell.

A peptide, polypeptide, protein, or antigen of the invention can be produced as a fusion protein that contains other distinct amino acid sequences that are not part of the Kell system antigen sequences disclosed herein, such as amino acid linkers or signal sequences or immunogenic carriers, as well as ligands useful in protein purification, such as glutathione-S-transferase, histidine tag, and staphylococcal protein A. More than one polypeptide of the invention can be present in a fusion protein. The heterologous polypeptide can be fused, for example, to the N-terminus or C-terminus of the peptide, polypeptide or protein of the invention. A peptide, polypeptide, protein, or antigen of the invention can also be produced as fusion proteins comprising homologous amino acid sequences.

Blood Group Antigen Proteins

Any of a variety of cell surface proteins found on red blood cells may be used in the practice of the present invention. In one embodiment, the proteins are blood group antigens, such as the Kell system antigens. Information on such antigens and, in particular, soluble forms are available in the art, for example, in Ridgwell et al., Transfusion Medicine, 17: 384-394 (2007).

Kell (CD238) is a clinically important human blood group antigen system comprising 28 antigens (Daniels et al., 2007, International Society of Blood Transfusion Committee on Terminology for Red Cell Surface Antigens: Cape Town report. Vox Sanguinis, 92, 250-253). The Kell antigens are carried by a single pass type II (cytoplasmic N-terminus) red blood cell membrane glycoprotein. The Kell glycoprotein is expressed in red cells and haematopoietic tissue (bone marrow and foetal liver) and to a lesser extent in other tissues, including brain, lymphoid organs, heart and skeletal muscle (Russo et al., 2000, Blood, 96, 340-346). The K/k (KEL1/KEL2) blood group antigen polymorphism is determined by a single nucleotide polymorphism (SNP) resulting in the presence of methionine (M) or threonine (T), respectively, at amino acid 193 of the extracellular C-terminal domain (Lee, 1997, Vox Sanguinis, 73, 1-11). The other mostclinically significant antithetical antigens $Kp^a/Kp^b$ (KEL3/KEL4) and $Js^a/Js^b$ (KEL6/KEL7) are also the result of SNPs resulting in single amino acid changes in the extracellular domain (Lee, 1997, Vox Sanguinis, 73, 1-11).

Kell system antibodies are known to cause haemolytic transfusion reactions and haemolytic disease of the fetus and newborn (HDFN). Kell-related HDFN may be because of suppression of fetal erythropoiesis in addition to immune destruction of red blood cells as in most other cases of HDFN (Vaughan et al., 1998, New England Journal of Medicine, 338, 798-803; Daniels et al., 2003, Transfusion, 43, 115-116). Anti-K (KEL1) is the most commonly encountered immune red cell antibody outside the ABO and Rh systems, and other antigens of the Kell blood group system, e.g. k (KEL2), $Kp^a$ (KEL3), $Kp^b$ (KEL4), $Js^a$ (KEL6) and $Js^b$ (KEL7) are also capable of stimulating the production of haemolytic antibodies and causing HDFN (Daniels, 2002, Human Blood Groups (2nd edn). Blackwell, Oxford).

The Duffy (Fy, CD234) blood group antigens are carried by a type III membrane glycoprotein, which is predicted to span the membrane seven times with a glycosylated extracellular N-terminus and a cytoplasmic C-terminus. It is expressed in red blood cells, vascular endothelial cells and a wide range of other tissues including kidney, lung, liver, spleen, brain (Iwamoto et al., 1996, Blood, 87, 378-385) and colon (Chaudhuri et al., 1997, Blood, 89, 701-712). The $Fy^a/Fy^b$ (FY1/FY2) blood group polymorphism is determined by an SNP resulting in the presence of glycine (G) or aspartic acid (D), respectively, at amino acid 42 in the N-terminal extracellular domain (Iwamoto et al., 1995, Blood, 85, 622-626; Mallinson et al., 1995, British Journal of Haematology, 90, 823-82; Tournamille et al., 1995, Human Genetics, 95, 407-410). Duffy blood group system antibodies can cause haemolytic transfusion reactions (Boyland et al., 1982, Transfusion, 22, 402; Sosler et al., 1989, Transfusion, 29, 505-507) and HDFN (Vescio et al., 1987, Transfusion, 27, 366; Goodrick et al., 1997, Transfusion Medicine, 7, 301-304).

The Lutheran (Lu, B-CAM, CD239) blood group antigens are carried by two single-pass type I (cytoplasmic C-terminus) membrane glycoproteins, which differ in the length of their cytoplasmic domains [the B-CAM glycoprotein has a shorter C-terminal cytoplasmic tail than Lu (Campbell et al., 1994, Cancer Research, 54, 5761-5765)]. The Lu glycoprotein has five extracellular immunoglobulin-like domains and is a member of the immunoglobulin gene superfamily (IgSF) (Parsons et al., 1995, Proceedings of the National Academy of Science of the United States of America, 92, 5496-5500) and is expressed in red blood cells and a wide range of other tissues (Reid & Lomas-Francis, 2004, The Blood Group Antigens Factsbook (2nd edn). Academic Press, London). The $Lu^a/Lu^b$ (LU1/LU2) blood group antigen polymorphism is determined by a SNP resulting in the presence of histidine (H) or arginine (R), respectively, at amino acid 77 of the first predicted N-terminal IgSF domain (El Nemer et al., 1997). Lutheran blood group system antibodies have been reported to be involved in mild delayed haemolytic transfusion reactions (Daniels, 2002, Human Blood Groups (2nd edn). Blackwell, Oxford) but are rarely involved in HDFN (Inderbitzen et al., 1982, Transfusion, 22, 542).

Antibodies

As used herein, the term "antibody" refers to any immunoglobulin or intact molecule as well as to fragments thereof that bind to a specific epitope. Such antibodies include, but are not limited to polyclonal, monoclonal, chimeric, humanized, single chain, Fab, Fab', F(ab)' fragments and/or F(v) portions of the whole antibody and variants thereof. All isotypes are encompassed by this term, including IgA, IgD, IgE, IgG, and IgM.

As used herein, the term "antibody fragment" refers specifically to an incomplete or isolated portion of the full sequence of the antibody which retains the antigen binding function of the parent antibody. Examples of antibody fragments include Fab, Fab', F(ab')2, and Fv fragments; diabodies; linear antibodies; single-chain antibody molecules; and multispecific antibodies formed from antibody fragments.

An intact "antibody" comprises at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $CH_1$, $CH_2$ and $CH_3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. The term antibody includes antigen-binding portions of an intact antibody that retain capacity to bind. Examples of binding include (i) a Fab fragment, a monovalent fragment consisting of the $V_L$, $V_H$, $C_L$ and CH1 domains; (ii) a F(ab)$_2$ fragment, a bivalent fragment comprising two Fab fragments linked by a disulfide bridge at the hinge region; (iii) a Fd fragment consisting of the VH and CH1 domains; (iv) a Fv fragment consisting of the $V_L$ and $V_H$ domains of a single arm of an antibody, (v) a dAb fragment (Ward et al., Nature, 341:544-546 (1989)), which consists of a $V_H$ domain; and (vi) an isolated complementarity determining region (CDR).

As used herein, the term "single chain antibodies" or "single chain Fv (scFv)" refers to an antibody fusion molecule of the two domains of the Fv fragment, $V_L$ and $V_H$. Although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see, e.g., Bird et al., Science, 242:423-426 (1988); and Huston et al., Proc Natl Acad Sci USA, 85:5879-5883 (1988)). Such single chain antibodies are included by reference to the term "antibody" fragments and can be prepared by recombinant techniques or enzymatic or chemical cleavage of intact antibodies.

As used herein, the term "human sequence antibody" includes antibodies having variable and constant regions (if present) derived from human germline immunoglobulin sequences. The human sequence antibodies of the invention can include amino acid residues not encoded by human germline immunoglobulin sequences (e.g., mutations introduced by random or site-specific mutagenesis in vitro or by somatic mutation in vivo). Such antibodies can be generated in non-human transgenic animals, e.g., as described in PCT App. Pub. Nos. WO 01/14424 and WO 00/37504. However, the term "human sequence antibody", as used herein, is not intended to include antibodies in which CDR sequences derived from the germline of another mammalian species, such as a mouse, have been grafted onto human framework sequences (e.g., humanized antibodies).

Also, recombinant immunoglobulins can be produced. See, Cabilly, U.S. Pat. No. 4,816,567, incorporated herein by reference in its entirety and for all purposes; and Queen et al., Proc Natl Acad Sci USA, 86:10029-10033 (1989).

As used herein, the term "monoclonal antibody" refers to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one aspect, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

As used herein, the term "antigen" refers to a substance that prompts the generation of antibodies and can cause an immune response. It can be used interchangeably in the present disclosure with the term "immunogen". In the strict sense, immunogens are those substances that elicit a response from the immune system, whereas antigens are defined as substances that bind to specific antibodies. An antigen or fragment thereof can be a molecule (i.e., an epitope) that makes contact with a particular antibody. When a protein or a fragment of a protein is used to immunize a host animal, numerous regions of the protein can induce the production of antibodies (i.e., elicit the immune response), which bind specifically to the antigen (given regions or three-dimensional structures on the protein).

An "epitope" refers to the portion of the antigen bound by an antibody. Antigens may comprise multiple epitopes. Where the antigen is a protein, linear epitopes may range from about 5 to 20 amino acids in length. Antibodies may also recognize conformational determinants formed by non-contiguous residues on an antigen, and an epitope can therefore require a larger fragment of the antigen to be present for binding, e.g. a protein domain, or substantially all of a protein sequence. It will therefore be appreciated that a protein, which may be several hundred amino acids in length, can comprise a number of distinct epitopes.

As used herein, the term "humanized antibody," refers to at least one antibody molecule in which the amino acid sequence in the non-antigen binding regions and/or the antigen-binding regions has been altered so that the antibody more closely resembles a human antibody, and still retains its original binding ability.

In addition, techniques developed for the production of "chimeric antibodies" (Morrison, et al., Proc Natl Acad Sci, 81:6851-6855 (1984), incorporated herein by reference in their entirety) by splicing the genes from a mouse antibody molecule of appropriate antigen specificity together with genes from a human antibody molecule of appropriate biological activity can be used. For example, the genes from a mouse antibody molecule specific for an autoinducer can be spliced together with genes from a human antibody molecule of appropriate biological activity. A chimeric antibody is a molecule in which different portions are derived from different animal species, such as those having a variable region derived from a murine mAb and a human immunoglobulin constant region.

In addition, techniques have been developed for the production of humanized antibodies (see, e.g., U.S. Pat. No. 5,585,089 and U.S. Pat. No. 5,225,539, which are incorporated herein by reference in their entirety). An immunoglobulin light or heavy chain variable region consists of a "framework" region interrupted by three hypervariable regions, referred to as complementarity determining regions (CDRs). Briefly, humanized antibodies are antibody molecules from non-human species having one or more CDRs from the non-human species and a framework region from a human immunoglobulin molecule.

Alternatively, techniques described for the production of single chain antibodies can be adapted to produce single chain antibodies against an immunogenic conjugate of the present disclosure. Single chain antibodies are formed by linking the heavy and light chain fragments of the Fv region via an amino acid bridge, resulting in a single chain polypeptide. Fab and F(ab')2 portions of antibody molecules can be prepared by the proteolytic reaction of papain and pepsin, respectively, on substantially intact antibody molecules by methods that are well-known. See e.g., U.S. Pat. No. 4,342,566. Fab' antibody molecule portions are also well-known and are produced from F(ab')2 portions followed by reduction of the disulfide bonds linking the two heavy chain portions as with mercaptoethanol, and followed by alkylation of the resulting protein mercaptan with a reagent such as iodoacetamide.

Antibody Assays

A number of screening assays are known in the art for assaying antibodies of interest to confirm their specificity and affinity and to determine whether those antibodies cross-react with other proteins.

The terms "specific binding" or "specifically binding" refer to the interaction between the antigen and their corresponding antibodies. The interaction is dependent upon the presence of a particular structure of the protein recognized by the binding molecule (i.e., the antigen or epitope). In order for binding to be specific, it should involve antibody binding of the epitope(s) of interest and not background antigens.

Once antibodies are produced, they are assayed to confirm that they are specific for the antigen of interest and to determine whether they exhibit any cross reactivity with other antigens. One method of conducting such assays is a sera screen assay as described in U.S. App. Pub. No. 2004/0126829, the contents of which are hereby expressly incorporated herein by reference. However, other methods of assaying for quality control are within the skill of a person of ordinary skill in the art and therefore are also within the scope of the present disclosure.

Antibodies, or antigen-binding fragments, variants or derivatives thereof of the present disclosure can also be described or specified in terms of their binding affinity to an antigen. The affinity of an antibody for an antigen can be determined experimentally using any suitable method. (See, e.g., Berzofsky et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, $K_a$, $K_d$) are preferably made with standardized solutions of antibody and antigen, and a standardized buffer.

The affinity binding constant ($K_{aff}$) can be determined using the following formula:

$$K_{aff} = \frac{(n-1)}{2(n[mAb']_t - [mAb]_t)}$$

in which:

$$n = \frac{[mAg]_t}{[mAg']_t}$$

[mAb] is the concentration of free antigen sites, and [mAg] is the concentration of free monoclonal binding sites as determined at two different antigen concentrations (i.e., $[mAg]_t$ and $[mAg']_t$) (Beatty et al., J Imm Meth, 100:173-179 (1987)).

The term "high affinity" for an antibody refers to an equilibrium association constant ($K_{aff}$) of at least about $1 \times 10^7$ liters/mole, or at least about $1 \times 10^8$ liters/mole, or at least about $1 \times 10^9$ liters/mole, or at least about $1 \times 10^{10}$ liters/mole, or at least about $1 \times 10^{11}$ liters/mole, or at least about $1 \times 10^{12}$ liters/mole, or at least about $1 \times 10^{13}$ liters/mole, or at least about $1 \times 10^{14}$ liters/mole or greater. "High affinity" binding can vary for antibody isotypes. $K_D$, the equilibrium dissociation constant, is a term that is also used to describe antibody affinity and is the inverse of $K_{aff}$.

$K_D$, the equilibrium dissociation constant, is a term that is also used to describe antibody affinity and is the inverse of $K_{aff}$. If $K_D$ is used, the term "high affinity" for an antibody refers to an equilibrium dissociation constant ($K_D$) of less than about $1 \times 10^{-7}$ mole/liters, or less than about $1 \times 10^{-8}$ mole/liters, or less than about $1 \times 10^{-9}$ mole/liters, or less than about $1 \times 10^{-10}$ mole/liters, or less than about $1 \times 10^{-11}$ mole/liters, or less than about $1 \times 10^{-12}$ mole/liters, or less than about $1 \times 10^{-13}$ mole/liters, or less than about $1 \times 10^{-14}$ mole/liters or lower.

The immunoglobulin molecules of the present invention can be of any type (e.g., IgG, IgE, IgM, IgD, IgA and IgY), class (e.g., IgG1, IgG2, IgG3, IgG4, IgA1 and IgA2), or subclass of immunoglobulin molecule. In some embodiments, the antibodies are antigen-binding antibody fragments (e.g., human) and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. Antigen-binding antibody fragments, including single-chain antibodies, can comprise the variable region(s) alone or in combination with the entirety or a portion of the following: hinge region, CH1, CH2, and CH3 domains. Also included in the present disclosure are antigen-binding fragments comprising any combination of variable region(s) with a hinge region, CH1, CH2, and CH3 domains.

Pharmaceutical Compositions

The presently disclosed subject matter provides pharmaceutical compositions comprising the antibodies produced in accordance with the present disclosure. In some embodiments, a pharmaceutical composition can comprise one or more monoclonal antibodies produced using the methods disclosed herein. In some embodiments, a panel of monoclonal antibodies produced according to the present disclosure can be included in a pharmaceutical composition.

In some embodiments a pharmaceutical composition can also contain a pharmaceutically acceptable carrier or adjuvant for administration of the antibody. In some embodiments, the carrier is pharmaceutically acceptable for use in humans. The carrier or adjuvant should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonate and benzoates.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated as tablets, pills, dragees, capsules, liquids, gels, syrups, slurries and suspensions, for ingestion by the patient.

The compositions of the presently disclosed subject matter can further comprise a carrier to facilitate composition preparation and administration. Any suitable delivery vehicle or carrier can be used, including but not limited to a microcapsule, for example a microsphere or a nanosphere (Manome et al. (1994) Cancer Res 54:5408-5413; Saltzman & Fung (1997) Adv Drug Deliv Rev 26:209-230), a glycosaminoglycan (U.S. Pat. No. 6,106,866), a fatty acid (U.S. Pat. No. 5,994,392), a fatty emulsion (U.S. Pat. No. 5,651, 991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al. (1997) Cancer Res 57:1447-1451 and U.S. Pat. Nos. 4,551,482, 5,714,166, 5,510,103, 5,490,840, and 5,855,900), and a polysome (U.S. Pat. No. 5,922,545).

Antibody sequences can be coupled to active agents or carriers using methods known in the art, including but not limited to carbodiimide conjugation, esterification, sodium periodate oxidation followed by reductive alkylation, and glutaraldehyde crosslinking (Goldman et al. (1997) Cancer Res. 57:1447-1451; Cheng (1996) Hum. Gene Ther. 7:275-282; Neri et al. (1997) Nat. Biotechnol. 15:1271-1275; Nabel (1997) Vectors for Gene Therapy. In Current Protocols in Human Genetics, John Wiley & Sons, New York; Park et al. (1997) Adv. Pharmacol. 40:399-435; Pasqualini et al. (1997) Nat. Biotechnol. 15:542-546; Bauminger & Wilchek (1980) Meth. Enzymol. 70:151-159; U.S. Pat. No. 6,071,890; and European Patent No. 0 439 095).

A therapeutic composition of the present invention comprises in some embodiments a pharmaceutical composition that includes a pharmaceutically acceptable carrier. Suitable formulations include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans.

Pharmaceutical compositions of the present disclosure can have a pH between 5.5 and 8.5, preferably between 6 and 8, and more preferably about 7. The pH can be maintained by the use of a buffer. The composition can be sterile and/or pyrogen free. The composition can be isotonic with respect to humans. Pharmaceutical compositions of the presently disclosed subject matter can be supplied in hermetically-sealed containers.

Pharmaceutical compositions can include an effective amount of one or more antibodies as described herein. In some embodiments, a pharmaceutical composition can comprise an amount that is sufficient to treat, ameliorate, or prevent a desired disease or condition, or to exhibit a detectable therapeutic effect. Therapeutic effects also include reduction in physical symptoms. The precise effective amount for any particular subject will depend upon their size and health, the nature and extent of the condition, and therapeutics or combination of therapeutics selected for administration. The effective amount for a given situation is determined by routine experimentation as practiced by one of ordinary skill in the art.

Treatment Regimens: Pharmacokinetics

The pharmaceutical compositions of the invention can be administered in a variety of unit dosage forms depending upon the method of administration. Dosages for typical antibody pharmaceutical compositions are well known to those of skill in the art. Such dosages are typically advisory in nature and are adjusted depending on the particular therapeutic context or patient tolerance. The amount antibody adequate to accomplish this is defined as a "therapeutically effective dose." The dosage schedule and amounts effective for this use, i.e., the "dosing regimen," will depend upon a variety of factors, including the stage of the disease or condition, the severity of the disease or condition, the general state of the patient's health, the patient's physical status, age, pharmaceutical formulation and concentration of active agent, and the like. In calculating the dosage regimen for a patient, the mode of administration also is taken into consideration. The dosage regimen must also take into consideration the pharmacokinetics, i.e., the pharmaceutical composition's rate of absorption, bioavailability, metabolism, clearance, and the like. See, e.g., the latest Remington's; Egleton, *Peptides* 18: 1431-1439, 1997; Langer, *Science* 249: 1527-1533, 1990.

For purposes of the present invention, a therapeutically effective amount of a composition comprising an antibody, contains about 0.05 to 1500 μg protein, preferably about 10 to 1000 μg protein, more preferably about 30 to 500 μg and most preferably about 40 to 300 μg, or any integer between these values. For example, antibodies of the invention can be administered to a subject at a dose of about 0.1 μg to about 200 mg, e.g., from about 0.1 μg to about 5 μg, from about 5 μg to about 10 μg, from about 10 μg to about 25 μg, from about 25 μg to about 50 μg, from about 50 μg to about 100 μg, from about 100 μg to about 500 μg, from about 500 μg to about 1 mg, from about 1 mg to about 2 mg, with optional boosters given at, for example, 1 week, 2 weeks, 3 weeks, 4 weeks, two months, three months, 6 months and/or a year later. It is understood that the specific dose level for any particular patient depends upon a variety of factors including the activity of the specific antibody employed, the age, body weight, general health, sex, diet, time of administration, route of administration, and rate of excretion, drug combination and the severity of the particular disease undergoing therapy.

Routes of administration include, but are not limited to, oral, topical, subcutaneous, intramuscular, intravenous, subcutaneous, intradermal, transdermal and subdermal. Depending on the route of administration, the volume per dose is preferably about 0.001 to 10 ml, more preferably about 0.01 to 5 ml, and most preferably about 0.1 to 3 ml. Compositions can be administered in a single dose treatment or in multiple dose treatments on a schedule and over a time period appropriate to the age, weight and condition of the subject, the particular antibody formulation used, and the route of administration.

Kits

The invention provides kits comprising antibodies produced in accordance with the present disclosure which can be used, for instance, for therapeutic applications described above. The article of manufacture comprises a container with a label. Suitable containers include, for example, bottles, vials, and test tubes. The containers can be formed from a variety of materials such as glass or plastic. The container holds a composition which includes an active agent that is effective for therapeutic applications, such as described above. The active agent in the composition can comprise the antibody. The label on the container indicates that the composition is used for a particular therapy or non-therapeutic application, and can also indicate directions for either in vivo or in vitro use, such as those described above.

The following examples of specific aspects for carrying out the present invention are offered for illustrative purposes only, and are not intended to limit the scope of the present invention in any way.

EXAMPLES

Example 1: Generation of Monoclonal Antibodies Against Kell Antigens

We generated mice expressing the human Kell glycoprotein (K variant) on RBCs. Transgenic RBCs were then transfused into wild-type mice, thus allowing cell surface expression without the introduction of additional antigens. The recipient mice were pretreated with poly (I:C), which acts a an adjuvant to increase antibody responses to antigens on transfused RBCs, as first described by Dr. Zimring (*Transfusion* 46(9): 1526-36, 2006). Splenocytes from immunized mice were fused with myeloma partners and monoclonal antibodies were isolated. We have isolated three clones that produce monoclonal IgG antibodies, which recognize the K form of the Kell glycoprotein but not the k form. These antibodies are useful typing reagents for human RBCs by a variety of methods, including, but not limited to, fluid phase agglutination, solid phase detection, tube gel detection, flow cytometry detection, enzyme linked immunoadsorbant assay, radioimmunoassay, and Western blot.

Shown in FIGS. 1-6 are the sequences of the antibodies obtained. Upon sequencing, it was determined that the antibodies designated PUMA 1 and PUMA 2 were the same. The shading indicates where the highly variable regions begin. The CDR regions of each heavy or light chain are underlined.

The specificities of the antibodies are shown in FIGS. 7A, 7B, 8A, 8B, 9A-9C, and 10A-10I. The specificities of the antibodies were determined to be: PUMA1/2 (KEL1 or K), PUMA 3 (a common Kell epitope, PUMA 4 (KEL4 or $Kp^b$). Flow cytometry was utilized to test antibody specificity by indirect immunofluorescence, using the monocolonal antibodies as the primary reagent and a goat-anti-mouse antibody (conjugated to allophycocyanin) as a secondary antibody. Different target cells expressing different Kell variants were used to determine specificity. Targets included RBCs that phenotyped as homozygous for the 3 main antithetical antigens in the Kell system, K/K, k/k, $Kp^b/Kp^b$, $Kp^a/Kp^a$, $Js^b/Js^b$, $Js^a/Js^a$. Differential binding to such tarets tests specificity. In the case of PUMA ½, binding was only observed when K was present but not on k/k RBCs. In the case of PUMA 3, binding was observed on all RBCs regardless of phenotype for K/k, $Kp^a/Kp^b$, or $Js^a/Js^b$, thus indicating a common epitope outside these systems. However, PUMA 3 bound to only KELL glycoprotein transgenic murine RBCs and not wild-type murine RBCs; thus, the epitope recognized by PUMA 3 is on the KELL molecule, but not K/k, $Kp^a/Kp^b$, or $Js^a/Js^b$. For PUMA 4, binding was only observed when $Kp^b$ was present but not on $Kp^a/Kp^a$ RBCs.

Example 2: Isolation of Protective Antibodies

Figure 7B:
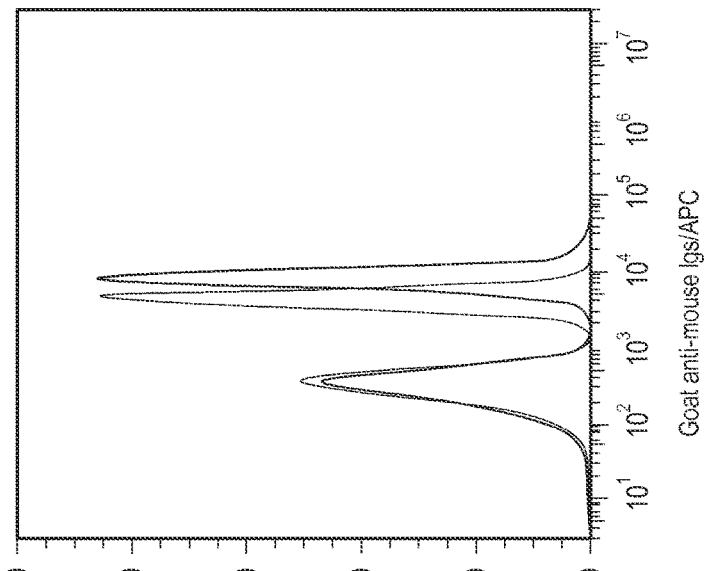
FIGS. 7A, 7B shows the specificity of monoclonal antibody Puma 1.
Figure 7A:
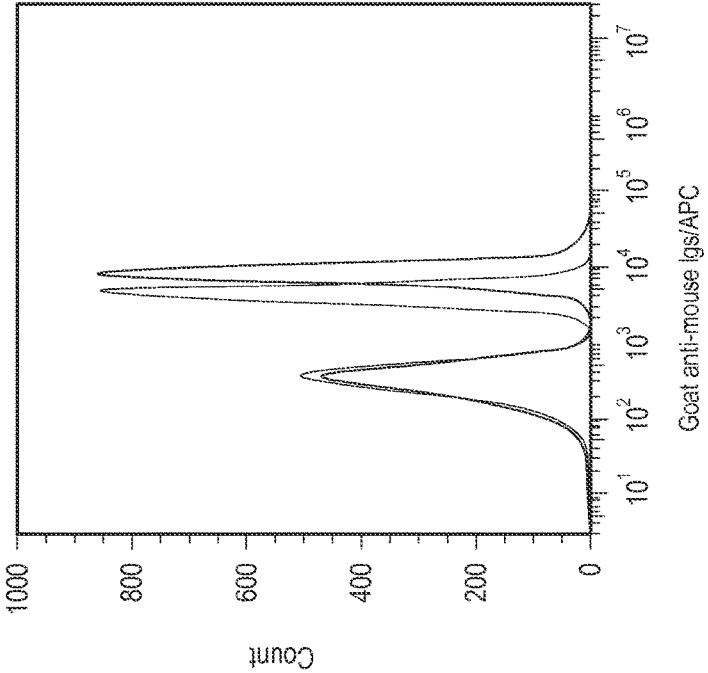
Figure 8A:
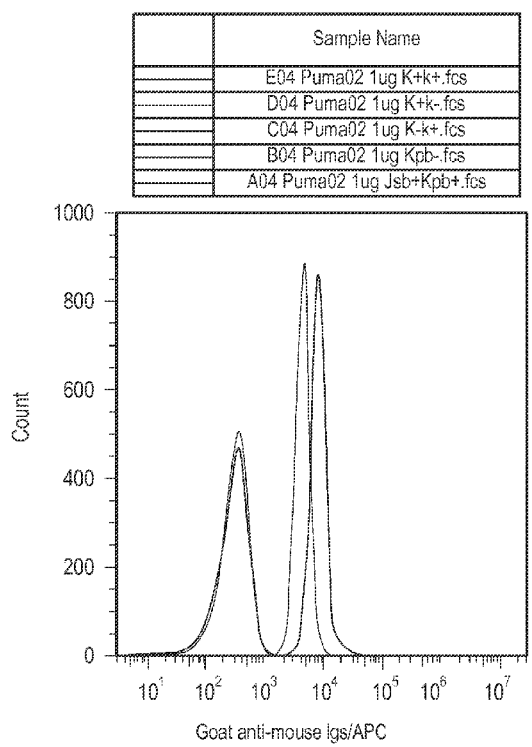
FIGS. 8A, 8B shows the specificity of monoclonal antibody Puma 2.
Figure 8B:
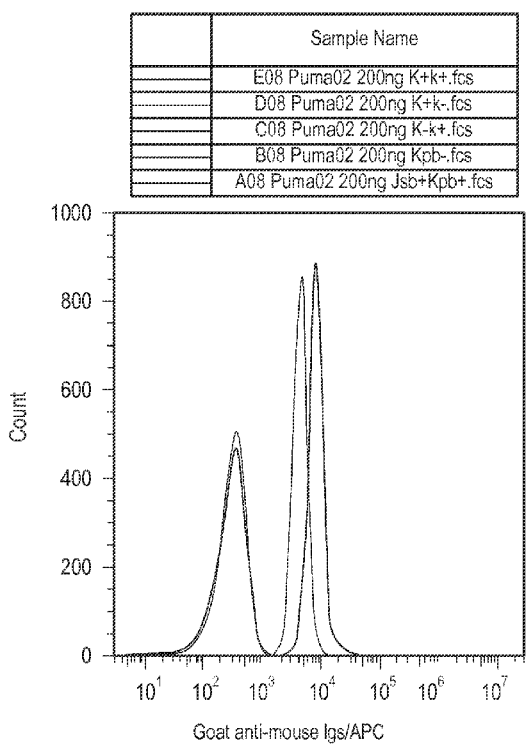
Figures 9A, 9B:
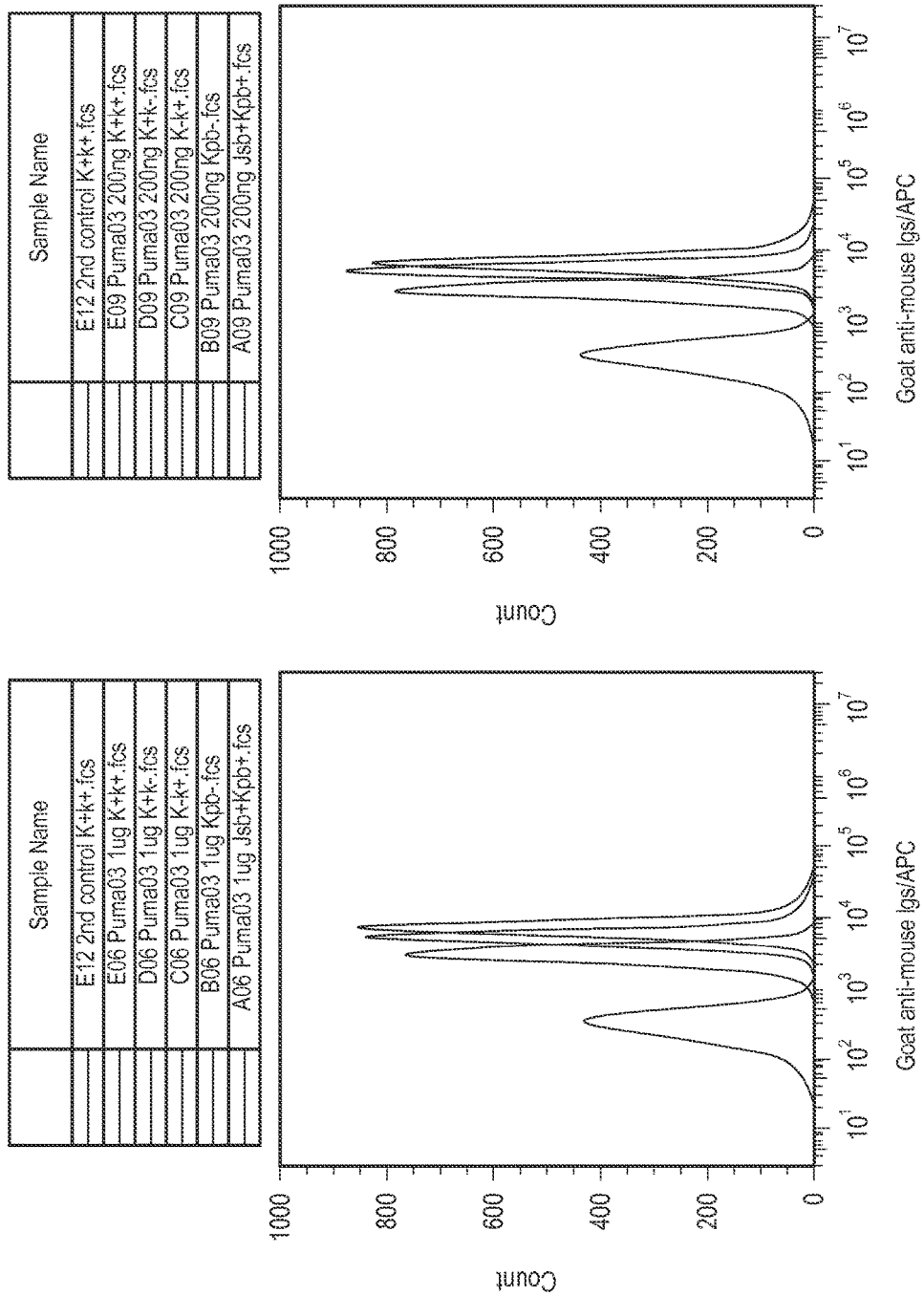
FIGS. 9A-9C shows the specificity of monoclonal antibody Puma 3.
Figure 10A:
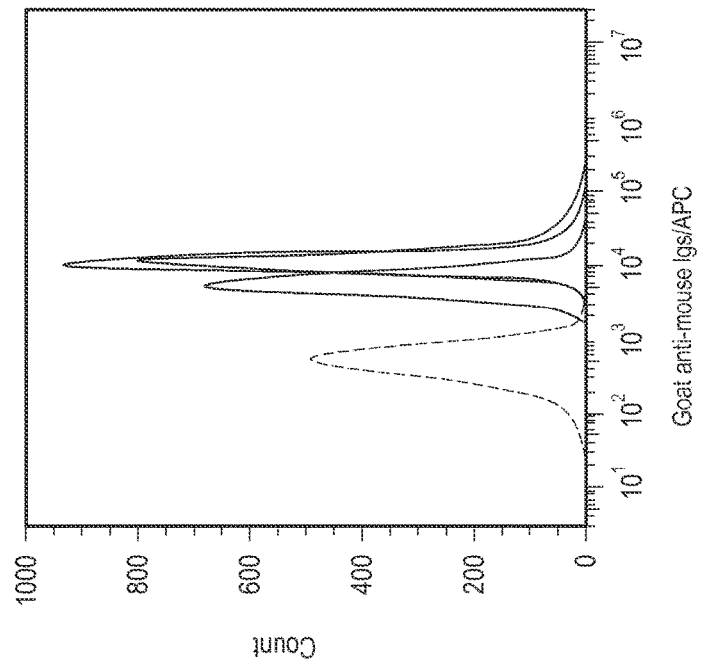
FIGS. 10A-10I shows the specificity of monoclonal antibody Puma 4.
Figure 9C:
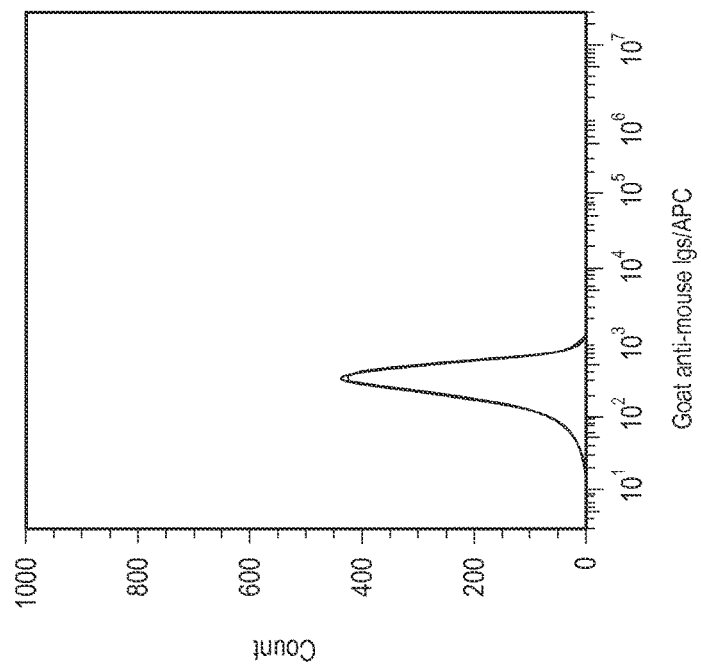
Figure 10C:
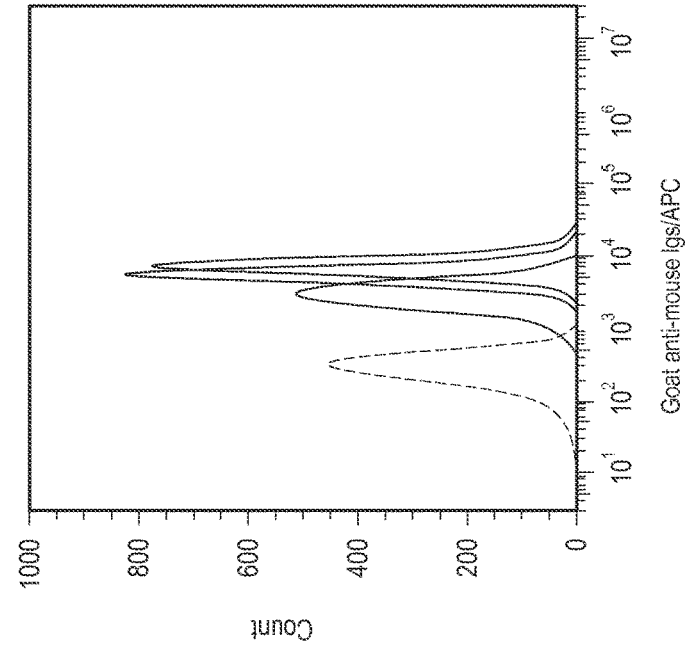
Figure 10B:
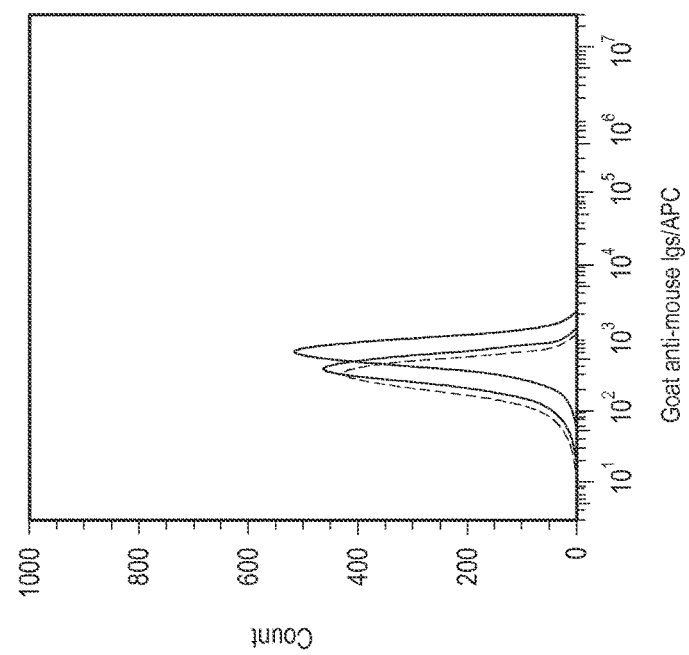
Figure 10E:
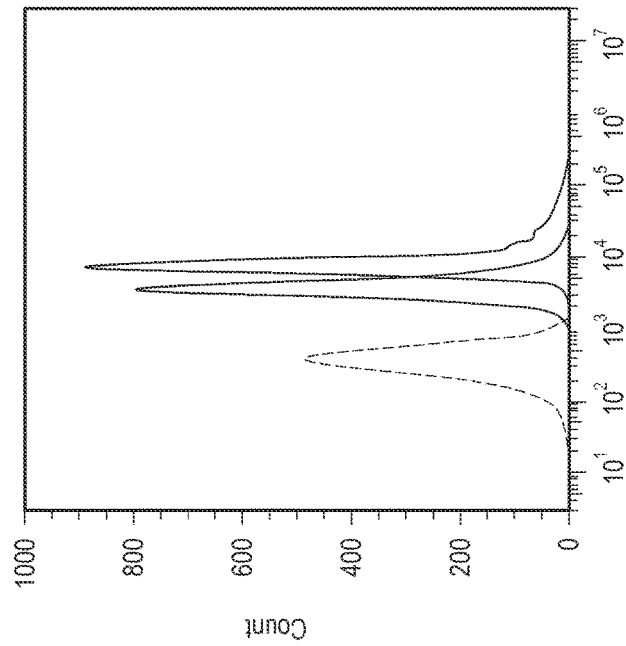
Figure 10D:
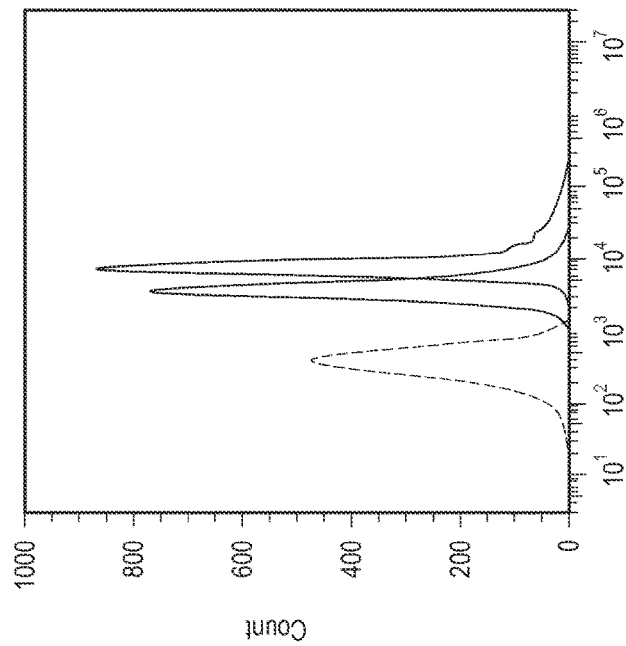
Figure 10G:
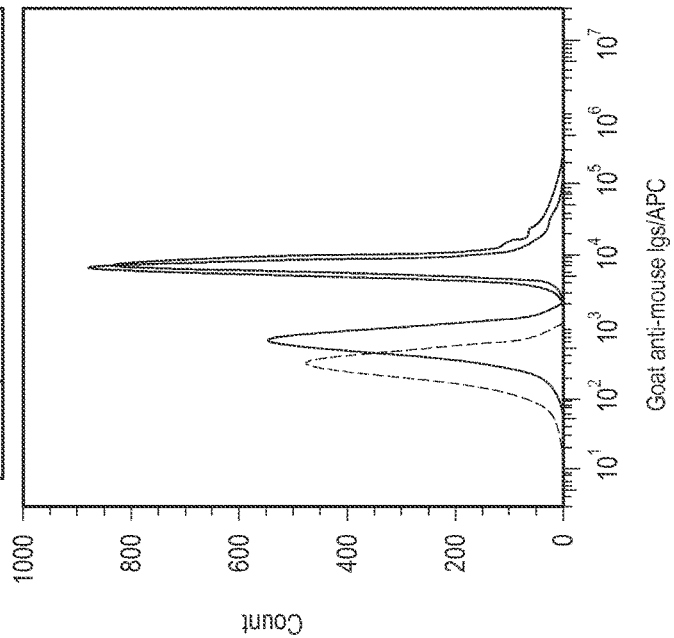
Figure 10F:
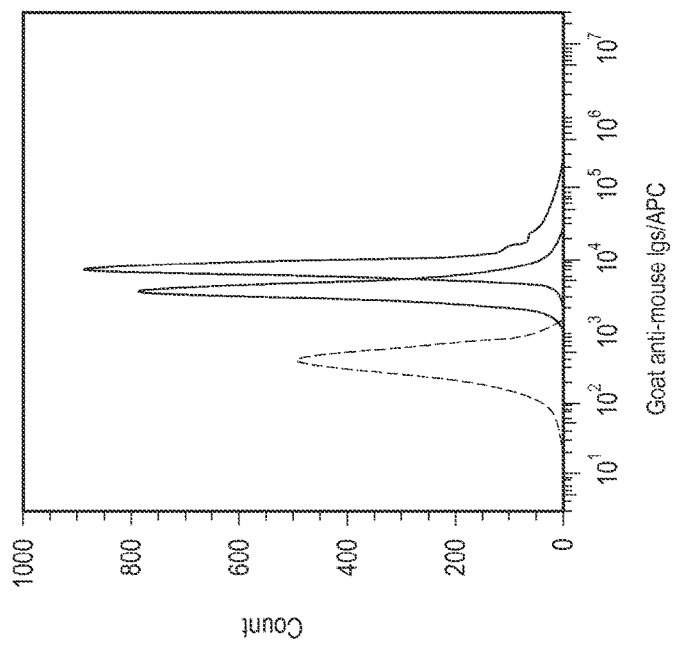
Figure 10H:
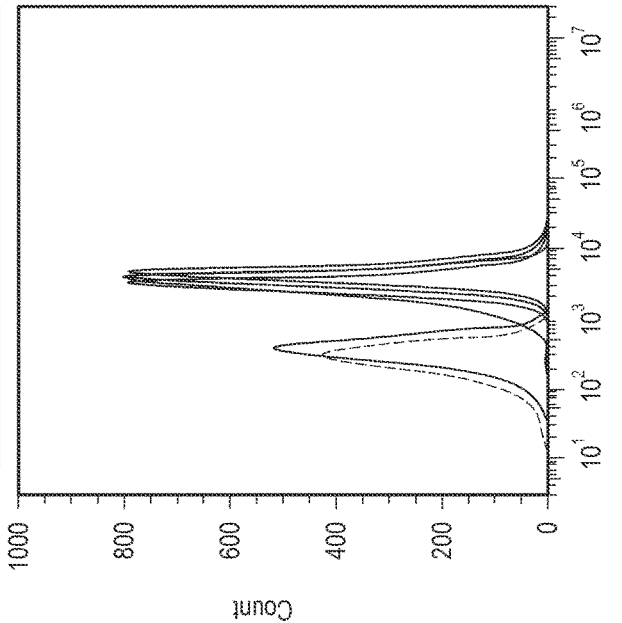
Figure 10I:
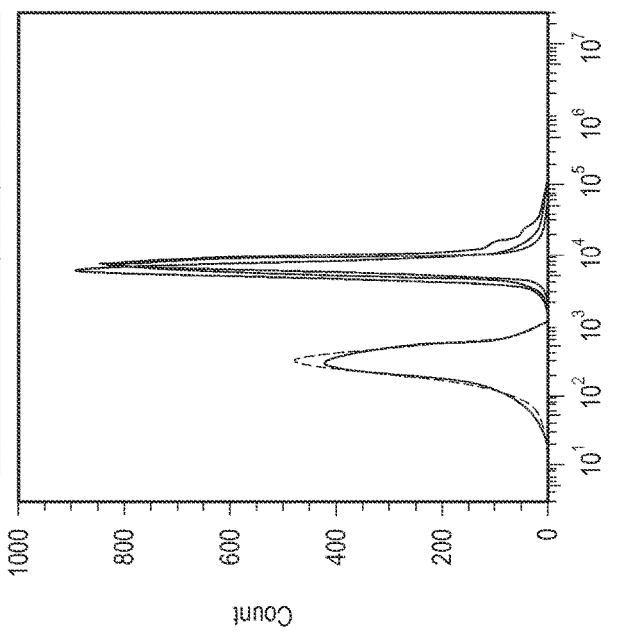

In order to engineer a protective antibody of as disclosed herein, one must first isolate the sequence of antibody of the correct specificity to develop the desired therapeutic. As described in Example 1, to isolate antibodies with high affinity and specificity for a given blood group antigen, transgenic mice were created that express human Kell glycoprotein as a transgene; the transgenic RBCs were used as an immunogen in wild-type recipient mice. The variety of human Kell glycoprotein used expressed the KEL1, $Kp^b$, and $Js^b$ variants of the KEL1/KEL2, $Kp^a/Kp^b$, and $Js^a/Js^b$ antithetical antigens, respectively. After a high titer was achieved, spleens were harvested from recipient mice, fusions were performed with a murine myeloma B cell line, and monoclonal antibodies were isolated. An anti-Kell antibody specific for the KEL1 variant of the KEL1/KEL2 antithetical pair was isolated, and named PUMA1, as described in Example 1. PUMA1 was further characterized as being of the IgG2a subtype and expressing a kappa light chain variant. PUMA1 specifically recognizes the KEL1 antigen with limited or no binding of the KEL2 variant (FIGS. 7A, 7B).

Figure 13:
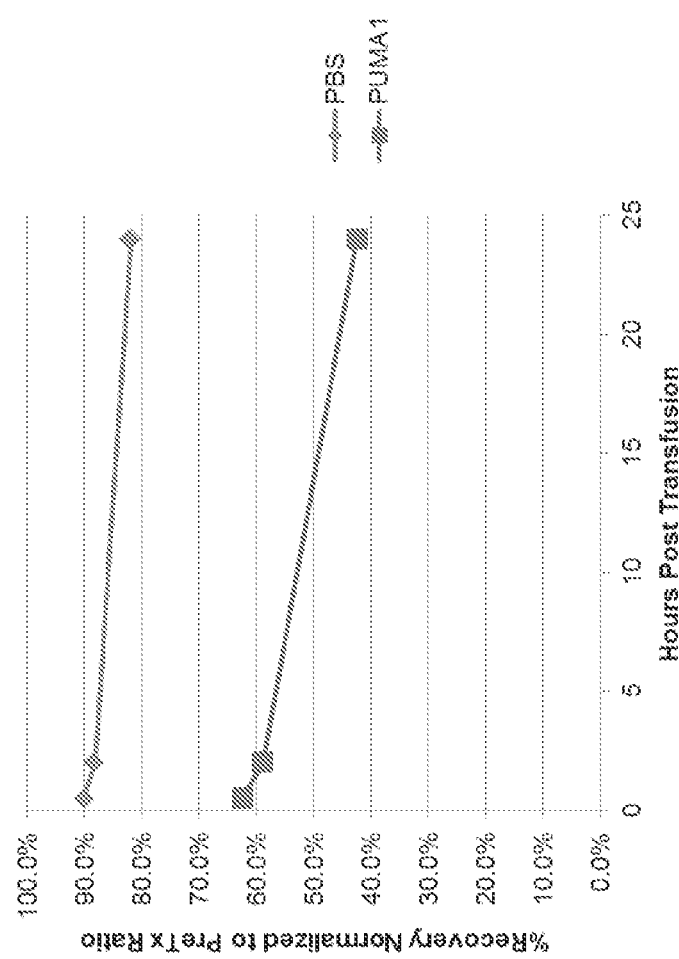
FIG. 13 shows that PUMA 1 has the capacity to cause a hemolytic transfusion reaction (HTR), in a mouse model, in vivo.

The ability of PUMA1 to induce a HTR was tested by passive immunization of wild-type mice with PUMA1 (by intravenous tail-vein injection), followed by transfusion with murine KEL1+RBCs from KEL1 transgeneic mouse donors. Compared to a control group that got only PBS, PUMA1 caused a brisk clearance of KEL1+RBCs, after which, the surviving RBCs continued to circulate, as is typical of HTRs in both mice and also in humans (FIG. 13). Thus, PUMA1 specifically binds to KEL1 RBCs, in vivo, with sufficient activity to induce an HTR.

Example 3: Antibody Modification

Figure 17:
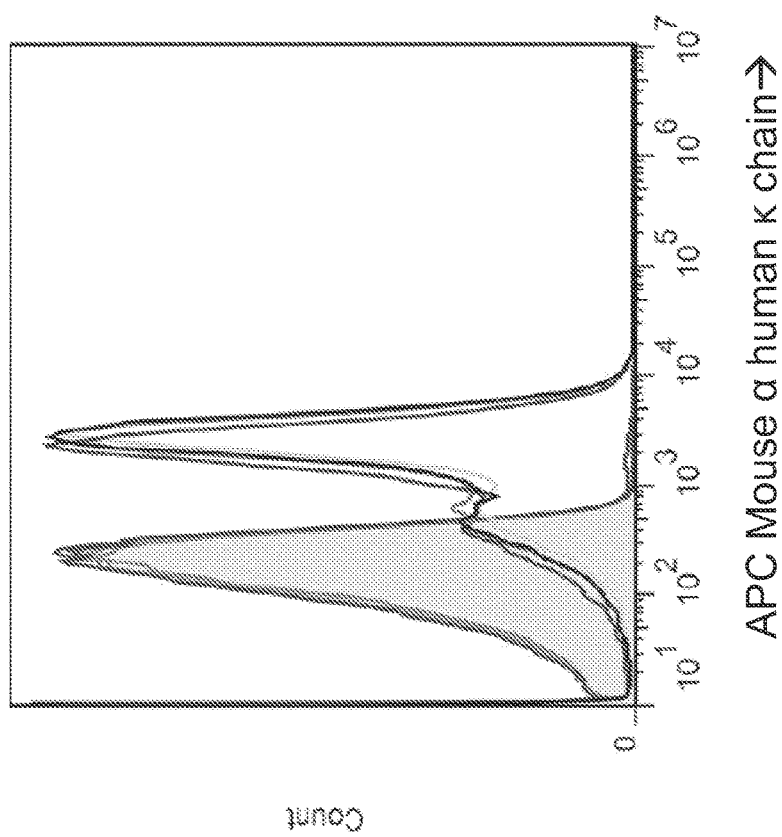
FIG. 17 shows recombinant generation of a humanized form of PUMA1 and its ability to bind to antigen positive RBCs, demonstrating a maintenance of binding after humanization of the IgG constant region.

To allow engineering and manipulation of PUMA1, rapid amplification of cDNA ends (RACE) was performed on both the heavy and light chains of PUMA1, and the sequence for the PUMA1 antibody was elucidated (see FIGS. 1 and 2). Based upon the predicted sequence, mass spectrometry was performed on purified monoclonal PUMA1 and predicted peptides were confirmed for both the heavy and light chain, demonstrating that the correct cDNA was amplified. The identified sequence of PUMA1 heavy chain was cloned in frame with cDNA coding sequence for the mouse IgG3 subtypes, in a eukaryotic expression vector. Similarly, the sequence of the PUMA1 light chain was cloned into a Eukaryotic expression vector. IgG3 was chosen, since it is typically known to have a diminished capacity to induce clearance of bound targets than IgG2a. The plasmid encoding PUMA1 IgG3 heavy chain was transfected into CHO cells, along with the expression vector for light chain, and PUMA1 IgG3 was then purified from culture supernatant using protein A affinity chromatography. Recombinant PUMA1 IgG2a was engineered and expressed in the same way, to allow PUMA1 IgG2a expressed in the same system as the PUMA1 IgG3. Similar to the above murine sequences, PUMA1 has now been humanized by recombinant fusion of the CDRs with human IgG1, IgG2, IgG3 and IgG4 (FIGS. 16A, 16B). An example of the expression of humanized antibodies, while maintaining ability to bind RBCs is shown in FIG. 17.

Figure 14:
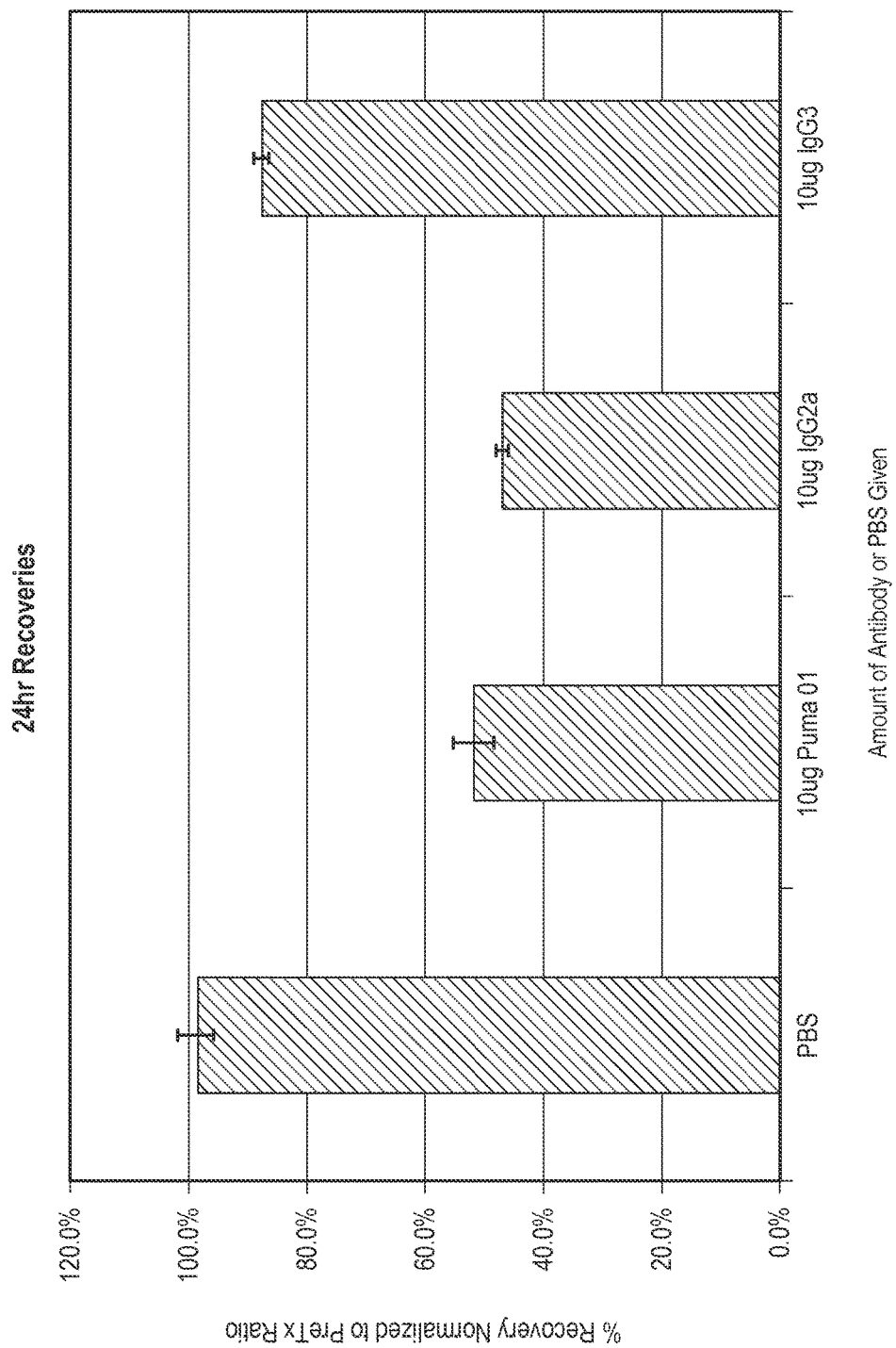
FIG. 14 shows the differential ability of different IgG subclass versions of PUMA 1 to induce a hemolytic transfusion reaction (HTR).
Figure 15:
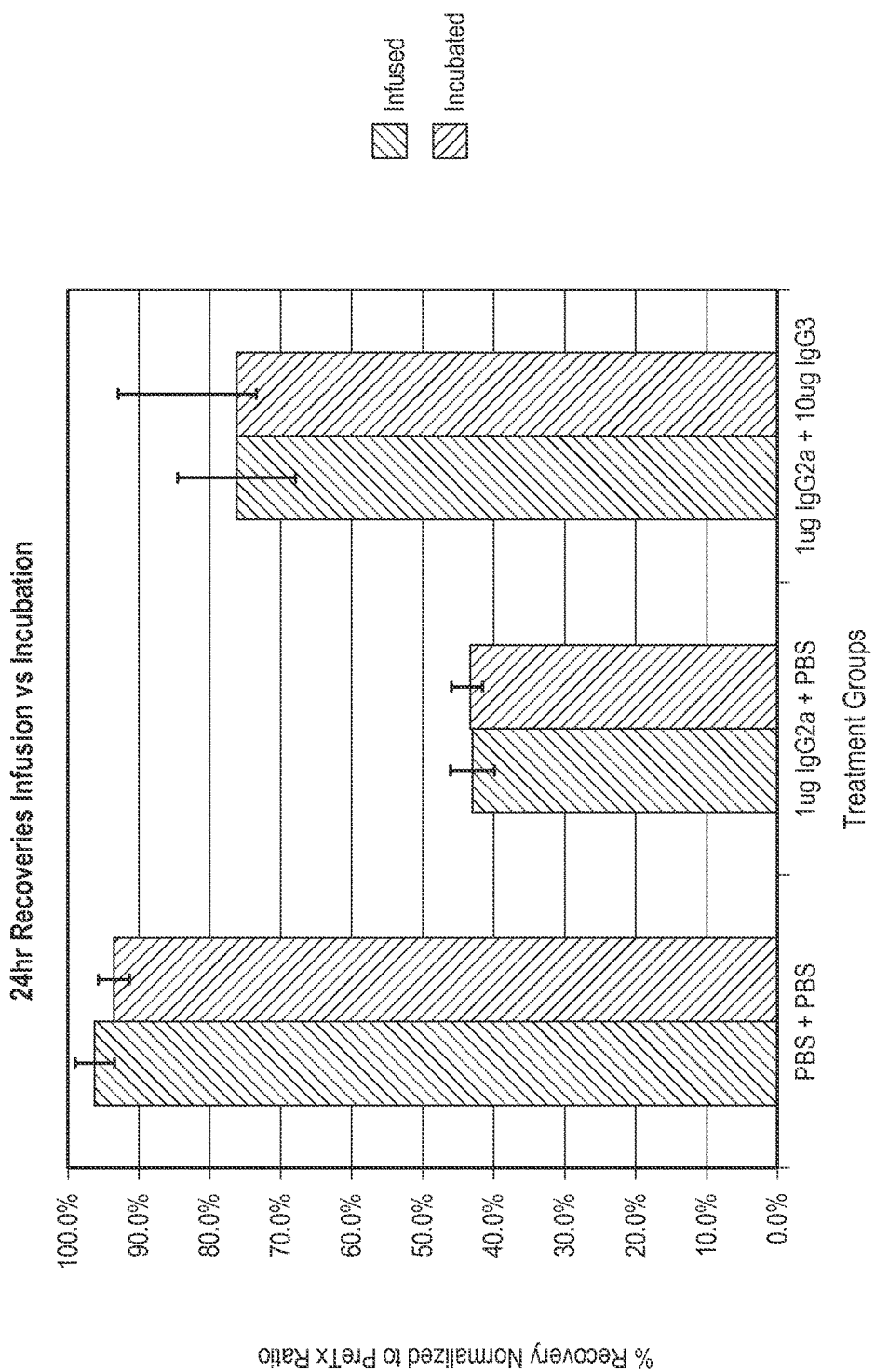
FIG. 15 shows the effect of PUMA 1 IgG3 on blocking hemolysis caused by PUMA 1 IgG2a; these data demonstrate in vivo efficacy, showing the blocking of a HTR by a less hemolytic engineered form.

Example 4: Effect of Modified Antibodies on Clearance of Transfused Red Blood Cells To test the effects of recombinant PUMA1 IgG2a and IgG3 upon transfused RBCs expressing the KEL1 antigen, an equivalent amount of each of the subtypes was injected intravenously into wild-type recipient mice, followed by a transfusion with KEL1+RBCs, and the survival of the KEL1+RBCs was studied over time. Whereas recombinant IgG2a caused clearance of KEL1 RBCs (similar to the hybridoma derived PUMA1 IgG2a, recombinant PUMA1 IgG3 caused only a small amount of clearance (FIG. 14). To test if the IgG3 had the ability to block hemolysis caused by IgG2a, recipient mice were infused first with the hemolytic form of PUMA1 (IgG2a) and were then infused with the less hemolytic form (IgG3), followed by a transfusion with KEL1+ RBCs (FIG. 15—blue (left) bars). Alternatively, PUMA1 IgG3 was added to the RBC unit of KEL1+ RBCs prior to transfusion into a recipient pre-immunized with PUMA1 IgG2a (FIG. 15—red (right) bars). In either case, the addition of an excess of PUMA1 IgG3 decreased the clearance seen with IgG2a to the levels typically seen with IgG3. These data demonstrate that injection of a form of anti-KEL1 with diminished capacity to remove KEL1+ RBCs can reverse the effects of pre-existing hemolytic PUMA1 antibodies.

Together, the data presented herein demonstrate the efficacy of using a less hemolytic form of an antibody to an RBC antigen to prevent clearance of transfused RBCs by a more hemolytic form. The efficacy of this approach is achievable either by directly injecting the blocking antibody into the recipient, prior to transfusion with incompatible RBCs, or by pre-incubating the RBCs with antibody before transfusing. The former approach has the theoretical advantage that pre-incubation with RBCs is not a requirement, and thus is a more rapid treatment in urgent situations. The latter approach, of pre-incubation, may be advantageous (when time allows) due to the ability of blocking antibody to equilibrate with the antigen on the offending RBCs. However, the pre-incubation approach also runs the risk of inducing agglutination of the antigen positive RBCs (likely a variable issue on an antigen by antigen and antibody by antibody basis). While agglutination does not appear to be a risk in the current experimental system, this can be empirically tested on a range of human RBC units for any given antigen/antibody pair to assess if it is a problem. Should agglutination be a problem, it can be likely remedied either by pre-injecting antibody into the recipient, or in extreme cases, by the engineering of monovalent antigen binding molecules.

Example 5: Further Engineering of HTR Blocking Antibodies

As shown above, we have isolated an anti-KEL1 monoclonal antibody sequence. We have performed recombinant manipulation of the antibody to switch the constant region for a less hemolytic form, which results in a therapeutic that can interfere with a HTR, either by injecting into the recipient, or through pre-incubation with the transfused RBCs. Recombinant manipulation of the antibody to switch the constant region for a less hemolytic form results in a therapeutic that can interfere with a HTR, either by injecting into the recipient, or through pre-incubation with the transfused RBCs.

Based on the foregoing which demonstrate efficacy of the approach, and our demonstration of successful humanization (see FIGS. 16A, 16B, and 17), one may introduce additional modifications of the PUMA1 heavy and light chains which include the following: modification of the Fc domain to eliminate effector function (e.g. removing FcgR binding activity and complement fixing activity); addition of in frame domains to prevent and/or suppress immune responses; and addition of chemical moieties to prevent and/or suppress immune responses.

While specific aspects of the invention have been described and illustrated, such aspects should be considered illustrative of the invention only and not as limiting the invention as construed in accordance with the accompanying claims.

All publications and patent applications cited in this specification are herein incorporated by reference in their entirety for all purposes as if each individual publication or patent application were specifically and individually indicated to be incorporated by reference for all purposes.

Although the foregoing invention has been described in some detail by way of illustration and example for purposes of clarity of understanding, it will be readily apparent to one of ordinary skill in the art in light of the teachings of this invention that certain changes and modifications can be made thereto without departing from the spirit or scope of the appended claims.

What is claimed:

1. An isolated antibody or fragment thereof that binds to a Kell blood group antigen KEL1 (K) and blocks a hemolytic transfusion reaction, which isolated antibody or fragment thereof comprises:
   a heavy chain comprising:
      CDR1 shown in SEQ ID NO: 25,
      CDR2 shown in SEQ ID NO: 26, and
      CDR3 shown in SEQ ID NO: 27;
   and
   a light chain comprising:
      CDR1 shown in SEQ ID NO: 28,
      CDR2 shown in SEQ ID NO: 29, and
      CDR3 shown in SEQ ID NO: 30.

2. The antibody or fragment of claim 1, wherein the antibody or fragment recognizes a single amino acid polymorphism.

3. The antibody or fragment thereof according to claim 1, wherein the antibody or fragment thereof is selected from the group consisting of: (a) a whole immunoglobulin molecule; (b) an scFv; (c) a Fab fragment; (d) an F(ab')$_2$; and (e) a disulfide linked Fv.

4. The antibody or fragment thereof according to claim 1, which comprises a heavy chain immunoglobulin constant domain selected from the group consisting of: (a) a human IgM constant domain; (b) a human IgG1 constant domain; (c) a human IgG2 constant domain; (d) a human IgG3 constant domain; (e) a human IgG4 constant domain; and (f) a human IgA1/2 constant domain.

5. The antibody or fragment thereof according to claim 1, which comprises a light chain immunoglobulin constant domain selected from the group consisting of: (a) a human Ig kappa constant domain; and (b) a human Ig lambda constant domain.

6. The antibody or fragment thereof according to claim 1, wherein the antibody or fragment thereof is a mouse IgG1, IgG2a, IgG2b, IgG2c, or IgG3.

7. The antibody or fragment thereof according to claim 1, wherein the antibody or fragment thereof binds to an antigen with an affinity constant ($K_D$) of less than $1 \times 10^{-8}$ M.

8. The antibody or fragment thereof according to claim 1, wherein the heavy chain comprises SEQ ID NO: 1.

9. The antibody or fragment thereof according to claim 1, wherein the light chain comprises SEQ ID NO: 5.

10. The antibody or fragment thereof according to claim 1, wherein the heavy chain is selected from SEQ ID NOs: 21-24.

11. The antibody or fragment thereof according to claim 6, wherein the antibody or fragment thereof is a mouse IgG2a.

12. The antibody or fragment thereof according to claim 6, wherein the antibody or fragment thereof is a mouse IgG3.

13. The antibody or fragment thereof according to claim 1, wherein the heavy chain further comprises modification of Fc domain to eliminate effector function.

14. The antibody or fragment thereof according to claim 1, wherein the heavy chain and/or light chain comprise in frame domains to suppress immune responses.

15. The antibody or fragment thereof according to claim 1, wherein the heavy chain and/or light chain comprise chemical moieties to suppress immune responses.

* * * * *

SEQUENCE LISTING

<160> NUMBER OF SEQ ID NOS: 42

<210> SEQ ID NO 1
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Lys Trp Val Lys Gln Ser His Gly Lys Ser Leu Glu Trp Ile
        35                  40                  45

Gly Asp Leu Asn Pro Asn Asn Gly Asp Thr Phe Tyr Asn Gln Lys Phe
    50                  55                  60

Lys Gly Lys Ala Thr Leu Thr Val Asp Lys Ser Ser Ser Thr Ala Tyr
65                  70                  75                  80

```
Ile Gln Leu Asn Ser Leu Thr Ser Glu Asp Ser Ala Val Tyr Tyr Cys
                85                  90                  95

Ala Arg Glu Ala Gly Ser Ser Phe Gly Ser Ser Cys Asn Tyr Trp Gly
            100                 105                 110

Gln Gly Thr Thr Leu Thr Val Ser
        115                 120

<210> SEQ ID NO 2
<211> LENGTH: 561
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(558)

<400> SEQUENCE: 2 atg tcc tct cca cag aca ctg aac aca ctg act cca acc atg gga tgg        48
Met Ser Ser Pro Gln Thr Leu Asn Thr Leu Thr Pro Thr Met Gly Trp
1               5                   10                  15 agc tgg atc ttt ctc ttt ctc ttg tca gga act gga ggt gtc ctc tct        96
Ser Trp Ile Phe Leu Phe Leu Leu Ser Gly Thr Gly Gly Val Leu Ser
            20                  25                  30 gag gtc caa ctg caa cag tct gga cct gag ctg gtg aag cct ggg gct       144
Glu Val Gln Leu Gln Gln Ser Gly Pro Glu Leu Val Lys Pro Gly Ala
        35                  40                  45 tca gtg aag atg tcc tgc aag gct tct gga tac acc ttc act gac tac       192
Ser Val Lys Met Ser Cys Lys Ala Ser Gly Tyr Thr Phe Thr Asp Tyr
    50                  55                  60 tac atg aag tgg gtg aag cag agc cat ggg aag agc ctt gag tgg att       240
Tyr Met Lys Trp Val Lys Gln Ser His Gly Lys Ser Leu Glu Trp Ile
65                  70                  75                  80 gga gat ctt aat cct aac aat ggt gat act ttc tac aac cag aag ttc       288
Gly Asp Leu Asn Pro Asn Asn Gly Asp Thr Phe Tyr Asn Gln Lys Phe
                85                  90                  95 aag ggc aag gcc aca ttg act gta gac aag tcc tcc agc aca gcc tac       336
Lys Gly Lys Ala Thr Leu Thr Val Asp Lys Ser Ser Ser Thr Ala Tyr
            100                 105                 110 atc cag ctc aac agc ctg aca tct gag gac tct gca gtc tat tac tgt       384
Ile Gln Leu Asn Ser Leu Thr Ser Glu Asp Ser Ala Val Tyr Tyr Cys
        115                 120                 125 gca aga gag gcg gga agt tcc ttc ggt agt agc tgt aat tat tgg ggc       432
Ala Arg Glu Ala Gly Ser Ser Phe Gly Ser Ser Cys Asn Tyr Trp Gly
    130                 135                 140 caa ggc acc act ctc aca gtc tcc tca gcc aaa aca acg gcc cca tct       480
Gln Gly Thr Thr Leu Thr Val Ser Ser Ala Lys Thr Thr Ala Pro Ser
145                 150                 155                 160 gtc tat cca ctg gcc aat cga att ccc gcg gcc gcc atg gcg gcc ggg       528
Val Tyr Pro Leu Ala Asn Arg Ile Pro Ala Ala Ala Met Ala Ala Gly
                165                 170                 175 agc atg cga cgt cgg gcc caa ttc gcc cta tag                           561
Ser Met Arg Arg Arg Ala Gln Phe Ala Leu
            180                 185

<210> SEQ ID NO 3
<211> LENGTH: 186
<212> TYPE: PRT
<213> ORGANISM: Artificial Sequence
<220> FEATURE:
<223> OTHER INFORMATION: Synthetic Construct
```

<400> SEQUENCE: 3

Met Ser Ser Pro Gln Thr Leu Asn Thr Leu Thr Pro Thr Met Gly Trp
1               5                   10                  15

Ser Trp Ile Phe Leu Phe Leu Leu Ser Gly Thr Gly Gly Val Leu Ser
            20                  25                  30

Glu Val Gln Leu Gln Gln Ser Gly Pro Glu Leu Val Lys Pro Gly Ala
        35                  40                  45

Ser Val Lys Met Ser Cys Lys Ala Ser Gly Tyr Thr Phe Thr Asp Tyr
    50                  55                  60

Tyr Met Lys Trp Val Lys Gln Ser His Gly Lys Ser Leu Glu Trp Ile
65                  70                  75                  80

Gly Asp Leu Asn Pro Asn Asn Gly Asp Thr Phe Tyr Asn Gln Lys Phe
                85                  90                  95

Lys Gly Lys Ala Thr Leu Thr Val Asp Lys Ser Ser Thr Ala Tyr
            100                 105                 110

Ile Gln Leu Asn Ser Leu Thr Ser Glu Asp Ser Ala Val Tyr Tyr Cys
        115                 120                 125

Ala Arg Glu Ala Gly Ser Ser Phe Gly Ser Ser Cys Asn Tyr Trp Gly
    130                 135                 140

Gln Gly Thr Thr Leu Thr Val Ser Ser Ala Lys Thr Thr Ala Pro Ser
145                 150                 155                 160

Val Tyr Pro Leu Ala Asn Arg Ile Pro Ala Ala Met Ala Ala Gly
                165                 170                 175

Ser Met Arg Arg Arg Ala Gln Phe Ala Leu
            180                 185

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ccatctgtct atccactggc c                                             21

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Val Val Met Thr Gln Thr Pro Lys Phe Leu Leu Val Ser Ala Gly
1               5                   10                  15

Asp Arg Val Thr Ile Thr Cys Lys Ala Ser Gln Thr Val Ser Lys Asp
            20                  25                  30

Val Ala Trp Tyr Gln Gln Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
                100                 105

<210> SEQ ID NO 6
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(708)
<220> FEATURE:
<221> NAME/KEY: modified_base
<222> LOCATION: (697)..(697)
<223> OTHER INFORMATION: a, c, t, g, unknown or other
<220> FEATURE:
<221> NAME/KEY: misc_feature
<222> LOCATION: (697)..(697)
<223> OTHER INFORMATION: n is a, c, g, or t

<400> SEQUENCE: 6

| | | | | | | | | | | | | | | | | |
|---|---|---|---|---|---|---|---|---|---|---|---|---|---|---|---|---|
| atg | aag | tca | cag | acc | cag | gtc | ttc | gta | ttt | cta | ctg | ctc | tgt | gtg | tct | 48 |
| Met | Lys | Ser | Gln | Thr | Gln | Val | Phe | Val | Phe | Leu | Leu | Leu | Cys | Val | Ser | |
| 1 | | | | 5 | | | | | 10 | | | | | 15 | | |
| gga | gtt | cat | ggg | agt | gtt | gtg | atg | acc | cag | act | ccc | aag | ttc | ctg | ctt | 96 |
| Gly | Val | His | Gly | Ser | Val | Val | Met | Thr | Gln | Thr | Pro | Lys | Phe | Leu | Leu | |
| | | | 20 | | | | | 25 | | | | | 30 | | | |
| gtg | tca | gcg | gga | gac | agg | gtt | acc | ata | acc | tgc | aag | gcc | agt | cag | act | 144 |
| Val | Ser | Ala | Gly | Asp | Arg | Val | Thr | Ile | Thr | Cys | Lys | Ala | Ser | Gln | Thr | |
| | | 35 | | | | | 40 | | | | | 45 | | | | |
| gtg | agt | aaa | gat | gta | gct | tgg | tac | caa | cag | cag | cca | ggg | cag | tct | cct | 192 |
| Val | Ser | Lys | Asp | Val | Ala | Trp | Tyr | Gln | Gln | Gln | Pro | Gly | Gln | Ser | Pro | |
| | 50 | | | | | 55 | | | | | 60 | | | | | |
| aaa | ctg | ctg | ata | tac | tat | gca | tcc | aat | cgc | tac | act | gga | gtc | cct | gat | 240 |
| Lys | Leu | Leu | Ile | Tyr | Tyr | Ala | Ser | Asn | Arg | Tyr | Thr | Gly | Val | Pro | Asp | |
| 65 | | | | | 70 | | | | | 75 | | | | | 80 | |
| cgc | ttc | act | ggc | agt | gga | tat | ggg | acg | gat | ttc | act | ttc | acc | atc | agc | 288 |
| Arg | Phe | Thr | Gly | Ser | Gly | Tyr | Gly | Thr | Asp | Phe | Thr | Phe | Thr | Ile | Ser | |
| | | | | 85 | | | | | 90 | | | | | 95 | | |
| act | gtg | cag | gct | gaa | gac | ctg | gca | gtt | tat | ttc | tgt | cag | cag | gat | tat | 336 |
| Thr | Val | Gln | Ala | Glu | Asp | Leu | Ala | Val | Tyr | Phe | Cys | Gln | Gln | Asp | Tyr | |
| | | | 100 | | | | | 105 | | | | | 110 | | | |
| agc | tct | ccg | tac | acg | ttc | ggc | ggg | ggg | acc | aag | ctg | gaa | ata | aaa | cgg | 384 |
| Ser | Ser | Pro | Tyr | Thr | Phe | Gly | Gly | Gly | Thr | Lys | Leu | Glu | Ile | Lys | Arg | |
| | | 115 | | | | | 120 | | | | | 125 | | | | |
| gct | gat | gct | gca | cca | act | gta | tcc | atc | ttc | cca | cca | tcc | agt | gag | cag | 432 |
| Ala | Asp | Ala | Ala | Pro | Thr | Val | Ser | Ile | Phe | Pro | Pro | Ser | Ser | Glu | Gln | |
| | 130 | | | | | 135 | | | | | 140 | | | | | |
| tta | aca | tct | gga | ggt | gcc | tca | gtc | gtg | tgc | ttc | ttg | aac | aac | ttc | tac | 480 |
| Leu | Thr | Ser | Gly | Gly | Ala | Ser | Val | Val | Cys | Phe | Leu | Asn | Asn | Phe | Tyr | |
| 145 | | | | | 150 | | | | | 155 | | | | | 160 | |
| ccc | aga | gac | atc | aat | gtc | aag | tgg | aag | att | gat | ggc | agt | gaa | cga | caa | 528 |
| Pro | Arg | Asp | Ile | Asn | Val | Lys | Trp | Lys | Ile | Asp | Gly | Ser | Glu | Arg | Gln | |
| | | | | 165 | | | | | 170 | | | | | 175 | | |
| aat | ggt | gtc | ctg | aac | agt | tgg | act | gat | cag | gac | agc | aaa | gac | agc | acc | 576 |
| Asn | Gly | Val | Leu | Asn | Ser | Trp | Thr | Asp | Gln | Asp | Ser | Lys | Asp | Ser | Thr | |
| | | | 180 | | | | | 185 | | | | | 190 | | | |
| tac | agc | atg | agc | agc | acc | ctc | aca | ttg | acc | aag | gac | gag | tat | gaa | cga | 624 |
| Tyr | Ser | Met | Ser | Ser | Thr | Leu | Thr | Leu | Thr | Lys | Asp | Glu | Tyr | Glu | Arg | |
| | | 195 | | | | | 200 | | | | | 205 | | | | |
| cat | aac | agc | tat | acc | tgt | gag | gcc | act | cac | aag | aca | tca | act | tca | ccc | 672 |

```
His Asn Ser Tyr Thr Cys Glu Ala Thr His Lys Thr Ser Thr Ser Pro
    210                 215                 220 atc gtc aag agc ttc aac agg aat nag tgt aat cac tag              711
Ile Val Lys Ser Phe Asn Arg Asn Xaa Cys Asn His
225                 230                 235
```

<210> SEQ ID NO 7
<211> LENGTH: 236
<212> TYPE: PRT
<213> ORGANISM: Artificial Sequence
<220> FEATURE:
<221> NAME/KEY: misc_feature
<222> LOCATION: (233)..(233)
<223> OTHER INFORMATION: The 'Xaa' at location 233 stands for Lys, Glu, or Gln.
<220> FEATURE:
<223> OTHER INFORMATION: Synthetic Construct

<400> SEQUENCE: 7

```
Met Lys Ser Gln Thr Gln Val Phe Val Phe Leu Leu Leu Cys Val Ser
1               5                   10                  15

Gly Val His Gly Ser Val Val Met Thr Gln Thr Pro Lys Phe Leu Leu
                20                  25                  30

Val Ser Ala Gly Asp Arg Val Thr Ile Thr Cys Lys Ala Ser Gln Thr
            35                  40                  45

Val Ser Lys Asp Val Ala Trp Tyr Gln Gln Pro Gly Gln Ser Pro
50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Xaa Cys Asn His
225                 230                 235
```

<210> SEQ ID NO 8
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Gln Val Gln Leu Lys Glu Ser Gly Pro Gly Leu Leu Ala Pro Ser Gln
```

```
            1               5                   10                  15
Ser Leu Ser Ile Thr Cys Thr Val Ser Gly Phe Ser Leu Thr Ser Tyr
              20                  25                  30

Gly Val Tyr Trp Val Arg Gln Pro Pro Gly Lys Gly Leu Glu Trp Leu
          35                  40                  45

Gly Ile Ile Trp Gly Asp Gly Ser Thr Asn Tyr Gln Ser Val Leu Arg
      50                  55                  60

Ser Arg Leu Ser Ile Thr Lys Asp Asp Ser Lys Ser Gln Val Phe Leu
 65                  70                  75                  80

Lys Leu Asn Ser Leu Gln Thr Asp Asp Thr Ala Thr Tyr Tyr Cys Ala
                  85                  90                  95

Lys Arg Gly Asp Tyr Asp Val Ala Tyr Trp Gly Gln Gly Thr Leu Val
              100                 105                 110

Thr Val Ser Ala
      115
```

<210> SEQ ID NO 9
<211> LENGTH: 450
<212> TYPE: DNA
<213> ORGANISM: Artificial Sequence
<220> FEATURE:
<223> OTHER INFORMATION: Description of Artificial Sequence: Synthetic
     polynucleotide
<220> FEATURE:
<221> NAME/KEY: CDS
<222> LOCATION: (1)..(447)
<220> FEATURE:
<221> NAME/KEY: modified_base
<222> LOCATION: (436)..(437)
<223> OTHER INFORMATION: a, c, t, g, unknown or other
<220> FEATURE:
<221> NAME/KEY: misc_feature
<222> LOCATION: (436)..(437)
<223> OTHER INFORMATION: n is a, c, g, or t
<220> FEATURE:
<221> NAME/KEY: modified_base
<222> LOCATION: (440)..(440)
<223> OTHER INFORMATION: a, c, t, g, unknown or other
<220> FEATURE:
<221> NAME/KEY: misc_feature
<222> LOCATION: (440)..(440)
<223> OTHER INFORMATION: n is a, c, g, or t

<400> SEQUENCE: 9

```
atg gct gtc ctg gca ctg ctc ctc tgc ctg gtg aca ttc cca agg tgt     48
Met Ala Val Leu Ala Leu Leu Leu Cys Leu Val Thr Phe Pro Arg Cys
 1               5                   10                  15 gtc ctg tcc cag gtg cag ctg aag gag tca gga cct ggc cta ctg gcg     96
Val Leu Ser Gln Val Gln Leu Lys Glu Ser Gly Pro Gly Leu Leu Ala
              20                  25                  30 ccc tca cag agc ctg tcc atc aca tgc act gtc tca ggt ttc tcg tta    144
Pro Ser Gln Ser Leu Ser Ile Thr Cys Thr Val Ser Gly Phe Ser Leu
          35                  40                  45 acc agc tat ggt gta tac tgg gtt cgc cag cct cca gga aag ggt ctg    192
Thr Ser Tyr Gly Val Tyr Trp Val Arg Gln Pro Pro Gly Lys Gly Leu
      50                  55                  60 gag tgg ctg gga atc ata tgg ggt gac ggg agc aca aat tat caa tca    240
Glu Trp Leu Gly Ile Ile Trp Gly Asp Gly Ser Thr Asn Tyr Gln Ser
 65                  70                  75                  80 gtt ctc aga tcc aga ctg agc atc acc aag gat gac tcc aag agc caa    288
Val Leu Arg Ser Arg Leu Ser Ile Thr Lys Asp Asp Ser Lys Ser Gln
                  85                  90                  95 gtt ttc tta aaa ctg aac agt cta caa act gat gac aca gcc acg tac    336
Val Phe Leu Lys Leu Asn Ser Leu Gln Thr Asp Asp Thr Ala Thr Tyr
```

```
                        100                 105                 110
tac tgt gcc aaa cgg ggg gat tac gac gtt gct tac tgg ggc caa ggg    384
Tyr Cys Ala Lys Arg Gly Asp Tyr Asp Val Ala Tyr Trp Gly Gln Gly
            115                 120                 125 act ctg gtc act gtc tct gca gcc aaa acg aca ccc cca tct gtc tat    432
Thr Leu Val Thr Val Ser Ala Ala Lys Thr Thr Pro Pro Ser Val Tyr
    130                 135                 140 cct nna gnc aat cac tag                                             450
Pro Xaa Xaa Asn His
145

<210> SEQ ID NO 10
<211> LENGTH: 149
<212> TYPE: PRT
<213> ORGANISM: Artificial Sequence
<220> FEATURE:
<221> NAME/KEY: misc_feature
<222> LOCATION: (146)..(146)
<223> OTHER INFORMATION: The 'Xaa' at location 146 stands for Lys, Arg,
      Thr, Ile, Glu, Gly, Ala, Val, Gln, Pro, Leu, or Ser.
<220> FEATURE:
<221> NAME/KEY: misc_feature
<222> LOCATION: (147)..(147)
<223> OTHER INFORMATION: The 'Xaa' at location 147 stands for Asp, Gly,
      Ala, or Val.
<220> FEATURE:
<223> OTHER INFORMATION: Synthetic Construct

<400> SEQUENCE: 10

Met Ala Val Leu Ala Leu Leu Cys Leu Val Thr Phe Pro Arg Cys
1               5                   10                  15

Val Leu Ser Gln Val Gln Leu Lys Glu Ser Gly Pro Gly Leu Leu Ala
            20                  25                  30

Pro Ser Gln Ser Leu Ser Ile Thr Cys Thr Val Ser Gly Phe Ser Leu
        35                  40                  45

Thr Ser Tyr Gly Val Tyr Trp Val Arg Gln Pro Pro Gly Lys Gly Leu
    50                  55                  60

Glu Trp Leu Gly Ile Ile Trp Gly Asp Gly Ser Thr Asn Tyr Gln Ser
65                  70                  75                  80

Val Leu Arg Ser Arg Leu Ser Ile Thr Lys Asp Asp Ser Lys Ser Gln
                85                  90                  95

Val Phe Leu Lys Leu Asn Ser Leu Gln Thr Asp Asp Thr Ala Thr Tyr
            100                 105                 110

Tyr Cys Ala Lys Arg Gly Asp Tyr Asp Val Ala Tyr Trp Gly Gln Gly
        115                 120                 125

Thr Leu Val Thr Val Ser Ala Ala Lys Thr Thr Pro Pro Ser Val Tyr
    130                 135                 140

Pro Xaa Xaa Asn His
145

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ccatctgtct at                                                       12

<210> SEQ ID NO 12
```

<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Val Leu Thr Gln Ser Pro Ala Ser Leu Ala Val Ser Leu Gly
1               5                   10                  15

Gln Arg Ala Ile Ile Ser Cys Lys Ala Ser Gln Thr Val Ser Glu Val
            20                  25                  30

Gly Thr Ser Leu Met His Trp Tyr Gln Gln Arg Pro Gly Gln Gln Pro
        35                  40                  45

Lys Leu Leu Ile Tyr Arg Thr Ser Asn Leu Glu Ala Gly Val Pro Thr
    50                  55                  60

Arg Phe Ser Gly Ser Gly Ser Arg Thr Asp Phe Thr Leu Asn Ile His
65                  70                  75                  80

Pro Val Glu Glu Asp Asp Ala Ala Thr Tyr Tyr Cys Gln Gln Ser Arg
                85                  90                  95

Glu Phe Pro Trp Thr Phe Gly Gly Gly Thr Arg Leu Glu Ile Lys
            100                 105                 110

<210> SEQ ID NO 13
<211> LENGTH: 723
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(720)
<220> FEATURE:
<221> NAME/KEY: modified_base
<222> LOCATION: (5)..(5)
<223> OTHER INFORMATION: a, c, t, g, unknown or other
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: modified_base
<222> LOCATION: (12)..(12)
<223> OTHER INFORMATION: a, c, t, g, unknown or other
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: modified_base
<222> LOCATION: (15)..(15)
<223> OTHER INFORMATION: a, c, t, g, unknown or other
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: modified_base
<222> LOCATION: (24)..(24)
<223> OTHER INFORMATION: a, c, t, g, unknown or other
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: modified_base
<222> LOCATION: (26)..(27)
<223> OTHER INFORMATION: a, c, t, g, unknown or other
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: modified_base
<222> LOCATION: (665)..(665)
<223> OTHER INFORMATION: a, c, t, g, unknown or other
<220> FEATURE:
<221> NAME/KEY: misc_feature
<222> LOCATION: (665)..(665)
<223> OTHER INFORMATION: n is a, c, g, or t

<400> SEQUENCE: 13

| | | | | | | | | | | | | | | | | |
|---|---|---|---|---|---|---|---|---|---|---|---|---|---|---|---|---|
| atg | gng | act | can | tcn | ctg | ctg | ctn | tnn | gtg | cta | ctg | ctc | tgg | gtt | cca | 48 |
| Met | Xaa | Thr | Xaa | Xaa | Leu | Leu | Xaa | Xaa | Val | Leu | Leu | Leu | Trp | Val | Pro | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | tcc | act | ggt | gac | att | gtg | ctg | acc | caa | tct | cca | gct | tct | ttg | gct | 96 |
| Gly | Ser | Thr | Gly | Asp | Ile | Val | Leu | Thr | Gln | Ser | Pro | Ala | Ser | Leu | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| gtg | tct | cta | ggg | cag | agg | gcc | atc | atc | tcc | tgc | aag | gcc | agc | caa | act | 144 |
| Val | Ser | Leu | Gly | Gln | Arg | Ala | Ile | Ile | Ser | Cys | Lys | Ala | Ser | Gln | Thr | |
| | | 35 | | | | | 40 | | | | | 45 | | | | |

| | | | | | | | | | | | | | | | | |
|---|---|---|---|---|---|---|---|---|---|---|---|---|---|---|---|---|
| gtc | agt | ttt | gtt | ggg | act | agt | tta | atg | cac | tgg | tat | caa | cag | aga | cca | 192 |
| Val | Ser | Phe | Val | Gly | Thr | Ser | Leu | Met | His | Trp | Tyr | Gln | Gln | Arg | Pro | |
| 50 | | | | | 55 | | | | | 60 | | | | | | |

| | | | | | | | | | | | | | | | | |
|---|---|---|---|---|---|---|---|---|---|---|---|---|---|---|---|---|
| gga | cag | caa | ccc | aaa | ctc | ctc | atc | tat | cgt | aca | tcc | aac | cta | gaa | gct | 240 |
| Gly | Gln | Gln | Pro | Lys | Leu | Leu | Ile | Tyr | Arg | Thr | Ser | Asn | Leu | Glu | Ala | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ggg | gtt | cca | acc | agg | ttt | agt | ggc | agt | ggg | tct | agg | aca | gac | ttc | acc | 288 |
| Gly | Val | Pro | Thr | Arg | Phe | Ser | Gly | Ser | Gly | Ser | Arg | Thr | Asp | Phe | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| ctc | aat | atc | cat | cct | gtg | gag | gaa | gat | gat | gct | gca | acc | tat | tac | tgt | 336 |
| Leu | Asn | Ile | His | Pro | Val | Glu | Glu | Asp | Asp | Ala | Ala | Thr | Tyr | Tyr | Cys | |
| | | | 100 | | | | | 105 | | | | | 110 | | | |

| | | | | | | | | | | | | | | | | |
|---|---|---|---|---|---|---|---|---|---|---|---|---|---|---|---|---|
| cag | caa | agt | agg | gaa | ttt | ccg | tgg | acg | ttc | ggt | gga | ggc | acc | agg | ctg | 384 |
| Gln | Gln | Ser | Arg | Glu | Phe | Pro | Trp | Thr | Phe | Gly | Gly | Gly | Thr | Arg | Leu | |
| | | 115 | | | | | 120 | | | | | 125 | | | | |

| | | | | | | | | | | | | | | | | |
|---|---|---|---|---|---|---|---|---|---|---|---|---|---|---|---|---|
| gaa | atc | aaa | cgg | gct | gat | gct | gca | cca | act | gta | tcc | atc | ttc | cca | cca | 432 |
| Glu | Ile | Lys | Arg | Ala | Asp | Ala | Ala | Pro | Thr | Val | Ser | Ile | Phe | Pro | Pro | |
| 130 | | | | | 135 | | | | | 140 | | | | | | |

| | | | | | | | | | | | | | | | | |
|---|---|---|---|---|---|---|---|---|---|---|---|---|---|---|---|---|
| tcc | agt | gag | cag | tta | aca | tct | gga | ggt | gcc | tca | gtc | gtg | tgc | ttc | ttg | 480 |
| Ser | Ser | Glu | Gln | Leu | Thr | Ser | Gly | Gly | Ala | Ser | Val | Val | Cys | Phe | Leu | |
| 145 | | | | 150 | | | | | 155 | | | | | 160 | | |

| | | | | | | | | | | | | | | | | |
|---|---|---|---|---|---|---|---|---|---|---|---|---|---|---|---|---|
| aac | aac | ttc | tac | ccc | aga | gac | atc | aat | gtc | aag | tgg | aag | att | gat | ggc | 528 |
| Asn | Asn | Phe | Tyr | Pro | Arg | Asp | Ile | Asn | Val | Lys | Trp | Lys | Ile | Asp | Gly | |
| | | | | 165 | | | | | 170 | | | | | 175 | | |

| | | | | | | | | | | | | | | | | |
|---|---|---|---|---|---|---|---|---|---|---|---|---|---|---|---|---|
| agt | gaa | cga | caa | aat | ggt | gtc | ctg | aac | agt | tgg | act | gat | cag | gac | agc | 576 |
| Ser | Glu | Arg | Gln | Asn | Gly | Val | Leu | Asn | Ser | Trp | Thr | Asp | Gln | Asp | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| aaa | gac | agc | acc | tac | agc | atg | agc | agc | acc | ctc | aca | ttg | acc | aag | gac | 624 |
| Lys | Asp | Ser | Thr | Tyr | Ser | Met | Ser | Ser | Thr | Leu | Thr | Leu | Thr | Lys | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| gag | tat | gaa | cga | cat | aac | agc | tat | acc | tgt | gag | gcc | act | cnc | aag | aca | 672 |
| Glu | Tyr | Glu | Arg | His | Asn | Ser | Tyr | Thr | Cys | Glu | Ala | Thr | Xaa | Lys | Thr | |
| 210 | | | | | 215 | | | | | 220 | | | | | | |

| | | | | | | | | | | | | | | | | |
|---|---|---|---|---|---|---|---|---|---|---|---|---|---|---|---|---|
| tca | act | tca | ccc | atc | gtc | aag | agc | ttc | aac | agg | aat | gag | tgt | aat | cac | 720 |
| Ser | Thr | Ser | Pro | Ile | Val | Lys | Ser | Phe | Asn | Arg | Asn | Glu | Cys | Asn | His | |
| 225 | | | | 230 | | | | | 235 | | | | | 240 | | |

| | |
|---|---|
| tag | 723 |

<210> SEQ ID NO 14
<211> LENGTH: 240
<212> TYPE: PRT

```
<213> ORGANISM: Artificial Sequence
<220> FEATURE:
<221> NAME/KEY: misc_feature
<222> LOCATION: (2)..(2)
<223> OTHER INFORMATION: The 'Xaa' at location 2 stands for Glu, Gly,
      Ala, or Val.
<220> FEATURE:
<221> NAME/KEY: misc_feature
<222> LOCATION: (4)..(4)
<223> OTHER INFORMATION: The 'Xaa' at location 4 stands for Gln, or His.
<220> FEATURE:
<221> NAME/KEY: misc_feature
<222> LOCATION: (5)..(5)
<223> OTHER INFORMATION: The 'Xaa' at location 5 stands for Ser.
<220> FEATURE:
<221> NAME/KEY: misc_feature
<222> LOCATION: (8)..(8)
<223> OTHER INFORMATION: The 'Xaa' at location 8 stands for Leu.
<220> FEATURE:
<221> NAME/KEY: misc_feature
<222> LOCATION: (9)..(9)
<223> OTHER INFORMATION: The 'Xaa' at location 9 stands for Tyr, Trp,
      Cys, Ser, Leu, or Phe.
<220> FEATURE:
<221> NAME/KEY: misc_feature
<222> LOCATION: (222)..(222)
<223> OTHER INFORMATION: The 'Xaa' at location 222 stands for His, Arg,
      Pro, or Leu.
<220> FEATURE:
<223> OTHER INFORMATION: Synthetic Construct

<400> SEQUENCE: 14

Met Xaa Thr Xaa Xaa Leu Leu Xaa Xaa Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Ile Ile Ser Cys Lys Ala Ser Gln Thr
        35                  40                  45

Val Ser Phe Val Gly Thr Ser Leu Met His Trp Tyr Gln Gln Arg Pro
    50                  55                  60

Gly Gln Gln Pro Lys Leu Leu Ile Tyr Arg Thr Ser Asn Leu Glu Ala
65                  70                  75                  80

Gly Val Pro Thr Arg Phe Ser Gly Ser Gly Ser Arg Thr Asp Phe Thr
                85                  90                  95

Leu Asn Ile His Pro Val Glu Glu Asp Asp Ala Ala Thr Tyr Tyr Cys
            100                 105                 110

Gln Gln Ser Arg Glu Phe Pro Trp Thr Phe Gly Gly Gly Thr Arg Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Arg Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr Xaa Lys Thr
    210                 215                 220

Ser Thr Ser Pro Ile Val Lys Ser Phe Asn Arg Asn Glu Cys Asn His
225                 230                 235                 240
```

-continued

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asn Tyr
            20                  25                  30

Trp Met Asn Trp Val Arg Gln Pro Pro Glu Lys Gly Leu Glu Trp Val
        35                  40                  45

Ala Glu Ile Arg Leu Asn Ser Asn Asn Tyr Ala Thr His Tyr Ala Glu
    50                  55                  60

Ser Val Lys Gly Lys Phe Thr Ile Ser Arg Asp Asp Ser Lys Ser Ser
65                  70                  75                  80

Val Tyr Leu Gln Met Asn Asp Leu Arg Ala Glu Asp Thr Gly Ile Tyr
                85                  90                  95

Tyr Cys Thr Arg Asn Trp Asp Phe Ala Trp Phe Asp Ser Trp Gly Gln
            100                 105                 110

Gly Thr Leu Val Thr Val Ser Ala
        115                 120

<210> SEQ ID NO 16
<211> LENGTH: 591
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(588)

<400> SEQUENCE: 16 atg ggg aga cgc aca acc ctg gac tca caa gtc ttt ctc ttc agt gac      48
Met Gly Arg Arg Thr Thr Leu Asp Ser Gln Val Phe Leu Phe Ser Asp
1               5                   10                  15 aaa cac aga aat aga aca ttc acc atg tac ttg gga ctg aac tgt gta      96
Lys His Arg Asn Arg Thr Phe Thr Met Tyr Leu Gly Leu Asn Cys Val
            20                  25                  30 ttc ata gtt ttt ctc tta aaa ggt gtc cag agt gaa gtg aag ctt gag     144
Phe Ile Val Phe Leu Leu Lys Gly Val Gln Ser Glu Val Lys Leu Glu
        35                  40                  45 gag tct gga gga ggc ttg gtg caa cct gga gga tcc atg aaa ctc tcc     192
Glu Ser Gly Gly Gly Leu Val Gln Pro Gly Gly Ser Met Lys Leu Ser
    50                  55                  60 tgt gtt gcc tct gga ttc act ttc agt aac tac tgg atg aac tgg gtc     240
Cys Val Ala Ser Gly Phe Thr Phe Ser Asn Tyr Trp Met Asn Trp Val
65                  70                  75                  80 cgc caa cct cca gag aag ggg ctt gaa tgg gtt gct gaa att aga ttg     288
Arg Gln Pro Pro Glu Lys Gly Leu Glu Trp Val Ala Glu Ile Arg Leu
                85                  90                  95 aac tct aat aat tat gca aca cat tat gcg gag tct gtg aaa ggg aaa     336
Asn Ser Asn Asn Tyr Ala Thr His Tyr Ala Glu Ser Val Lys Gly Lys
            100                 105                 110 ttc acc atc tca aga gat gat tcc aaa agt agt gtc tac ctg caa atg     384
Phe Thr Ile Ser Arg Asp Asp Ser Lys Ser Ser Val Tyr Leu Gln Met
        115                 120                 125

```
aac gac tta aga gct gaa gac act ggc att tat tac tgt acc aga aac    432
Asn Asp Leu Arg Ala Glu Asp Thr Gly Ile Tyr Tyr Cys Thr Arg Asn
    130                 135                 140 tgg gac ttt gcc tgg ttt gat tcc tgg ggc caa ggg act ctg gtc act    480
Trp Asp Phe Ala Trp Phe Asp Ser Trp Gly Gln Gly Thr Leu Val Thr
145                 150                 155                 160 gtc tct gca gcc aaa aca aca gcc cca tct gtc tat cca ctg gcc aat    528
Val Ser Ala Ala Lys Thr Thr Ala Pro Ser Val Tyr Pro Leu Ala Asn
                165                 170                 175 cga att ccc gcg gcc gcc atg gcg gcc ggg agc atg cga cgt cgg gcc    576
Arg Ile Pro Ala Ala Ala Met Ala Ala Gly Ser Met Arg Arg Arg Ala
            180                 185                 190 caa ttc gcc cta tag                                                591
Gln Phe Ala Leu
        195

<210> SEQ ID NO 17
<211> LENGTH: 196
<212> TYPE: PRT
<213> ORGANISM: Artificial Sequence
<220> FEATURE:
<223> OTHER INFORMATION: Synthetic Construct

<400> SEQUENCE: 17

Met Gly Arg Arg Thr Thr Leu Asp Ser Gln Val Phe Leu Phe Ser Asp
1               5                   10                  15

Lys His Arg Asn Arg Thr Phe Thr Met Tyr Leu Gly Leu Asn Cys Val
                20                  25                  30

Phe Ile Val Phe Leu Leu Lys Gly Val Gln Ser Glu Val Lys Leu Glu
            35                  40                  45

Glu Ser Gly Gly Gly Leu Val Gln Pro Gly Gly Ser Met Lys Leu Ser
        50                  55                  60

Cys Val Ala Ser Gly Phe Thr Phe Ser Asn Tyr Trp Met Asn Trp Val
65                  70                  75                  80

Arg Gln Pro Pro Glu Lys Gly Leu Glu Trp Val Ala Glu Ile Arg Leu
                85                  90                  95

Asn Ser Asn Asn Tyr Ala Thr His Tyr Ala Glu Ser Val Lys Gly Lys
                100                 105                 110

Phe Thr Ile Ser Arg Asp Asp Ser Lys Ser Ser Val Tyr Leu Gln Met
            115                 120                 125

Asn Asp Leu Arg Ala Glu Asp Thr Gly Ile Tyr Tyr Cys Thr Arg Asn
    130                 135                 140

Trp Asp Phe Ala Trp Phe Asp Ser Trp Gly Gln Gly Thr Leu Val Thr
145                 150                 155                 160

Val Ser Ala Ala Lys Thr Thr Ala Pro Ser Val Tyr Pro Leu Ala Asn
                165                 170                 175

Arg Ile Pro Ala Ala Ala Met Ala Ala Gly Ser Met Arg Arg Arg Ala
            180                 185                 190

Gln Phe Ala Leu
        195

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 18

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Val
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Tyr Thr Thr Pro Phe
                85                  90                  95

Thr Phe Gly Ser Gly Thr Lys Leu Glu Ile Lys
            100                 105
```

<210> SEQ ID NO 19
<211> LENGTH: 747
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(744)

<400> SEQUENCE: 19

```
atg ggg gaa atg cat cgc acc agc atg ggc atc aag atg gag tca cag       48
Met Gly Glu Met His Arg Thr Ser Met Gly Ile Lys Met Glu Ser Gln
1               5                   10                  15 att cag gca ttt gta ttc gtg ttt ctc tgg ttg tct ggt gtt gac gga       96
Ile Gln Ala Phe Val Phe Val Phe Leu Trp Leu Ser Gly Val Asp Gly
            20                  25                  30 gac att gtg atg acc cag tct cac aaa ttc atg tcc aca tca gta gga      144
Asp Ile Val Met Thr Gln Ser His Lys Phe Met Ser Thr Ser Val Gly
        35                  40                  45 gac agg gtc agc atc acc tgc aag gcc agt caa gat gtg agt act gtt      192
Asp Arg Val Ser Ile Thr Cys Lys Ala Ser Gln Asp Val Ser Thr Val
50                  55                  60 gtg gcc tgg tat caa caa aaa cca ggg caa tct cct aaa cta ctg att      240
Val Ala Trp Tyr Gln Gln Lys Pro Gly Gln Ser Pro Lys Leu Leu Ile
65                  70                  75                  80 tac tgg gca tcc acc cgg cac act gga gtc cct gat cgc ttc aca ggc      288
Tyr Trp Ala Ser Thr Arg His Thr Gly Val Pro Asp Arg Phe Thr Gly
                85                  90                  95 agt gga tct ggg aca gat tat act ctc acc atc agc agt gtg cag gct      336
Ser Gly Ser Gly Thr Asp Tyr Thr Leu Thr Ile Ser Ser Val Gln Ala
            100                 105                 110 gaa gac ctg gca ctt tat tac tgt cag caa cat tat acc act cca ttc      384
Glu Asp Leu Ala Leu Tyr Tyr Cys Gln Gln His Tyr Thr Thr Pro Phe
        115                 120                 125 acg ttc ggc tcg ggg aca aag ttg gaa ata aaa cgg gct gat gct gca      432
Thr Phe Gly Ser Gly Thr Lys Leu Glu Ile Lys Arg Ala Asp Ala Ala
130                 135                 140 cca act gta tcc atc ttc cca cca tcc agt gag cag tta aca tct gga      480
Pro Thr Val Ser Ile Phe Pro Pro Ser Ser Glu Gln Leu Thr Ser Gly
145                 150                 155                 160 ggt gcc tca gtc gtg tgc ttc ttg aac aac ttc tac ccc aga gac atc      528
Gly Ala Ser Val Val Cys Phe Leu Asn Asn Phe Tyr Pro Arg Asp Ile
```

|  |  |  |  |  |  |  |  | 165 |  |  |  |  | 170 |  |  |  |  | 175 |  |  |
|---|---|---|---|---|---|---|---|---|---|---|---|---|---|---|---|---|---|---|---|---|
| aat | gtc | aag | tgg | aag | att | gat | ggc | agt | gaa | cga | caa | aat | ggt | gtc | ctg |  |  |  |  | 576 |
| Asn | Val | Lys | Trp | Lys | Ile | Asp | Gly | Ser | Glu | Arg | Gln | Asn | Gly | Val | Leu |  |  |  |  |  |
|  |  |  | 180 |  |  |  |  | 185 |  |  |  |  | 190 |  |  |  |  |  |  |  |
| aac | agt | tgg | act | gat | cag | gac | agc | aaa | gac | agc | acc | tac | agc | atg | agc |  |  |  |  | 624 |
| Asn | Ser | Trp | Thr | Asp | Gln | Asp | Ser | Lys | Asp | Ser | Thr | Tyr | Ser | Met | Ser |  |  |  |  |  |
|  |  | 195 |  |  |  |  | 200 |  |  |  |  | 205 |  |  |  |  |  |  |  |  |
| agc | acc | ctc | aca | ttg | acc | aag | gac | gag | tat | gaa | cga | cat | aac | agc | tat |  |  |  |  | 672 |
| Ser | Thr | Leu | Thr | Leu | Thr | Lys | Asp | Glu | Tyr | Glu | Arg | His | Asn | Ser | Tyr |  |  |  |  |  |
|  | 210 |  |  |  |  | 215 |  |  |  |  | 220 |  |  |  |  |  |  |  |  |  |
| acc | tgt | gag | gcc | act | cac | aag | aca | tca | act | tca | ccc | atc | gtc | aag | agc |  |  |  |  | 720 |
| Thr | Cys | Glu | Ala | Thr | His | Lys | Thr | Ser | Thr | Ser | Pro | Ile | Val | Lys | Ser |  |  |  |  |  |
| 225 |  |  |  |  | 230 |  |  |  |  | 235 |  |  |  |  | 240 |  |  |  |  |  |
| ttc | aac | agg | aat | gag | tgt | aat | cac | tag |  |  |  |  |  |  |  |  |  |  |  | 747 |
| Phe | Asn | Arg | Asn | Glu | Cys | Asn | His |  |  |  |  |  |  |  |  |  |  |  |  |  |
|  |  |  |  | 245 |  |  |  |  |  |  |  |  |  |  |  |  |  |  |  |  |

<210> SEQ ID NO 20
<211> LENGTH: 248
<212> TYPE: PRT
<213> ORGANISM: Artificial Sequence
<220> FEATURE:
<223> OTHER INFORMATION: Synthetic Construct

<400> SEQUENCE: 20

Met Gly Glu Met His Arg Thr Ser Met Gly Ile Lys Met Glu Ser Gln
1               5                   10                  15

Ile Gln Ala Phe Val Phe Val Phe Leu Trp Leu Ser Gly Val Asp Gly
            20                  25                  30

Asp Ile Val Met Thr Gln Ser His Lys Phe Met Ser Thr Ser Val Gly
        35                  40                  45

Asp Arg Val Ser Ile Thr Cys Lys Ala Ser Gln Asp Val Ser Thr Val
    50                  55                  60

Val Ala Trp Tyr Gln Gln Lys Pro Gly Gln Ser Pro Lys Leu Leu Ile
65                  70                  75                  80

Tyr Trp Ala Ser Thr Arg His Thr Gly Val Pro Asp Arg Phe Thr Gly
                85                  90                  95

Ser Gly Ser Gly Thr Asp Tyr Thr Leu Thr Ile Ser Ser Val Gln Ala
            100                 105                 110

Glu Asp Leu Ala Leu Tyr Tyr Cys Gln Gln His Tyr Thr Thr Pro Phe
        115                 120                 125

Thr Phe Gly Ser Gly Thr Lys Leu Glu Ile Lys Arg Ala Asp Ala Ala
    130                 135                 140

Pro Thr Val Ser Ile Phe Pro Pro Ser Ser Glu Gln Leu Thr Ser Gly
145                 150                 155                 160

Gly Ala Ser Val Val Cys Phe Leu Asn Asn Phe Tyr Pro Arg Asp Ile
                165                 170                 175

Asn Val Lys Trp Lys Ile Asp Gly Ser Glu Arg Gln Asn Gly Val Leu
            180                 185                 190

Asn Ser Trp Thr Asp Gln Asp Ser Lys Asp Ser Thr Tyr Ser Met Ser
        195                 200                 205

Ser Thr Leu Thr Leu Thr Lys Asp Glu Tyr Glu Arg His Asn Ser Tyr
    210                 215                 220

Thr Cys Glu Ala Thr His Lys Thr Ser Thr Ser Pro Ile Val Lys Ser
225                 230                 235                 240

Phe Asn Arg Asn Glu Cys Asn His
                245

<210> SEQ ID NO 21
<211> LENGTH: 482
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

```
Met Ser Ser Pro Gln Thr Leu Asn Thr Leu Thr Pro Thr Met Gly Trp
1               5                   10                  15

Ser Trp Ile Phe Leu Phe Leu Leu Ser Gly Thr Gly Gly Val Leu Ser
            20                  25                  30

Glu Val Gln Leu Gln Gln Ser Gly Pro Glu Leu Val Lys Pro Gly Ala
        35                  40                  45

Ser Val Lys Met Ser Cys Lys Ala Ser Gly Tyr Thr Phe Thr Asp Tyr
    50                  55                  60

Tyr Met Lys Trp Val Lys Gln Ser His Gly Lys Ser Leu Glu Trp Ile
65                  70                  75                  80

Gly Asp Leu Asn Pro Asn Asn Gly Asp Thr Phe Tyr Asn Gln Lys Phe
                85                  90                  95

Lys Gly Lys Ala Thr Leu Thr Val Asp Lys Ser Ser Thr Ala Tyr
            100                 105                 110

Ile Gln Leu Asn Ser Leu Thr Ser Glu Asp Ser Ala Val Tyr Tyr Cys
        115                 120                 125

Ala Arg Glu Ala Gly Ser Ser Phe Gly Ser Ser Cys Asn Tyr Trp Gly
    130                 135                 140

Gln Gly Thr Thr Leu Thr Val Ser Ala Ser Thr Lys Gly Pro Ser Val
145                 150                 155                 160

Phe Pro Leu Ala Pro Ser Ser Lys Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Ser Leu Gly Thr Gln Thr Tyr Ile Cys Asn Val Asn His Lys
225                 230                 235                 240

Pro Ser Asn Thr Lys Val Asp Lys Lys Val Glu Pro Lys Ser Cys Asp
                245                 250                 255

Lys Thr His Thr Cys Pro Pro Cys Pro Ala Pro Glu Leu Leu Gly Gly
            260                 265                 270

Pro Ser Val Phe Leu Phe Pro Pro Lys Pro Lys Asp Thr Leu Met Ile
        275                 280                 285

Ser Arg Thr Pro Glu Val Thr Cys Val Val Val Asp Val Ser His Glu
    290                 295                 300

Asp Pro Glu Val Lys Phe Asn Trp Tyr Val Asp Gly Val Glu Val His
305                 310                 315                 320

Asn Ala Lys Thr Lys Pro Arg Glu Glu Gln Tyr Asn Ser Thr Tyr Arg
                325                 330                 335

Val Val Ser Val Leu Thr Val Leu His Gln Asp Trp Leu Asn Gly Lys
            340                 345                 350

Glu Tyr Lys Cys Lys Val Ser Asn Lys Ala Leu Pro Ala Pro Ile Glu
```

```
                355                 360                 365
Lys Thr Ile Ser Lys Ala Lys Gly Gln Pro Arg Glu Pro Gln Val Tyr
        370                 375                 380

Thr Leu Pro Pro Ser Arg Glu Glu Met Thr Lys Asn Gln Val Ser Leu
385                 390                 395                 400

Thr Cys Leu Val Lys Gly Phe Tyr Pro Ser Asp Ile Ala Val Glu Trp
                405                 410                 415

Glu Ser Asn Gly Gln Pro Glu Asn Asn Tyr Lys Thr Thr Pro Pro Val
                420                 425                 430

Leu Asp Ser Asp Gly Ser Phe Phe Leu Tyr Ser Lys Leu Thr Val Asp
                435                 440                 445

Lys Ser Arg Trp Gln Gln Gly Asn Val Phe Ser Cys Ser Val Met His
        450                 455                 460

Glu Ala Leu His Asn His Tyr Thr Gln Lys Ser Leu Ser Leu Ser Pro
465                 470                 475                 480

Gly Lys

<210> SEQ ID NO 22
<211> LENGTH: 478
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Ser Ser Pro Gln Thr Leu Asn Thr Leu Thr Pro Thr Met Gly Trp
1               5                   10                  15

Ser Trp Ile Phe Leu Phe Leu Leu Ser Gly Thr Gly Gly Val Leu Ser
                20                  25                  30

Glu Val Gln Leu Gln Gln Ser Gly Pro Glu Leu Val Lys Pro Gly Ala
            35                  40                  45

Ser Val Lys Met Ser Cys Lys Ala Ser Gly Tyr Thr Phe Thr Asp Tyr
        50                  55                  60

Tyr Met Lys Trp Val Lys Gln Ser His Gly Lys Ser Leu Glu Trp Ile
65                  70                  75                  80

Gly Asp Leu Asn Pro Asn Asn Gly Asp Thr Phe Tyr Asn Gln Lys Phe
                85                  90                  95

Lys Gly Lys Ala Thr Leu Thr Val Asp Lys Ser Ser Ser Thr Ala Tyr
                100                 105                 110

Ile Gln Leu Asn Ser Leu Thr Ser Glu Asp Ser Ala Val Tyr Tyr Cys
            115                 120                 125

Ala Arg Glu Ala Gly Ser Ser Phe Gly Ser Ser Cys Asn Tyr Trp Gly
        130                 135                 140

Gln Gly Thr Thr Leu Thr Val Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
                180                 185                 190

Trp Asn Ser Gly Ala Leu Thr Ser Gly Val His Thr Phe Pro Ala Val
            195                 200                 205

Leu Gln Ser Ser Gly Leu Tyr Ser Leu Ser Ser Val Val Thr Val Pro
        210                 215                 220

Ser Ser Asn Phe Gly Thr Gln Thr Tyr Thr Cys Asn Val Asp His Lys
```

```
            225                 230                 235                 240
        Pro Ser Asn Thr Lys Val Asp Lys Thr Val Glu Arg Lys Cys Cys Val
                        245                 250                 255

Glu Cys Pro Pro Cys Pro Ala Pro Val Ala Gly Pro Ser Val Phe
                    260                 265                 270

Leu Phe Pro Pro Lys Pro Lys Asp Thr Leu Met Ile Ser Arg Thr Pro
                    275                 280                 285

Glu Val Thr Cys Val Val Val Asp Val Ser His Glu Asp Pro Glu Val
                290                 295                 300

Gln Phe Asn Trp Tyr Val Asp Gly Val Glu Val His Asn Ala Lys Thr
        305                 310                 315                 320

Lys Pro Arg Glu Glu Gln Phe Asn Ser Thr Phe Arg Val Val Ser Val
                        325                 330                 335

Leu Thr Val Val His Gln Asp Trp Leu Asn Gly Lys Glu Tyr Lys Cys
                    340                 345                 350

Lys Val Ser Asn Lys Gly Leu Pro Ala Pro Ile Glu Lys Thr Ile Ser
                    355                 360                 365

Lys Thr Lys Gly Gln Pro Arg Glu Pro Gln Val Tyr Thr Leu Pro Pro
                370                 375                 380

Ser Arg Glu Glu Met Thr Lys Asn Gln Val Ser Leu Thr Cys Leu Val
        385                 390                 395                 400

Lys Gly Phe Tyr Pro Ser Asp Ile Ala Val Glu Trp Glu Ser Asn Gly
                        405                 410                 415

Gln Pro Glu Asn Asn Tyr Lys Thr Thr Pro Pro Met Leu Asp Ser Asp
                    420                 425                 430

Gly Ser Phe Phe Leu Tyr Ser Lys Leu Thr Val Asp Lys Ser Arg Trp
                    435                 440                 445

Gln Gln Gly Asn Val Phe Ser Cys Ser Val Met His Glu Ala Leu His
                450                 455                 460

Asn His Tyr Thr Gln Lys Ser Leu Ser Leu Ser Pro Gly Lys
        465                 470                 475

<210> SEQ ID NO 23
<211> LENGTH: 529
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met Ser Ser Pro Gln Thr Leu Asn Thr Leu Thr Pro Thr Met Gly Trp
        1               5                   10                  15

Ser Trp Ile Phe Leu Phe Leu Leu Ser Gly Thr Gly Gly Val Leu Ser
                    20                  25                  30

Glu Val Gln Leu Gln Gln Ser Gly Pro Glu Leu Val Lys Pro Gly Ala
                    35                  40                  45

Ser Val Lys Met Ser Cys Lys Ala Ser Gly Tyr Thr Phe Thr Asp Tyr
                50                  55                  60

Tyr Met Lys Trp Val Lys Gln Ser His Gly Lys Ser Leu Glu Trp Ile
        65                  70                  75                  80

Gly Asp Leu Asn Pro Asn Asn Gly Asp Thr Phe Tyr Asn Gln Lys Phe
                        85                  90                  95

Lys Gly Lys Ala Thr Leu Thr Val Asp Lys Ser Ser Ser Thr Ala Tyr
                    100                 105                 110
```

```
Ile Gln Leu Asn Ser Leu Thr Ser Glu Asp Ser Ala Val Tyr Tyr Cys
            115                 120                 125

Ala Arg Glu Ala Gly Ser Ser Phe Gly Ser Ser Cys Asn Tyr Trp Gly
            130                 135                 140

Gln Gly Thr Thr Leu Thr Val Ser Ala Ser Thr Lys Gly Pro Ser Val
145                 150                 155                 160

Phe Pro Leu Ala Pro Cys Ser Arg Ser Thr Ser Gly Gly Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
            195                 200                 205

Leu Gln Ser Ser Gly Leu Tyr Ser Leu Ser Ser Val Val Thr Val Pro
        210                 215                 220

Ser Ser Ser Leu Gly Thr Gln Thr Tyr Thr Cys Asn Val Asn His Lys
225                 230                 235                 240

Pro Ser Asn Thr Lys Val Asp Lys Arg Val Glu Leu Lys Thr Pro Leu
                245                 250                 255

Gly Asp Thr Thr His Thr Cys Pro Arg Cys Pro Glu Pro Lys Ser Cys
            260                 265                 270

Asp Thr Pro Pro Pro Cys Pro Arg Cys Pro Glu Pro Lys Ser Cys Asp
            275                 280                 285

Thr Pro Pro Pro Cys Pro Arg Cys Pro Glu Pro Lys Ser Cys Asp Thr
        290                 295                 300

Pro Pro Pro Cys Pro Arg Cys Pro Ala Pro Glu Leu Leu Gly Gly Pro
305                 310                 315                 320

Ser Val Phe Leu Phe Pro Pro Lys Pro Lys Asp Thr Leu Met Ile Ser
                325                 330                 335

Arg Thr Pro Glu Val Thr Cys Val Val Val Asp Val Ser His Glu Asp
            340                 345                 350

Pro Glu Val Gln Phe Lys Trp Tyr Val Asp Gly Val Glu Val His Asn
            355                 360                 365

Ala Lys Thr Lys Pro Arg Glu Glu Gln Tyr Asn Ser Thr Phe Arg Val
        370                 375                 380

Val Ser Val Leu Thr Val Leu His Gln Asp Trp Leu Asn Gly Lys Glu
385                 390                 395                 400

Tyr Lys Cys Lys Val Ser Asn Lys Ala Leu Pro Ala Pro Ile Glu Lys
                405                 410                 415

Thr Ile Ser Lys Thr Lys Gly Gln Pro Arg Glu Pro Gln Val Tyr Thr
            420                 425                 430

Leu Pro Pro Ser Arg Glu Glu Met Thr Lys Asn Gln Val Ser Leu Thr
            435                 440                 445

Cys Leu Val Lys Gly Phe Tyr Pro Ser Asp Ile Ala Val Glu Trp Glu
        450                 455                 460

Ser Ser Gly Gln Pro Glu Asn Asn Tyr Asn Thr Thr Pro Pro Met Leu
465                 470                 475                 480

Asp Ser Asp Gly Ser Phe Phe Leu Tyr Ser Lys Leu Thr Val Asp Lys
                485                 490                 495

Ser Arg Trp Gln Gln Gly Asn Ile Phe Ser Cys Ser Val Met His Glu
            500                 505                 510

Ala Leu His Asn Arg Phe Thr Gln Lys Ser Leu Ser Leu Ser Pro Gly
            515                 520                 525

Lys
```

<210> SEQ ID NO 24
<211> LENGTH: 479
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Ser Ser Pro Gln Thr Leu Asn Thr Leu Thr Pro Thr Met Gly Trp
1               5                   10                  15

Ser Trp Ile Phe Leu Phe Leu Leu Ser Gly Thr Gly Gly Val Leu Ser
            20                  25                  30

Glu Val Gln Leu Gln Gln Ser Gly Pro Glu Leu Val Lys Pro Gly Ala
        35                  40                  45

Ser Val Lys Met Ser Cys Lys Ala Ser Gly Tyr Thr Phe Thr Asp Tyr
    50                  55                  60

Tyr Met Lys Trp Val Lys Gln Ser His Gly Lys Ser Leu Glu Trp Ile
65                  70                  75                  80

Gly Asp Leu Asn Pro Asn Asn Gly Asp Thr Phe Tyr Asn Gln Lys Phe
                85                  90                  95

Lys Gly Lys Ala Thr Leu Thr Val Asp Lys Ser Ser Ser Thr Ala Tyr
            100                 105                 110

Ile Gln Leu Asn Ser Leu Thr Ser Glu Asp Ser Ala Val Tyr Tyr Cys
        115                 120                 125

Ala Arg Glu Ala Gly Ser Ser Phe Gly Ser Ser Cys Asn Tyr Trp Gly
    130                 135                 140

Gln Gly Thr Thr Leu Thr Val Ser Ala Ser Thr Lys Gly Pro Ser Val
145                 150                 155                 160

Phe Pro Leu Ala Pro Cys Ser Arg Ser Thr Ser Glu Ser Thr Ala Ala
                165                 170                 175

Leu Gly Cys Leu Val Lys Asp Tyr Phe Pro Glu Pro Val Thr Val Ser
            180                 185                 190

Trp Asn Ser Gly Ala Leu Thr Ser Gly Val His Thr Phe Pro Ala Val
        195                 200                 205

Leu Gln Ser Ser Gly Leu Tyr Ser Leu Ser Ser Val Val Thr Val Pro
    210                 215                 220

Ser Ser Ser Leu Gly Thr Lys Thr Tyr Thr Cys Asn Val Asp His Lys
225                 230                 235                 240

Pro Ser Asn Thr Lys Val Asp Lys Arg Val Glu Ser Lys Tyr Gly Pro
                245                 250                 255

Pro Cys Pro Ser Cys Pro Ala Pro Glu Phe Leu Gly Gly Pro Ser Val
            260                 265                 270

Phe Leu Phe Pro Pro Lys Pro Lys Asp Thr Leu Met Ile Ser Arg Thr
        275                 280                 285

Pro Glu Val Thr Cys Val Val Val Asp Val Ser Gln Glu Asp Pro Glu
    290                 295                 300

Val Gln Phe Asn Trp Tyr Val Asp Gly Val Glu Val His Asn Ala Lys
305                 310                 315                 320

Thr Lys Pro Arg Glu Glu Gln Phe Asn Ser Thr Tyr Arg Val Val Ser
                325                 330                 335

Val Leu Thr Val Leu His Gln Asp Trp Leu Asn Gly Lys Glu Tyr Lys
            340                 345                 350

Cys Lys Val Ser Asn Lys Gly Leu Pro Ser Ser Ile Glu Lys Thr Ile

```
                355                 360                 365
Ser Lys Ala Lys Gly Gln Pro Arg Glu Pro Gln Val Tyr Thr Leu Pro
            370                 375                 380

Pro Ser Gln Glu Glu Met Thr Lys Asn Gln Val Ser Leu Thr Cys Leu
385                 390                 395                 400

Val Lys Gly Phe Tyr Pro Ser Asp Ile Ala Val Glu Trp Glu Ser Asn
                405                 410                 415

Gly Gln Pro Glu Asn Asn Tyr Lys Thr Thr Pro Pro Val Leu Asp Ser
            420                 425                 430

Asp Gly Ser Phe Phe Leu Tyr Ser Arg Leu Thr Val Asp Lys Ser Arg
            435                 440                 445

Trp Gln Glu Gly Asn Val Phe Ser Cys Ser Val Met His Glu Ala Leu
        450                 455                 460

His Asn His Tyr Thr Gln Lys Ser Leu Ser Leu Ser Pro Gly Lys
465                 470                 475

<210> SEQ ID NO 25
<211> LENGTH: 5
<212> TYPE: PRT
<213> ORGANISM: Artificial Sequence
<220> FEATURE:
<223> OTHER INFORMATION: CDR1 of heavy chain of PUMA 1/2 antibody

<400> SEQUENCE: 25

Asp Tyr Tyr Met Lys
1               5

<210> SEQ ID NO 26
<211> LENGTH: 17
<212> TYPE: PRT
<213> ORGANISM: Artificial Sequence
<220> FEATURE:
<223> OTHER INFORMATION: CDR2 of heavy chain of PUMA 1/2 antibody

<400> SEQUENCE: 26

Asp Leu Asn Pro Asn Asn Gly Asp Thr Phe Tyr Asn Gln Lys Phe Lys
1               5                   10                  15

Gly

<210> SEQ ID NO 27
<211> LENGTH: 17
<212> TYPE: PRT
<213> ORGANISM: Artificial Sequence
<220> FEATURE:
<223> OTHER INFORMATION: CDR3 of heavy chain of PUMA 1/2 antibody

<400> SEQUENCE: 27

Cys Ala Arg Glu Ala Gly Ser Ser Phe Gly Ser Ser Cys Asn Tyr Trp
1               5                   10                  15

Gly

<210> SEQ ID NO 28
<211> LENGTH: 11
<212> TYPE: PRT
<213> ORGANISM: Artificial Sequence
<220> FEATURE:
<223> OTHER INFORMATION: CDR1 of light chain of PUMA 1/2 antibody

<400> SEQUENCE: 28

Lys Ala Ser Gln Thr Val Ser Lys Asp Val Ala
1               5                   10
```

<210> SEQ ID NO 29
<211> LENGTH: 7
<212> TYPE: PRT
<213> ORGANISM: Artificial Sequence
<220> FEATURE:
<223> OTHER INFORMATION: CDR2 of light chain of PUMA 1/2 antibody

<400> SEQUENCE: 29

Tyr Ala Ser Asn Arg Tyr Thr
1               5

<210> SEQ ID NO 30
<211> LENGTH: 6
<212> TYPE: PRT
<213> ORGANISM: Artificial Sequence
<220> FEATURE:
<223> OTHER INFORMATION: CDR3 of light chain of PUMA 1/2 antibody

<400> SEQUENCE: 30

Gln Gln Asp Tyr Ser Ser
1               5

<210> SEQ ID NO 31
<211> LENGTH: 5
<212> TYPE: PRT
<213> ORGANISM: Artificial Sequence
<220> FEATURE:
<223> OTHER INFORMATION: CDR1 of heavy chain of PUMA 3 antibody

<400> SEQUENCE: 31

Ser Tyr Gly Val Tyr
1               5

<210> SEQ ID NO 32
<211> LENGTH: 16
<212> TYPE: PRT
<213> ORGANISM: Artificial Sequence
<220> FEATURE:
<223> OTHER INFORMATION: CDR2 of heavy chain of PUMA 3 antibody

<400> SEQUENCE: 32

Ile Ile Trp Gly Asp Gly Ser Thr Asn Tyr Gln Ser Val Leu Arg Ser
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: CDR3 of heavy chain of PUMA 3 antibody

<400> SEQUENCE: 33

Arg Gly Asp Tyr Asp Val Ala
1               5

<210> SEQ ID NO 34
<211> LENGTH: 15
<212> TYPE: PRT
<213> ORGANISM: Artificial Sequence
<220> FEATURE:
<223> OTHER INFORMATION: CDR1 of light chain of PUMA 3 antibody

<400> SEQUENCE: 34

Lys Ala Ser Gln Thr Val Ser Glu Val Gly Thr Ser Leu Met His
1               5                   10                  15

```
<210> SEQ ID NO 35
<211> LENGTH: 7
<212> TYPE: PRT
<213> ORGANISM: Artificial Sequence
<220> FEATURE:
<223> OTHER INFORMATION: CDR2 of light chain of PUMA 3 antibody

<400> SEQUENCE: 35

Arg Thr Ser Asn Leu Glu Ala
1               5

<210> SEQ ID NO 36

<400> SEQUENCE: 36

000

<210> SEQ ID NO 37
<211> LENGTH: 5
<212> TYPE: PRT
<213> ORGANISM: Artificial Sequence
<220> FEATURE:
<223> OTHER INFORMATION: CDR1 of heavy chain of PUMA 4 antibody

<400> SEQUENCE: 37

Asn Tyr Trp Met Asn
1               5

<210> SEQ ID NO 38
<211> LENGTH: 19
<212> TYPE: PRT
<213> ORGANISM: Artificial Sequence
<220> FEATURE:
<223> OTHER INFORMATION: CDR2 of heavy chain of PUMA 4 antibody

<400> SEQUENCE: 38

Glu Ile Arg Leu Asn Ser Asn Asn Tyr Ala Thr His Tyr Ala Glu Ser
1               5                   10                  15

Val Lys Gly

<210> SEQ ID NO 39
<211> LENGTH: 6
<212> TYPE: PRT
<213> ORGANISM: Artificial Sequence
<220> FEATURE:
<223> OTHER INFORMATION: CDR3 of heavy chain of PUMA 4 antibody

<400> SEQUENCE: 39

Asn Trp Asp Phe Ala Trp
1               5

<210> SEQ ID NO 40
<211> LENGTH: 11
<212> TYPE: PRT
<213> ORGANISM: Artificial Sequence
<220> FEATURE:
<223> OTHER INFORMATION: CDR1 of light chain of PUMA 4 antibody

<400> SEQUENCE: 40

Lys Ala Ser Gln Asp Val Ser Thr Val Val Ala
1               5                   10

<210> SEQ ID NO 41
<211> LENGTH: 7
<212> TYPE: PRT
<213> ORGANISM: Artificial Sequence
<220> FEATURE:
```

-continued

```
<223> OTHER INFORMATION: CDR2 of light chain of PUMA 4 antibody

<400> SEQUENCE: 41

Trp Ala Ser Thr Arg His Thr
1               5

<210> SEQ ID NO 42
<211> LENGTH: 5
<212> TYPE: PRT
<213> ORGANISM: Artificial Sequence
<220> FEATURE:
<223> OTHER INFORMATION: CDR3 of light chain of PUMA 4 antibody

<400> SEQUENCE: 42

Gln Gln His Tyr Thr
1               5
```